(12) United States Patent
Mach

(10) Patent No.: US 6,632,604 B2
(45) Date of Patent: *Oct. 14, 2003

(54) NUCLEIC ACID SEQUENCES OF CIITA GENES WHICH CAN BE INVOLVED IN CONTROLLING AND REGULATING THE EXPRESSION OF GENES ENCODING MHC TYPE II MOLECULES, AND THEIR USE, IN PARTICULAR AS DRUGS

(75) Inventor: Bernard Mach, Geneva (CH)

(73) Assignee: Novimmune SA, Geneva (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/064,199

(22) Filed: Apr. 22, 1998

(65) Prior Publication Data

US 2002/0151691 A1 Oct. 17, 2002

(30) Foreign Application Priority Data

Apr. 22, 1997 (FR) ............................................. 97 04954

(51) Int. Cl.$^7$ ................................................. C12Q 1/68
(52) U.S. Cl. .......................... 435/6; 536/24.1; 536/23.1
(58) Field of Search ............................... 536/23.1, 23.5, 536/24.1; 435/6

(56) References Cited

U.S. PATENT DOCUMENTS 6,022,741 A * 2/2000 Ting et al. ................... 435/366

FOREIGN PATENT DOCUMENTS

EP 0 648 836 4/1995

OTHER PUBLICATIONS

Steimle V. et al, "Complementation cloning of an MHC class II transactivator mutated in hereditary MHC class II deficiency (or bare lymphocyte syndrome)", CELL, Oct. 8, 1993, 75 (1) 135–46, XP002051559.

Riley J.L. et al, "Activation of class II MHC genes requires both the X box region and the class II transactivator (CIITA)", Immunity, May 1995, 2 (5) 533–43, XP002051560, p. 534–536.

Muhlethaler–Mottet A. et al, "Expression of MHC class II molecules in different cellular and functional compartments is controlled by differential usage of multiple promoters of the transactivator CIITA", EMBO Journal, May 15, 1997, (10) 2851–60, XP002051561.

Lennon A.M. et al, "isolationof a B–cell–specific promoter for the human class II transactivator", Immunogenetics, (1997), 45 (4) 266–73, XP002051562.

Steimle V. et al, "Regulationof MHC class 7, 8 II expression by interfereon–gamma mediated by the transactivator gene CIITA", Science, Jul. 1, 1994, 265 (5168) 106–109, XP002051563.

Reith, W. et al, "Molecular defects in the bare lymphocyte syndrome and regulation of MHC class II genes", Immunology Today, vol. 16, 1995, Cambridge GB, pp. 539–545, XP002051564.

Steimle V. et al, "Major histocompatibility complex class II deficiency: a disease of gene regulation", Advances in Immunology, (1996), 61 327–340, XP002051565.

* cited by examiner

Primary Examiner—James Martinell
(74) Attorney, Agent, or Firm—Mintz, Levin, Cohn, Ferris, Glovsky and Popeo, P.C.; Ivor R. Elrifi, Esq.

(57) ABSTRACT

The present invention relates to nucleic acid sequences which comprise all or part of a nucleic acid sequence of a CIITA gene. These sequences can comprise a sequence which exhibits a transcriptional promoter activity, which activity is, in particular, specifically expressed in one cell type. The sequences can also comprise a coding sequence.

Therapeutic and diagnostic applications, in particular relating to disorders in which it is desirable to act on the level at which genes which encode the class II molecules of the major histocompatibility complex (MHC) are expressed.

18 Claims, 6 Drawing Sheets

```
              AP1              CCAAT BOX      NF-IL6rev  NFGMb
TGGAGTC TGAATCA ACCCAAAAG CCAAT ATCCATC CGTTCA TCA GGAA CCCCAGCCTACA
              BOX 1                                      E2A
ACGCAAA AGAGGAAAT CTTCCTAAG TAGAAATAAACTGTAATAAATT GCAGAGG TTCCCT
+1
CGTCCTGGTTTTCACTTCATGTTTTGGATGCTGCATGCTGGGTGAGCGGAGATTCCAGGC

ACTGGCCAGGGCAGCTGCCCTGACTCCAAGGGCTGCCATG
```

```
CTGCAGAAGGTGGCAGATATTGGCAGCTGGCACCAGTGCGGTTCCATTGTGATCATCATT
                                                     E2A rev
TCTGAACGTCAGACTGTTGAAGGTTCCCCCAACAGACTTTCTGTGCAACTTTCTGTCTTC
              IRF1/2                                      MYB/
ACCAAATTCAGTCCACAGTAAGGAAGTGAAATTAATTTCAGAGGTGTAGGGAGGGCTTAA
MYC rev
GGGAGTGTGGTAAAATTAGAGGGTGTTCAGAAACAGAAATCTGACCGCTTGGGGCCACCT
                                     OCTrev
TGCAGGGAGAGTTTTTTTGATGATCCCTCACTTGTTTCTTTGCATGTTGGCTTAGCTTGG
                  +1
CGGGCTCCCAACTGGTGACTGGTTAGTGATGAGGCTAGTGATGAGGCTGTGTGCTTCTGA
GCTGGGCATCCGAAGGCATCCTTGGGGAAGCTGAGGGCACGAGGAGGGGCTGCCAGACTC
CGGGAGCTGCTGCCTGGCTGGGATTCCTACACAATG
```

Fig. 3

```
GGGGAGAAGTCAGAGGTAACCTTGCCCCCTCCCTCAATTCCAGATGAGGAAATTCAGGCC
TGAAAAGGGAAAGTGACCACCTCAAAGTCTCATGCCTTGGAGGACCCAGCAGGAATCCAA
GACCTCTGAAAAGGACCGGCAGGGCTCTTGCCACGGCTGGGGGTGTGGTCATGGTAACAC
AGGTTTTCCATCCATGGAAGGTACCTGAGGGATTTTCTCTTCCTCCCTAGGGCCAGCATC
AGAGGAGTGAATAGCTCAGTTAGCTCATCTCAGGGGCCATGTGCCCTCGGAGGTGGTTTG
CCACTTTCACGGTTGGACTGAGTTGGAGAGAAACAGAGACCCACCCAGGGGTGGGGACAA
GCTCCCTGCAACTCAGGACTTGCAGATCACTTGCCCAAGTGGCTCCCTAGCTCCTGGCTC
             NfkB
CTGGCCCGGGGCCTGGGACTCTCCCCGAAGTGGGGCTGGCCACTGTGAGGAACCGACTGG
                                 NFGMa        GAS      Ebox
AGGCAGGGACCTCTTGGATGCCCCAGGCAGTTGGGATGCCACTTCTGATAAAGCACGTGG TGGCCACAGTAGGTGCTTGGTTGCTCCACAGCCTGGCCCGAGCTCAGCGCTGCAGAAAGA
IRF1/2
AAGTGAAAGGGAAAAAGAACTGCGGGGAGGCGGGGAGGTAGGATGACCAGCGGACGAGCT
     +1
GCCACAGACTTGCCGCGGCCCCAGAGCTGGCGGGAGGGAGAGGCCACCAGCAGCGCGCGC
GGGAGCCCGGGGAACAGCGGCAGCTCACAGTGTGCCACCATG
```

Fig. 4

NUCLEIC ACID SEQUENCES OF CIITA GENES WHICH CAN BE INVOLVED IN CONTROLLING AND REGULATING THE EXPRESSION OF GENES ENCODING MHC TYPE II MOLECULES, AND THEIR USE, IN PARTICULAR AS DRUGS

This application claims priority under 35 U.S.C. §§119 and/or 365 to Patent Application No. 97-04954 filed in France on Apr. 22, 1997; the entire content of which is hereby incorporated by reference.

The present invention relates to novel nucleic acid sequences which can be involved in controlling and regulating the expression of genes encoding MHC type II molecules and to their use, in particular as drugs for treating disorders in which it is desirable to act on the level at which genes encoding MHC type II molecules are expressed.

The molecules of the class II major histo-compatibility complex (termed MHC in that which follows) are heterodimeric transmembrane glycoproteins which are directly involved in activating T helper CD4+ lymphocytes during the course of the immune response.

In man, this class II complex is represented by the molecules which belong to the HLA (human leucocyte antigen) system. The genes which encode the α and β chains of which the HLA-DR, HLA-DQ and HLA-DP molecules are composed are located within the D region of chromosome 6.

Expression of these genes is very highly regulated. In contrast to the genes which encode the MHC type I molecules, which are expressed ubiquitously, expression of the genes which encode the MHC class II molecules is either constitutive, in only a few cell types such as B lymphocytes, activated T lymphocytes, macrophages, cells of the thymic epithelium, or dendritic cells such as the Langerhans cells, or is induced following stimulation, for example by cytokines, more specifically by interferon γ (INF γ) or interleukin 4 (IL4), in several other cell types such as cells which belong to the macrophage or monocyte line, endothelial cells, fibroblasts, muscle cells or cancer cells such as melanoma cells.

Furthermore, expression of the genes which encode MHC class II molecules in B lymphocytes is transient. Thus, differentiation of the B cells into plasma cells which produce the immunoglobulins is accompanied by the suppression of certain genes including those which encode MHC class II.

Similarly, it has been shown that the level at which MHC type II molecules are expressed is a determining factor in the process of T cell activation.

As a consequence, it is clearly apparent that the molecular mechanisms by which expression of these genes is regulated constitute a key element in the efficacy of the immune response. Any defect in this regulatory process may result in significant immunological disorders or autoimmune diseases. Thus, abnormal expression of the MHC class II genes has in some cases been observed at the surface of cells which should not normally express these genes. Similarly, it is possible to observe over-expression of these genes, leading to an activation of the CD4+ lymphocytes which is aberrant and uncontrolled [Bottazzo et al., 1986, Immunol. Rev., 94, 137–169]. Events of this kind could, at least in part, be responsible for disorders such as insulin-dependent diabetes, multiple sclerosis, rheumatoid arthritis and lupus erythematosus. Conversely, it has been possible to demonstrate an immunodeficiency in some patients which has resulted from a disturbance in the expression of MHC class II genes. Mention may, for example, be made of the BLS (bare lymphocytes syndrome) syndrome which is a recessive autosomal disorder in which expression of the MHC class II genes is very limited if not to say non-existent, a situation which finds expression in the absence of cellular and humoral immune responses and is accompanied by a large number of infections which are often fatal.

Several scientific groups have analysed the mechanisms by which expression of the MHC class II genes is regulated and have identified a number of transactivating molecules which are capable of binding, directly or indirectly, to promoter sequences which are specific for the said genes [for a review, see Mach et al., 1996, Annu. Rev. Immunol. 14, 301–331].

The applicant has previously identified and characterized one of these factors, i.e. the CIITA factor (class II transactivator) [Steimle et al., 1993, Cell 75, 135–146 and EP 648836]. Furthermore, document WO 9606107 shows that there are two domains within the CIITA factor which are more involved in activating transcription of the MHC class II genes, more specifically the domain which is defined by SEQ ID No. 21 of the present invention and which corresponds to the translation of the nucleic acid sequence according to SEQ ID No. 17. Nevertheless, surprisingly and contrary to that which is observed in the case of other factors which are involved in regulating expression of the MHC class II genes (Cogswell et al., 1991, Crit. Rev. Immunol. 11, 87–112), Steimle et al. have demonstrated that expression of the CIITA factor coincides strictly with expression of the MHC class II genes and is required absolutely both for constitutively expressing and for inducing the said MHC genes. Furthermore, Silacci et al. (1994, J. Exp. Med., 180, 1329–1336) have demonstrated that suppression of the MHC class II genes during plasma cell differentiation is associated with suppression of the gene which encodes CIITA factor.

Moreover, Lennon et al. (1997, Immunogenetics, 45, 266–273) have identified the promoter sequence of a CIITA gene, which sequence is responsible for the differential expression of this factor in B cells. However, the existence of this sequence alone does not explain why differential expression of the CIITA factor is observed in different cell types. Furthermore, it does not account for induction by cytokines.

Using samples derived from different tissues of human origin, the applicant has now identified the complex organization of the sequences which ensure regulation of the expression of the CIITA factor, has isolated and characterized other promoter regions and has demonstrated the existence of several forms of CIITA factor, and has also demonstrated the existence of different CIITA genes.

The expression "CIITA gene" is understood as meaning a nucleic acid sequence which consists of a promoter (P) moiety, an untranslated (UT) moiety and a coding (Prot) moiety, with the coding moiety encoding one of the identified forms of CIITA factor.

More precisely, the inventors have identified a number of nucleic acid sequences which represent CIITA genes and which are therefore capable, in particular, of being involved in controlling and regulating the expression of genes encoding MHC class II molecules. The expression "nucleic acid sequence which represents CIITA genes" is understood as meaning that the sequence in question comprises all or part of a nucleic acid sequence corresponding to the mRNAs which derive from the different tissues or cell lines which express CIITA activity either constitutively or following induction. Such sequences can therefore equally well be sequences which are at least partially coding, as for example sequences which are involved in controlling the expression, in particular, of sequences which possess a transcriptional promoter activity.

The expression "nucleic acid sequence" is understood as meaning a natural, isolated, or synthetic, double-stranded or single-stranded DNA and/or RNA fragment which designates a precise linked-up series of modified or unmodified nucleotides and which makes it possible to define a fragment or a region of a nucleic acid.

The expression "polypeptide" is understood as meaning a precise, natural, isolated, or synthesized, modified or unmodified linked-up series of amino acids, independently of its size or its function.

The expression "allelic variant" of a polypeptide is understood as meaning the entirety of the mutated polypeptides and the polymorphisms which can exist in man, and which are obtained, in particular, by truncating, substituting, deleting or adding on amino acid residues, as well as the artificial variants which are employed in vitro.

The expression "nucleic acid sequence which exhibits a transcriptional promoter activity" is understood as meaning a nucleic acid sequence which makes it possible to control, that is initiate and/or modulate, the transcription of at least one homologous or heterologous gene which is located downstream of the said sequence. Similarly, reference will be made to the promoter function of the said sequences.

The expression "nucleic acid sequence which is homologous to a first nucleic acid sequence" is understood as meaning a nucleic acid sequence which naturally exhibits a functional link with the said first sequence. Thus, according to the invention, a nucleic acid sequence which exhibits a CIITA promoter activity, that is which naturally directs the transcription of a nucleic acid sequence encoding a CIITA factor, is, for example, considered as being homologous to this same nucleic acid sequence which encodes a CIITA gene. In the opposite case, reference will be made to a "heterologous nucleic acid sequence".

The expression "reporter gene" is understood as meaning any nucleic acid sequence which is located downstream of a second nucleic acid sequence and which makes it possible to analyse the transcriptional promoter activity of the said second sequence. Thus, transcription of this reporter gene is manifested by the appearance of a product (RNA or polypeptide) which can readily be detected using well known conventional techniques.

It should be understood that the present invention does not relate to genomic nucleotide sequences in their natural chromosomal environment, that is in the natural state; on the contrary, the sequences are sequences which have been isolated, meaning that they have been directly or indirectly withdrawn, for example by copying (cDNA), and that their environment has been at least partially modified.

The invention thus relates to a nucleic acid sequence which comprises all or part of a nucleic acid sequence of a CIITA gene and which is selected from the sequences SEQ ID No. 1, SEQ ID No. 2 and SEQ ID No. 3, and their complementary sequences.

The invention more specifically relates to such a nucleic acid sequence which comprises all or part of a sequence which exhibits a transcriptional promoter activity.

Particularly interesting sequences which may be mentioned are those which comprise all or part of a sequence which is selected from SEQ ID No. 4, SEQ ID No. 5 and SEQ ID No. 6, and their complementary sequences.

The sequences which contain all or part of the sequence identified as SEQ ID No. 4, or its complementary sequence, are particularly advantageous in that they are able to express their transcriptional promoter activity specifically in one cell type, such as dendritic cells.

Certain sequences which have been identified in accordance with the invention are able to express their transcriptional promoter activity following induction by a cytokine such as, for example, interferon γ or interleukin 4. A preferred example of such a sequence is represented by the sequence which comprises all or part of an identified sequence SEQ ID No. 6, or its complementary sequence.

The invention also relates to the nucleic acid sequences which comprise all or part of a sequence selected from:

a) a nucleic acid sequence which encodes a polypeptide which possesses an amino acid sequence such as shown in SEQ ID No. 16, and its complementary sequence, b) the sequences SEQ ID No. 7, SEQ ID No. 8, SEQ ID No. 10 and SEQ ID No. 11 and their complementary sequences, c) a nucleic. acid sequence which encodes an allelic variant of a polypeptide such as defined in a), or its complementary sequence.

The present invention furthermore relates to a nucleic acid sequence which comprises at least one sequence exhibiting a transcriptional promoter activity, such as, in particular, the sequences which comprise all or part of the sequences SEQ ID No. 4, SEQ ID No. 5 or SEQ ID No. 6, or their complementary sequences, which sequence is located upstream of at least one heterologous or homologous nucleic acid sequence such as, for example, a nucleic acid sequence which comprises all or part of a sequence selected from:

a) a nucleic acid sequence which encodes a polypeptide which consists of the amino acids identified in SEQ ID No. 16, SEQ ID No. 17, SEQ ID No. 18 or SEQ ID No. 19, or its complementary sequence, b) the identified nucleic acid sequences is SEQ ID No. 7, SEQ ID No. 8, SEQ ID No. 9, SEQ ID No. 10, SEQ ID No. 11, SEQ ID No. 12, SEQ ID No. 13, SEQ ID No. 14 and SEQ ID No. 15, and their complementary sequences, c) a nucleic acid sequence which encodes an allelic variant of a polypeptide such as defined in a), or its complementary sequence.

It should be made clear that, in this case, it is possible to have at least two sequences which exhibit a transcriptional promoter activity and/or at least two heterologous or homologous nucleic acid sequences which are situated contiguously or at a distance in relation to each other, and in the same direction or in opposite directions, without the transcriptional promoter function or the transcription of the said sequences thereby being affected.

Similarly, it is possible, in this type of nucleic acid construction, to introduce "neutral" nucleic acid sequences or introns which do not affect transcription and which are spliced before the translation step. Sequences of this nature, and their uses, are widely described in the literature.

According to the invention, the nucleic acid sequences, or their fragments, can, in particular, encode all or part of polypeptides which possess the amino acid sequence of a CIITA factor as described in the present invention.

It will then be stated that they encode CIITA polypeptides.

The sequences can also be employed as probes or as primers in processes for detecting or identifying or enzymically amplifying nucleic acid. In this case, the fragments exhibit a minimum size of 10 bases, and preference will be given to fragments of 20 bases, preferably of 30 bases.

The present invention also relates to a nucleic acid sequence which possesses a sequence which is complementary to a target sequence which belongs to a gene or to an RNA whose expression it is desired to block specifically. An antisense oligonucleotide which hybridizes with the sequence to which it is complementary and can thereby block expression of the mRNA having this sequence constitutes such a sequence. In this context, the term "oligonucleotide" is used in a general manner to designate a polynucleotide of from 2 to 100, more generally of from 5 to 50, ribonucleotides, deoxyribonucloetides or mixed nucleotides in a series. According to the invention, such a sequence is able to hybridize with a nucleic acid sequence which comprises a sequence exhibiting a transcriptional promoter activity or with a nucleic acid sequence comprising a sequence such as previously defined in a), b) or c), and is furthermore able either to block the promoter activity of the said sequence or to inhibit the synthesis of the polypeptide which is encoded by the said sequence.

The hybridization conditions are determined, according to the invention, in order to ensure at least 95% homology. The skilled person is in possession of sufficient knowledge to enable him to define the said conditions.

Even if the described sequences are generally normal sequences, the invention also relates to sequences which are mutated to the extent that they include at least one point mutation and preferably less than 20 mutations in all.

Preferably, the present invention relates to nucleotide sequences in which the point mutations are not silent, that is they lead either to a change in the regulation of the efficacy or of the cellular specificity of the transcription of the gene which is located downstream of the said sequence, or to a change in the coding sequence which affects expression of the CIITA gene, or to a change in the encoded amino acid as compared with the normal sequence, which change affects the function of the corresponding CIITA factor.

The present invention relates, in particular, to a nucleic acid sequence which comprises at least one mutation which affects the transcriptional promoter function of the said sequence. Preferably, these mutations concern the regions which are involved in the transcriptional promoter activity and which make it possible to bind factors which are involved in the transcription initiation, activation or modulation step or in transcription more generally. These regions can, for example, consist of at least one site which is involved in the transcription process and which is selected from the group consisting of the NF-GMb site (Shannon et al., 1988, Proc. Natl. Acad. Sci. USA, 85, 674–678), the NF-IL6 site (Akira and Kishimoto, 1992, Immunil. Rev. 127, 25–50), the PEA3 site (Wasylyk et al., 1989, EMBO J., 8, 3371–3378), the API site (Pollock and Treisman, 1990, Nucleic Acid Res. 18, 6197–6204), the CCAAT box (Dorn et al., 1987, Cell, 50, 863–872), the E2A box (Murre et al., 1989, Cell, 56, 777–783), the IRF1/2 site (Tanaka et al., 1993, Molecular and Cellular Biology, 13, 4531–4538), the MYC site (Agira et al., 1989, EMBO J., 8, 4273–4279), the OCT site (Rosales et al., 1987, EMBO J., 6, 3015–3025), the NF-GMa site (Shannon et al., 1988, Proc. Natl. Acad. Sci. USA, 85, 674–678), the GAS box (Pelligrini and Schindler, 1993, Trends Biochem. Sci., 18, 338–342), the E box (Blackwell et al., 1990, Science, 250, 1149–1151) and the NFκB site (Sen and Baltimore, 1986, Cell, 46, 705–716).

The present invention also relates to a nucleotide sequence which can include unnatural nucleotides, in particular sulphur-containing nucleotides, for example, or nucleotides having an α or β structure, or nucleotides which are labelled with a label which is, by way of example, selected from the group consisting of an enzyme, biotin, iminobiotin, a fluorescent compound, a radioactive compound, a chemiluminescent compound, an electrodense compound, a magnetic compound, an antigen, a hapten and an antibody.

The present invention also relates to cloning or expression vectors which include at least one nucleotide sequence such as previously described.

These cloning or expression vectors can additionally include elements which ensure expression of the sequence in the host cell, in particular promoter sequences and/or regulatory sequences which are effective in the said cell, if the sequence is a coding sequence.

If the sequence is a sequence which possesses a transcriptional promoter activity, the vector will additionally include homologous or heterologous nucleic acid sequences which it is desired to express in the said cell.

Preferably, these cloning or expression vectors comprise at least one gene of interest which is placed under the control of at least one nucleic acid sequence which is as previously described and which exhibits a transcriptional promoter activity.

The said gene of interest can, for example, be selected from the group which consists of the genes which encode the CIITA factor and the α and β chains of the HLA-DR, HLA-DQ and/or HLA-DP molecules, and reporter genes, such as the gene which encodes rabbit β globin.

The vector in question can be selected from the autonomously replicating vectors or from the vectors which integrate into the chromosome.

In the case of an autonomously replicating system, use will preferably be made, depending on whether the cell host is prokaryotic or eukaryotic, of systems of the plasmid type or of viral systems, with it being possible for the viral vectors to be, in particular, adenoviruses, poxviruses or herpesviruses. The skilled person is familiar with the techniques which can be used for each of these viruses.

When it is desired to integrate the sequence into the host cell chromosomes, it will be necessary to provide one or more sequences derived from the cell host at each end of the nucleic acid sequence to be integrated in order to ensure recombination. These are also processes which are widely described in the prior literature. Use can, in particular, be made of systems of the plasmid or viral type such as, for example, retroviruses or AAVs (adenoassociated viruses).

The invention also relates to prokaryotic or eukaryotic cells which have been transformed with a vector such as previously described, in particular in order to ensure expression of at least one of the forms of the CIITA factor which have been identified in accordance with the invention.

Cells which can be used for implementing the invention and which may indeed be mentioned are prokaryotic cells, yeast cells and animal cells, in particular cultures of mammalian cells.

Preferably, the host cell is selected from the group consisting of dendritic cells, B lymphocytes, T lymphocytes, macrophages, monocytes, thymus epithelium cells, muscle cells, fibroblasts, endothelial cells and cancer cells, in particular melanoma cells.

The cells which have thus been obtained can be used to prepare natural or mutated CIITA polypeptides and also fragments of these polypeptides.

These cells can also be used as model cells for the purpose of studying the mechanisms of regulating the transcriptional promoter function of the sequences which have been identified in accordance with the invention and of identifying specific inhibitors whose action could possibly be targeted in a given cell type. These cells can additionally be used as model cells for the purpose of studying the interactions between the different CIITA factors which have been isolated, or their variants, and the regions which direct transcription of the genes encoding the MHC class II molecules, and, especially, for the purpose of selecting the variants of the CIITA factors which are able to act as agonists or antagonists on the CIITA receptor. These types of cell model can be constructed using known techniques of genetic manipulation. Furthermore, the use of such cell models with a view to testing pharmaceutical compounds is well known to the skilled person.

The present invention also relates to organisms, such as animals, in particular mice, whose genome has been genetically modified in order to integrate at least one of the nucleic acid sequences according to the invention. In this case, again, these animals can be used as model animals in order to test the efficacy of particular pharmaceutical products.

The present invention also relates to a process for producing a CIITA polypeptide, in particular as defined in SEQ ID No. 16, SEQ ID No. 17, SEQ ID No. 18 or SEQ ID No. 19, or an allelic variant of one of these polypeptides, which process comprises (i) culturing a host cell, which has been transformed with a vector which includes a nucleic acid sequence encoding a CIITA polypeptide as previously described, under culture conditions which are appropriate for producing the said polypeptide, and (ii) recovering the said polypeptide.

The said polypeptide can be recovered intracellularly or extracellularly in the culture medium when the vector has been designed for assuring secretion of the polypeptide by the expedient, for example, of using a leader sequence, with the polypeptide being in the form of a prepolypeptide. The constructs which enable polypeptides to be secreted are known, both for prokaryotic systems and eukaryotic systems.

The present invention also relates to a CIITA polypeptide which can be obtained by implementing the abovedescribed process.

The present invention additionally relates to CIITA polypeptides which correspond to the previously described nucleic acid sequences and which are in unnatural form, i.e. they are not used in their natural environment but are obtained by purification from natural sources or else obtained by genetic recombination.

More specifically, the invention relates to a polypeptide which is characterized in that it comprises at least one sequence which is selected from:
  a) an amino acid sequence which consists of SEQ ID No. 16, or its allelic variants,
  b) an amino acid sequence which consists of a part of the sequence SEQ ID No. 16, or its allelic variants.

Preferably, a peptide of this nature is characterized in that at least one part of its sequence is defined in the space between amino acid 1 and amino acid 94 of the sequence SEQ ID No. 16.

The invention also relates to the same polypeptides which are obtained by chemical synthesis and which can include unnatural amino acids. The invention also relates to the said polypeptides which are in a form which is totally or partially retro and/or inverso and which exhibit an activity which is equivalent to that observed in the case of the native CIITA factor, or one of its variants, according to the present invention, or at least an immunological activity which is identical to that of the parent CIITA factor.

Furthermore, the polypeptides, and more specifically their variants, such as previously described, can exhibit the same function of transactivating the expression of the genes encoding MHC class II molecules as a CIITA factor or, at least, the same ability to bind to the specific site for binding a CIITA factor during expression of the said genes.

The present invention additionally relates to an antibody which is directed against any one of the previously described polypeptides or against a polypeptide which contains at least one mutation affecting the function of the CIITA factor, as described below, and, more specifically, to a polyclonal or monoclonal antibody which is obtained by the immunological reaction of a human or animal organism with an immunogenic agent which comprises at least one of the said polypeptides.

The invention also relates to molecules which are able to inhibit either the function of the polypeptides which have been identified according to the invention in activating expression of the genes encoding the MHC class II molecules or the ability of these polypeptides to bind to the CIITA-binding site. These molecules can be polypeptides which contain at least one mutation which affects the function of the CIITA factor. A modified polypeptide of this nature, which consists, for example, of a structural analogue of the said polypeptide, can act as a lure. The molecules can also be antibodies, such as presented above, which are able, for example, to block either all or part of the CIITA factor which is able to react with its specific receptor, or a region of the CIITA factor which is able to interact with at least one other transactivating factor during expression of the genes encoding the MHC class II molecules.

The invention also relates to molecules which are able specifically to inhibit expression of the genes which encode MHC class II molecules in dendritic cells. These molecules consist, in particular, of all or part of a nucleic acid sequence which contains at least one mutation which affects the transcriptional promoter function of the said sequence, with the mutation(s) being located in an identified nucleic acid sequence SEQ ID No. 4, or its complementary sequence.

The invention also relates to molecules which are able specifically to inhibit the induction, by cytokines, of the expression of the genes which encode MHC class II molecules. These molecules consist, in particular, of all or part of a nucleic acid sequence which contains at least one mutation which affects the transcriptional promoter function of the said sequence, with the mutation(s) being located in the identified nucleic acid sequence SEQ ID No. 6, or its complementary sequence.

The present invention also relates to pharmaceutical compositions which comprise, as the active principle, at least one substance such as a nucleic acid sequence or an inhibitory molecule as previously defined. More specifically, the invention relates to a pharmaceutical composition for treating disorders in which it is desired to increase expression of the genes encoding MHC class II molecules, in particular in one cell type, more specifically in a dendritic cell. Furthermore, it is possible to observe this increase in the expression of the genes encoding MHC class II molecules following induction by a cytokine, more specifically by interferon γ or interleukin 4, in particular when the said pharmaceutical composition comprises at least one substance which consists of a nucleic acid sequence which can be activated by the said cytokine, as previously described. The invention additionally relates to a said pharmaceutical composition for treating disorders in which it is desired to reduce expression of the genes encoding MHC class II molecules, more specifically to a pharmaceutical composition which comprises, as the active principle, a) either a nucleic acid sequence according to the invention, the sequence of which is modified such that the promoter activity of the said sequence is affected, or which leads to the production of an inactive CIITA polypeptide, as previously described, or b) an inactive CIITA polypeptide.

The invention furthermore relates to a vaccine which can be used, in particular, for treating cancer or autoimmune diseases, characterized in that it comprises at least one of the pharmaceutical compositions presented above.

Finally, the present invention relates, more specifically, to methods for diagnosing a predisposition to a disorder which is linked to a disturbance in the expression of the genes encoding MHC class II molecules, characterized in that a biological sample is taken from a patient, and the presence of at least one mutation, within either sequences which exhibit a transcriptional promoter activity or sequences which encode one of the identified CIITA factors according to the present invention, is determined by analysing the said nucleic acid sequences and comparing with the wild-type sequences according to the invention, with the presence of at least one such mutation being indicative of a predisposition of the said patient to the said disorder.

A large number of disorders which are directly or indirectly linked to a disturbance in the expression of the genes encoding MHC class II molecules have been described in the literature. We may cite, by way of example, disorders such as insulin-dependent diabetes, multiple sclerosis, rheumatoid arthritis and lupus erythematosus, one of the elements of which disorders could be overexpression of the genes encoding MHC class II molecules; or, conversely, the BLS (bare lymphocytes syndrome) syndrome, which is associated with a severe immunodeficiency.

Sought-after mutations which may be mentioned, more specifically, are mutations which affect the promoter function of nucleic acid sequences, mutations which affect the cellular specificity of the said promoter function, or mutations which affect induction of the said promoter function by a cytokine.

The analysed nucleic acid sequence can equally well be a genomic DNA, a cDNA or an RNA.

The diagnostic tools which are based on the present invention can be used to make a positive and differential diagnosis in a subject taken in isolation or else to make a presymptomatic diagnosis in a subject at risk.

There are, of course, a very large number of methods for demonstrating a mutation in a gene as compared with the natural gene; they can be implemented by studying the genomic DNA, the cDNA, the RNA and/or the polypeptide. They can, essentially, be divided into two broad categories, with the first type of method being that in which the presence of a mutation is detected by comparing the mutated sequence with the corresponding natural, unmutated sequence, and the second type being that in which the presence of the mutation is detected indirectly. Advantageously, the mutation can be detected by demonstrating mismatches, which are due to the presence of the mutation, after analysing by means of hybridization which is carried out using at least one oligonucleotide probe which is specific for the sought-after mutation.

In each of the cases, preference will in general be given to the methods in which all or part of the sequence corresponding to all or part of the identified sequences SEQ ID No. 1, SEQ ID No. 2 or SEQ ID No. 3 is amplified prior to demonstrating the mutation. These amplification methods are well known.

Furthermore, the mutated CIITA factors which are found in subjects who are exhibiting disorders in the expression of the genes encoding MHC type II molecules can exhibit an antigenicity which is different from that of the identified natural CIITA factors SEQ ID No. 16, SEQ ID No. 17 or SEQ ID No. 18. It is therefore possible to diagnose or prognosticate susceptibility to disorders which are linked to deregulation of the expression of the genes encoding MHC type II molecules by demonstrating the presence of the product of the mutated CIITA gene, for example using antibodies, in particular monoclonal antibodies, as previously described.

Other characteristics and advantages of the present invention will be apparent from reading the following examples, which are illustrated by FIGS. 1 to 9. Nevertheless, the invention is not limited to the contents of the said examples.

FIGURE LEGENDS

FIG. 1 depicts the four 5' ends of the CIITA mRNAs which were identified as described in Example 1. The coding regions are indicated by the wide boxes while the 5' untranslated regions are indicated by the smaller boxes. The non-homologous regions are shown as clearly filled-in regions. The diagram shows the positions of the two primers, P1 and P2, which were used for the RACE-PCR amplification.

FIG. 3 shows the sequence, SEQ ID No. 27 and the positions of the different sites for binding known transcription factors which were identified on the sequence, of the 5'-flanking region of the type III CIITA gene. The main transcription initiation site is also indicated by an arrow at +1.

FIG. 4 shows the sequence, and the positions of the different sites for binding known transcription factors which were identified on the sequence, of the 5'-flanking region of the type IV CIITA gene. The main transcription initiation site is also indicated by an arrow at +1.

Figure 5:
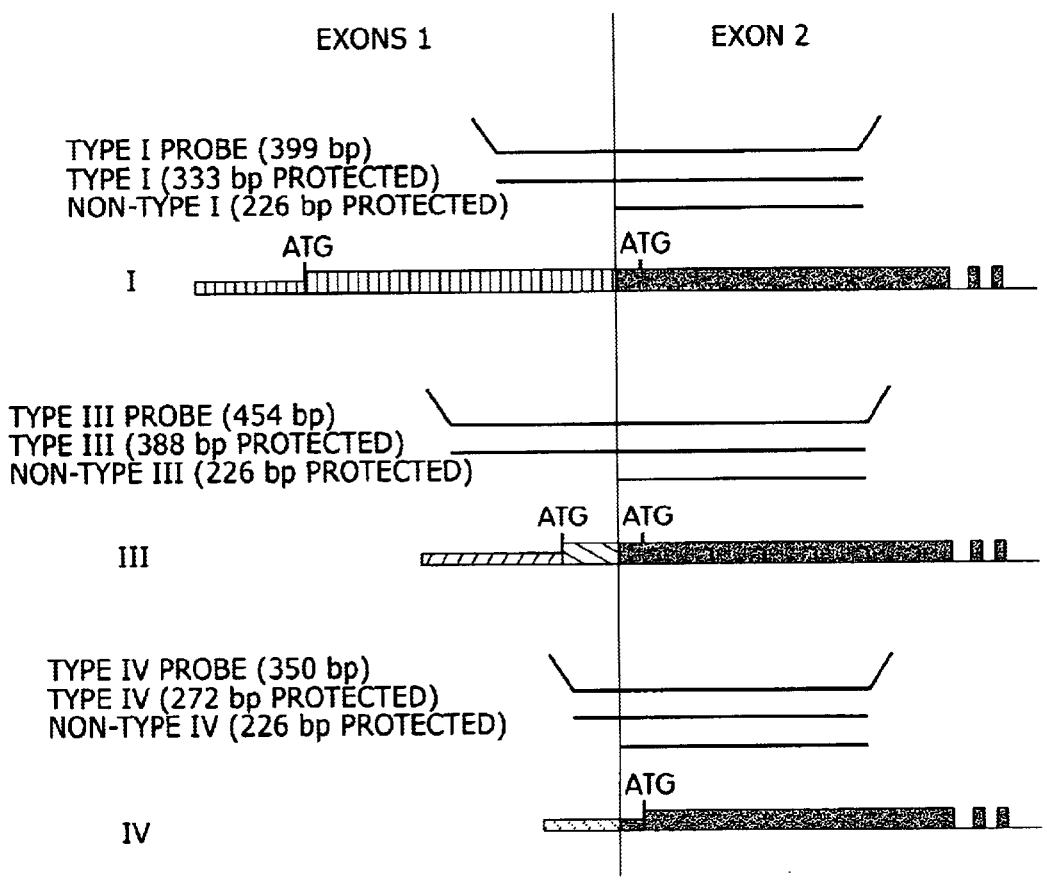

FIG. 5 is a diagrammatic representation of the probes which were used in the RNAse protection tests during the analysis of the expression profiles of the different CIITA mRNAs. The different probes are shown with their sizes "before" and "after" digestion by RNAse. Each of the probes corresponds to a part of exon 1 and has 226 bases which are common to each of the mRNAs.

Figure 6:
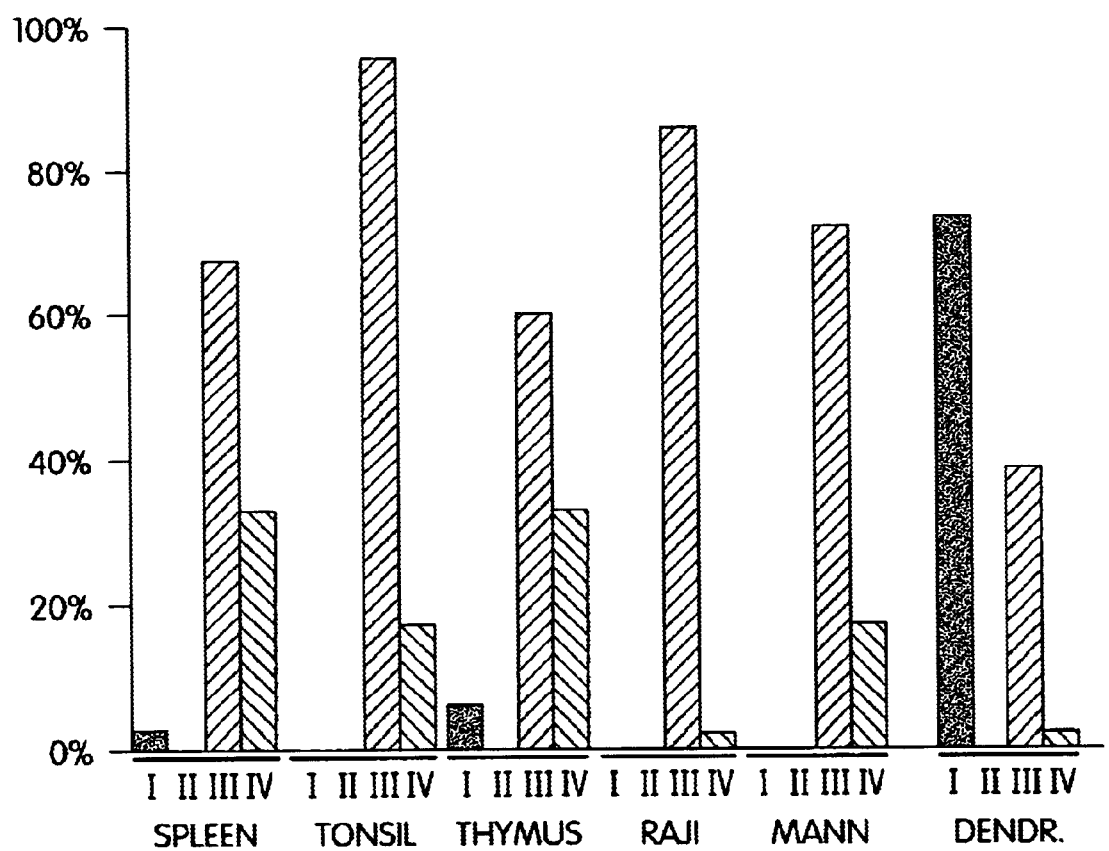

FIG. 6 is a diagrammatic representation of the differential expression of the four types of CIITA transcript. The quantity of each of the mRNA types is indicated as a percentage as compared with the total quantity of CIITA expression, as measured using the internal control and after PhosphoImager quantification of the fragments which were obtained following the RNAse protection analysis.

Figure 7:
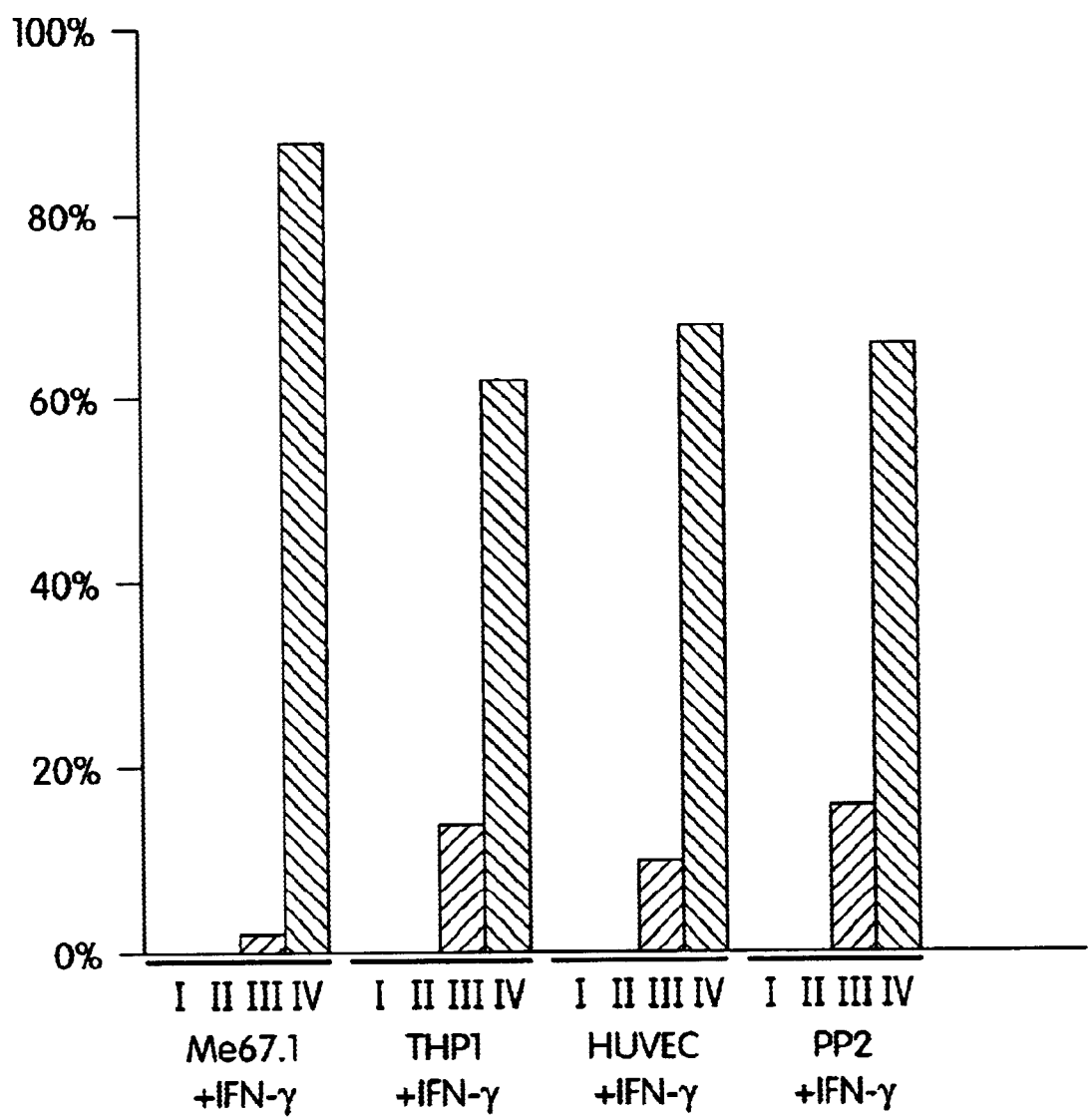

FIG. 7 is a diagrammatic representation of the same type as that in FIG. 6 except that expression of the CIITA transcripts is observed following induction with interferon α (+IFNγ).

Figure 8:
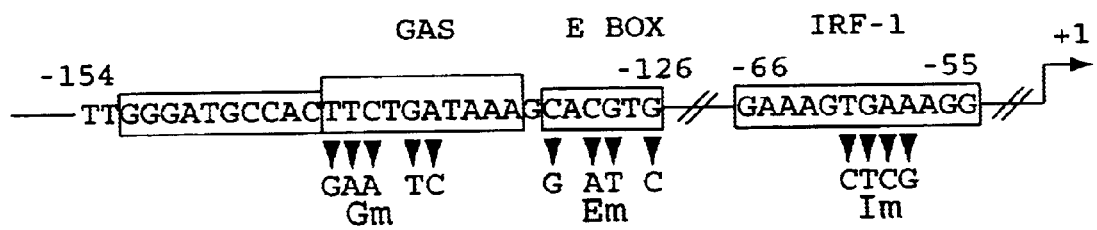

FIG. 8 depicts the organization of the IV wild-type and mutants human promoter IV. Sequences and positions of the conserved cis-acting elements are indicated. Ponctual mutations introduced in GAS element, E box and IRF-1 are shown below the wild-type sequence SEQ ID No. 29 with names of mutant constructs.

Figure 9:
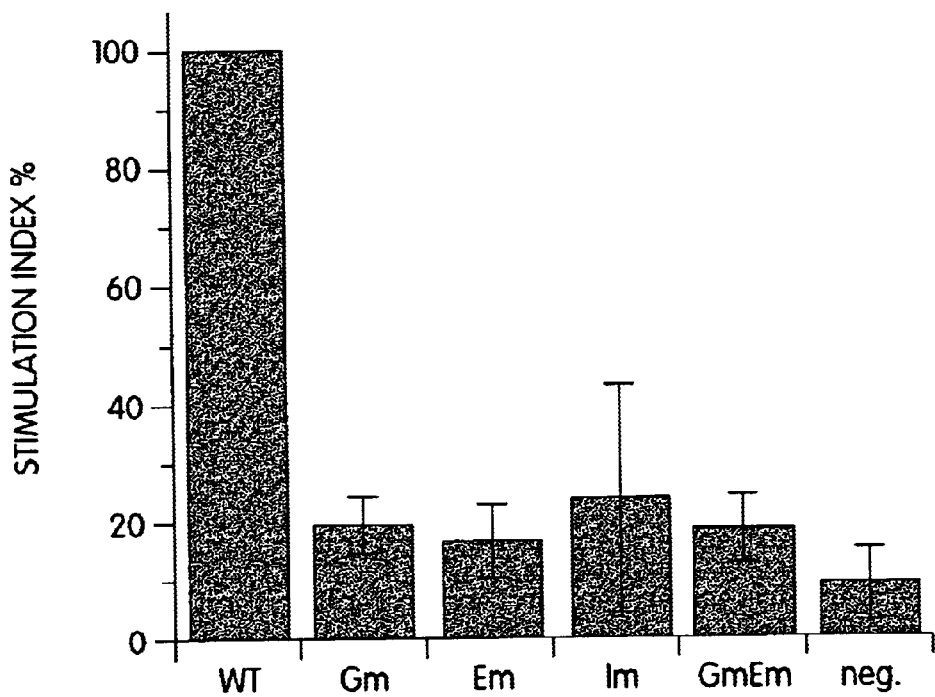

FIG. 9 depicts the functional analysis of wild-type and mutagenized Gm, Em and Im promoter IV. Stimulation index of the gene reporter expression is expressed in %. Plotted results are means of three independent experiments with standard deviations.

Figures 1, 2:
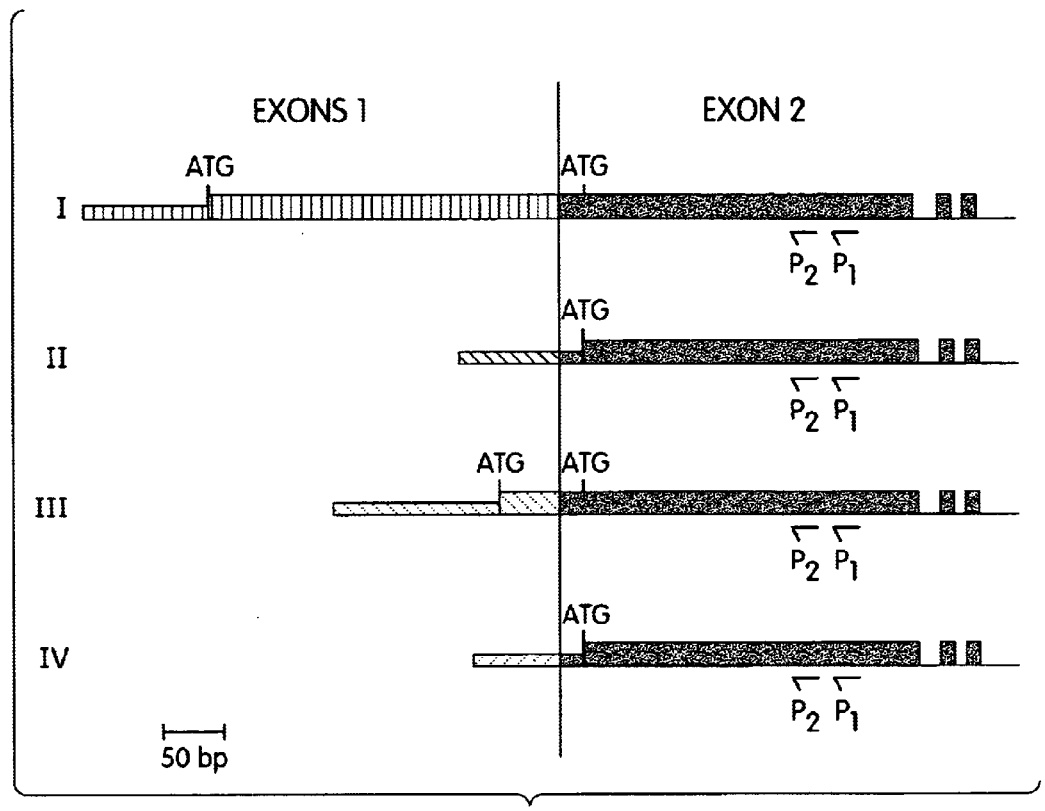
FIG. 2 shows the sequence, SEQ ID NO. 26 and the positions of the different sites for binding known transcription factors which were identified on the sequence, of the 5'-flanking region of the type I CIITA gene. The main transcription initiation site is also indicated by an arrow at +1.

The invention is also illustrated by the sequence identifiers SEQ ID No. 1 to SEQ ID No. 25, which sequence identifiers depict:

SEQ ID No. 1 to SEQ ID No. 3: the sequences of the three types of cDNA corresponding to the CIITA genes (sequences designated I, II and IV in FIG. 1), which were identified in accordance with the invention;

SEQ ID No. 4 to SEQ ID No. 6: the sequences which were identified as exhibiting a transcriptional promoter activity in the form I, form II and form IV CIITA genes and which were designated PI, PII and PIV, respectively;

SEQ ID No. 7 to SEQ ID No. 10: the sequences which correspond, respectively, to the different CIITA genes of forms I to IV, which genes lack the sequences which exhibit a transcriptional promoter activity;

SEQ ID No. 11: the sequence which corresponds to the coding part of the form I CIITA gene;

SEQ ID No. 12: the sequence which corresponds to the coding part of the form II CIITA gene;

SEQ ID No. 13: the sequence corresponding to the coding part of the form III CIITA gene;

SEQ ID No. 14: the sequence corresponding to the coding part of the form IV CIITA gene, including a untranslated part;

SEQ ID No. 15: a fragment of the SEQ ID No. 14 sequence, corresponding to nucleotides 901 to 3390, counting from the first nucleotide of SEQ ID No. 13;

SEQ ID No. 16: the translation of SEQ ID No. 11 into amino acids, corresponding to a form I CIITA factor which possesses 101 additional amino acids at the N-terminal end, as compared with SEQ ID No. 17;

SEQ ID No. 17: the translation into amino acids of the coding part of the form I to form IV CIITA genes, starting from an ATG located 21 bases downstream of the 5' end of the common exon 2 (FIG. 1);

SEQ ID No. 18: the translation of the form III CIITA gene into amino acids, starting from a second ATG, and corresponding to a CIITA factor which possesses 24 additional amino acids at the N-terminal end;

SEQ ID No. 19: the translation of SEQ ID No. 15 into amino acids

SEQ ID No. 20 to 25: PCR primers

EXAMPLES

Example 1

The cytoplasmic or total RNAs were extracted from various cell lines: Raji (Burkitt's lymphoma), Mann (human B lymphocyte), CEM (T lymphoblastoid line), THPA (monocyte), PP2 (fibroblast), Me67 (melanoma) after induction with interferon γ and HUVEC (human endothelial cell) using the technique described by Wilkinson (1988, Nucleic Acid Res. 16, 10933). The total RNA derived from the BC1 cell line (dendritic cells) was prepared using a Trizol-containing reagent (Gibco BRL). The RNAs derived from human spleen, thymus, tonsil and kidney were kindly provided by P. Sapino.

The 5' ends of the RNAs which were obtained were analysed by the RACE PCR technique (Frohman et al., 1988, Proc. Natl. Acad. Sci, USA, 85, 8998–9002) in accordance with the manufacturer's (Gibco BRL) instructions, with the following modifications. After reverse transcription of the RNAs, and before the amplification step, a dATP tail is added to the ends of the cDNAs. During the PCR amplification, 5 μl of isolated cDNA-dA are added to 40 μl of an amplification mixture containing 200 μM of each of the dNTPs and 25 pmol of primers which are specific for the gene encoding the CIITA factor, i.e. P1 (5'-GGTCCAGTTCCGCGATATTGG-3') SEQ ID NO. 20 and P2 (5'-TCCCTGGTCTCTTCATCA-3'), SEQ ID No. 21 25 pmol of adaptation primer ADXSC (5'-GACTCGAGTCGACATCG-3') SEQ ID No. 22 and 10 pmol of adaptation primer XSCT17 (5'-GACTCGAGTCGACATCGAT-3') SEQ ID NO. 23. After a preincubation at 95° C. for 5 minutes, 2 units of Taq polymerase are added and the amplification is carried out in 30 cycles of 45 seconds at 94° C., 25 seconds at 54° C. and 2 minutes at 72° C. The final incubation is carried out at 72° C. for 10 minutes.

These amplifications demonstrated the existence of four types of cDNA which corresponded to the CIITA factor. Analysis of the sequences of these nucleic acids showed that while these nucleic acids all possessed a common 3' end (Exon 2), they diverged completely at their 5' ends, thereby defining four different types of Exon 1. These four sequences (variable Exon 1+ common Exon 2) are identified as I, II, III and IV (FIG. 1).

As the analysis of the sequences indicates, these four transcripts, i.e., I, II, III and IV, exhibit a common reading frame which begins at the ATG which is located 21 bases downstream of the 5' end of the common Exon 2 (FIG. 1). In the case of sequences II and IV, this ATG is the first initiation codon. In the case of sequences I and III, another ATG exists which leads to the synthesis of a CIITA factor which possesses 101 or 24 additional amino acids, respectively, at the N-terminal end of the translated polypeptide.

Example 2

The sites for initiating transcription of the different human CIITA mRNAs which had been identified were tested by means of RNAse protection using DNA fragments which were specific for the different Exons 1.

In the case of the type I transcripts, three protected fragments were identified using nucleic acid which was isolated from liver. The major fragment corresponds to the transcription initiation site which is located 380 bases upstream of the 3' end of Exon 1 (FIG. 1). This site was defined as nucleotide +1 of the type I mRNAs. The two other transcripts are obtained from initiation sites which were located in positions −14 and +8. The locations of these initiation sites are compatible with the use, during translation, of the ATG signals identified in Example 1.

In the case of the type III transcripts, several protected fragments were identified using nucleic acid which was isolated from B lymphocytes. The major transcript corresponds to an initiation which starts from the position 183 bases upstream of the 3' end of Exon 1 and defines position +1 of the type III transcripts. Two other initiation sites are located at positions −8 and −4. Other minor sites are identified in positions −23 and +34. These initiation sites are compatible with the use of the two ATG sites located in Example 1.

In the case of the type IV transcripts, a large number of protected fragments were identified using nucleic acids which were isolated from melanoma cells which were induced with interferon γ. The major transcript corresponds to a transcription initiation which is located 75 bases upstream of the 3' end of Exon 1, which site defines position +1 of the type IV transcripts. A second major initiation site is observed at position +17, as well as six minor sites which are located between positions −54 and +69 of Exon 1. These initiation sites are compatible with the use of the ATG which is located 21 bases downstream of the 5' end of Exon 2 (Example 1).

The presence of distinct initiation sites for each of the I, II, III and IV RNAs suggests that the promoter regions which control expression of the corresponding genes are distinct (designated PI, PII, PIII and PIV).

Example 3

Having identified the sequence divergences which were observed at the 5' ends of the mRNAs (Exon 1 and untranslated sequence), the applicant then isolated the genomic sequences, including the promoter regions, of genes I, II, III and IV from a λ phage library containing the human genome.

Comparison of the sequences corresponding to the four promoters PI, PII, PIII and PIV does not demonstrate any significant homology. None of these regions contains a GC or TATA box. This latter observation explains the substantial number of initiation sites which were observed for a given transcript.

By contrast, it was possible to identify several sites corresponding to sites for binding elements which act in cis during the transcription of other genes. Thus, promoter PI contains an NF-GMb site, an NF-IL6 site, two inverted NF-IL6 sites, a PEA3 site, and a PEA3 site in the opposite direction, an AP1 site and a CCAAT box (FIG. 2). Similarly, promoter PIII contains an E2A box in the opposite direction, an IRF1/2 site, an MYC site in the opposite direction and an OCT site in the opposite direction (FIG. 3). An NF-GMa site, a GAS box, an E box, a IRF1/2 site and an NfKB site are found in promoter IV (FIG. 4).

Example 4

In order to study the expression profile of these different genes in various cell types, four cDNA fragments which were specific for each of the mRNA forms were prepared as RNAse protection probes. These probes are depicted in FIG. 5. Use is made of an internal control which makes it possible to evaluate the total expression of the CIITA-encoding genes (from nucleotide 1152, PstI site, to nucleotide 1344, NcoI site, protecting 193 bases of the region possessed in common by the RNAs (Exon 2)). The RNAse protection tests are carried out on 25 μg of RNA as previously described (Steimle et al., 1993, Cell, 75, 135–146). The results are quantified by using a PhosphorImager. The promoter function is quantified as being the ratio of the expression of a specific type of mRNA as compared with the total expression of the CIITA-encoding genes measured using the internal control.

An analysis was carried out of the mRNAs which were derived from different tissues or cell lines which were expressing the CIITA gene either constitutively or following induction with interferon γ.

The results (Table 1 and FIG. 6) show that differential use of the PI, PII, PIII and PIV promoters occurs. Thus, it was shown that the type I mRNAs, which result from using PI, are very strongly expressed in dendritic cells (FIG. 6), more weakly expressed in the spleen and thymus, and not expressed at all in the other tissues or cell lines.

The type III mRNAs are detected at a high level in different B lymphocyte cell lines as well as in tissues which are rich in B lymphocytes, such as the spleen and the tonsils, or the thymus (FIG. 6). By contrast, these type III mRNAs are very weakly expressed in dendritic cells or in cells which can be induced with interferon γ (Me67.1, THP1, HUVEC and PP2).

The type IV mRNAs are the form which is principally expressed following induction with interferon A. That this was the case was observed in a variety of inducible cell lines such as Me67.1 (melanoma), THP1 (monocyte), HUVEC (endothelial cells) and PP2 (fibroblasts). By contrast, these mRNAs are only weakly expressed in B lymphocytes or dendritic cells (FIG. 5).

Example 5

The functional activity and the tissue specificity of the PIII and PIV promoters were analysed by transfecting cells with constructs which combined a reporter gene and a promoter. Given the fact that the type III mRNAs are mainly expressed in B lymphocytes and that the type IV mRNAs are preferentially expressed in cells which can be induced with interferon γ, the test cell lines selected are the Raji (B lymphocyte) and Me67.8 (melanoma) cell lines. The reporter gene which is selected is the gene which encodes rabbit β globin. The promoter region to be tested is cloned upstream of this gene into plasmid PGβG(+) (Sperisen et al., 1992, PCR. Methods Appl. 1, 164–170). The plasmids pIII-974 and pIII-322 contain the −974 (NheI)/+101 (HpaII) and −322 (PstI)/+101 (HpaII) fragments, respectively, of the genome regions which are located 5' of the type III Exon 1. Plasmids pIV-950 and pIV-461 contain the −950 (XhoI)/+75 and −461 (KpnI)/+75 fragments, respectively, of the genome regions located 5' of the type IV Exon 1. A reference plasmid is also used as a control: this is a plasmid which contains a gene encoding rabbit β globin which possesses a deletion of 40 bases and which is transcribed under the control of a constitutive chicken promoter (pGβAcβGID, Sperisen et al., 1992). Expression of the reporter gene is measured by quantitative RT-PCR as described in Sperisen et al., 1992 with the following modifications. $5 \times 10^6$ Raji cells and $2.5 \times 10^6$ Me67.8 cells were transfected, by electroporation at 250V and 960 μF (GenePulse, BioRad), with 20 μg of a plasmid preparation, which consisted of a defined ratio of the plasmid as previously described and the reference plasmid, and 400 μg of E. Coli tRNA, as the carrier molecule, in 750 μl of RPMI buffer. For the step of induction with interferon γ, the cell cultures are placed, following transformation, in the presence (500U/ml) or absence of the inducer. The cells are cultured at 37° C. for 48 hours. The total RNAs are extracted with the Triazol-containing reagent and digested with RNAse-free DNAseI (Boehringer). 1 μg of total RNA is used for carrying out the reverse transcription in the presence of a primer $(dT)_{20}$ and RNAse-free Superscript (50U, GIBCO BRL) reverse transcriptase and 10U of RNAse inhibitor. Subsequently, 1/10 of the cDNA which has been obtained is amplified using the primers βGP5' (5'-TCCCCCAAAACAGACAGAATGG-3') SEQ ID No. 24 (40 pmol) and βGP3' (5'-GTCACAGTGCAGTTCACTCAG-3') SEQ ID No. 25 (40 pmol) in a 50 μl volume containing 5 μl of 10×Vent buffer in the presence of 2 μCi of $(\alpha^{32}P)dCTP$ (Amersham). After preincubating at 95° C. for 3 minutes, 2U of Vent DNA polymerase (NEB) are added. The amplification is carried out in 30 cycles of 40 seconds at 94° C., 30 seconds at 59° C. and 60 seconds at 72° C. The PCR products are denatured and loaded onto a denaturing polyacrylamide gel (6%, 8M urea). The signals are quantified using the PhosphoImager.

The results obtained show that while transfection of B lymphocytes with plasmid pIII-974 and pIII-322 is accompanied by strong activity of the pIII promoter, the same promoters are inactive in Me67.8 cells before or after induction. It is furthermore observed that pIII-322 is expressed better than plasmid pIII-974 in the B lymphocytes.

By contrast, when plasmids pIV-950 and pIV-461 are used, only basal expression is observed in the B lymphocytes whereas very strong expression is observed in the induced Me67.8 cells and in other types of induced cells (Hela or 2FTGH). Moreover, the expression signals of these two plasmids pIV-950 and pIV-461 have values of 0.13 and 0.18, respectively, before induction and of 7.9 and 29.6, respectively, following induction with interferon.

TABLE 1

Percentages of the different types of CIITA mRNA observed in various tissues and cell lines.

|  | TYPE I | TYPE III | TYPE IV |
|---|---|---|---|
| Spleen | 3.5% | 67% | 33% |
| Tonsil | 0% | 96% | 17% |
| Thymus | 6% | 60% | 33% |
| Raji | 0% | 86% | 2.5% |
| Mann | 0% | 72% | 17% |
| Dendr. | 74% | 39% | 2.7% |
| Me67.1 + IFN-γ | 0% | 2% | 88% |
| THP1 + IFN-γ | 0% | 14% | 62% |
| HUVEC + IFN-γ | n.d. | 10% | 68% |
| PP2 + IFN-γ | n.d. | 16% | 66% |

Example 6

As shown in FIG. 4, SEQ ID No. 6, corresponding to cytokine inducible CIITA promoter IV, contains at least 3 potential cis-acting elements which could be involved in transcription regulation of a gene located downstream of the said sequence. These elements are GAS element, E box and IRF-1 binding site.

In order to analyse the functional relevance of these cis-acting elements, site directed mutagenesis was performed. A reporter gene has been constructed. This plasmid contains the −308 to +75 fragment of SEQ ID No. 6 subcloned upstream of the rabbit β-globin gene of plasmid pGβG(+). Directed mutagenesis was performed introducing many ponctual mutations in sequences to be analysed in the said plasmid (see FIG. 8) leading to 3 mutants named Gm, Em and Im corresponding to mutations in GAS element, E box and IRF-1, respectively.

Reporter gene (wild type and each of the mutated plasmids) expression was measured after gamma interferon activation, in cell line Me67.8 (melanoma cell line) by quantitative RT-PCR (Sperisen et al., 1992, PCR. Meth. Appli., 1, 164–170). Transfections, induction, RNA preparation and RT-PCR analyses were performed as previously described (Muhlenthaler-Motter et al., 1997, EMBO J., 16, 2851–2860).

Transfections of the wild-type plasmid in the melanoma cell line Me67.8, without gamma interferon activation, showed a very low basal transcriptional activity of the β-globin reporter gene (not shown). Treatment of these transfected cells with gamma interferon induced a very high expression of the β-globulin gene showing a strong activity of promoter IV (the activity was referred as 100% of stimulation index).

Similarly, β-globin reporter gene expression directed by mutated sequences (Gm, Em and Im) was analysed. Results (FIG. 9) showed that mutations in either the GAS element (Gm), the E-box (Em) or IRF-1 (Im) of SEQ ID No. 6 resulted in an almost complete abolition of promoter inducibility by gamma interferon, with stimulation index equivalent to 19%, 16% and 23% of wild-type stimulation index, respectively. The same reduction of promoter responsiveness to gamma interferon was observed with a double mutant GmEm (GAS element and E-box) leading to 17% of the wild-type stimulation index.

These results show that each of these cis-acting elements are functionally relevant for gamma interferon stimulation of expression of gene located downstream of promoter IV.

Example 7

Since we have demonstrated the functional importance of the IRF-1 binding site of promoter IV and since IRF-1 was shown to be involved in the induction of several interferon gamma inducible genes, such as for example GBP (Briken et al., 1995, Mol. Cell. Biol., 15, 975–982), we investigated the role of IRF-1 in the induction of CIITA by interferon gamma. RNAs from embryonic fibroblasts (EF) derived from wild-type (wt) and from IRF-1⁻ mice (which do not express IRF-1) were compared for CIITA mRNA expression stimulation by interferon gamma. RNAse protection assays revealed that, in contrast to wild-type EF, interferon gamma induced CIITA mRNA expression was strongly reduced in IRF-1⁻ EF. The same inhibition of interferon gamma stimulation was observed for GBP mRNA. The results indicate that IRF-1 is an essential factor for induction efficiency by interferon gamma.

What is claimed is:

1. A nucleic acid sequence which comprises all or part of a nucleic acid sequence of a CIITA gene and which is selected from the sequences SEQ ID No. 1, SEQ ID No. 2 and SEQ ID No. 3, and their complementary sequences.

2. The nucleic acid sequence according to claim 1, wherein said sequence comprises all or part of a nucleic acid sequence which exhibits a transcriptional promoter activity.

3. The nucleic acid sequence according to claim 2, wherein said promoter activity is specifically expressed in one cell type selected from the group consisting of β lymphocytes, T lymphocytes, macrophages, cells of thymic epithelium, dendritic cells, monocytes, endothelial cells, fibroblasts, muscle cells and cancer cells.

4. The nucleic acid sequence according to claim 3, wherein said cell is a dendritic cell.

5. The nucleic acid sequence according to claim 2, wherein said promoter activity is specifically induced by a cytokine.

6. The nucleic acid sequence according to claim 5, wherein said cytokine is selected from the group consisting of interferon γ and interleukin 4.

7. A nucleic acid sequence which comprises the sequence SEQ ID NO.:4, or its complementary sequence.

8. A nucleic acid sequence which comprises the sequence SEQ ID NO.:6, or its complementary sequence.

9. The nucleic acid sequence according to claim 7, wherein said sequence exhibits a transcriptional promoter activity.

10. The nucleic acid sequence according to claim 8, wherein said sequence exhibits a transcriptional promoter activity.

11. A nucleic acid sequence consisting of:
    a) a nucleic acid sequence of SEQ ID No.5; or
    b) the complementary sequence of SEQ ID No. 5:
and which exhibits a transcriptional promoter activity.

12. The nucleic acid sequence according to any one of claims 9, 10 and 11, wherein said promoter activity is specifically expressed in one cell type selected from B lymphocytes, T lymphocytes, macrophages, cells of thymic epithelium, dendritic cells, monocytes, endothelial cells, fibroblasts, muscle cells and cancer cells.

13. The nucleic acid sequence according to claim 12 wherein said promoter activity is specifically expressed in a dendritic cell.

14. The nucleic acid sequence according to any one of claim 9, 10 or 11, wherein said promoter activity is specifically induced by a cytokine.

15. The nucleic acid sequence according to claim 14 wherein said cytokine is selected from the group consisting of interferon γ and interleukin 4.

16. A nucleic acid sequence comprising:
   a) one sequence according to any one of claim 9, 10 or 11, and
   b) one sequence comprising at least any one of the SEQ ID NO: 9, SEQ ID NO: 12, SEQ ID NO: 13, SEQ ID NO: 14 and SEQ ID NO: 15, and their complementary sequence,
   wherein the sequence in a) is located upstream of the sequence in b).

17. A nucleic acid sequence which comprises a sequence selected from:
   a) a nucleic acid sequence which encodes a CIITA polypeptide which consists of the amino acids defined in accordance with SEQ ID NO.:16, and its complementary sequence,
   b) the sequences SEQ ID NO.:7, SEQ ID NO.:8, SEQ ID NO.:10, and SEQ ID NO.:11 and their complementary sequences,
   c) a nucleic acid sequence which encodes an allelic variant of a CIITA polypeptide defined in a).

18. A method for detecting a mutation in CIITA genes comprising:
   obtaining a biological sample from a patient;
   detecting the presence of at least one mutation in CIITA genes by analyzing nucleic acid sequence in the sample and comparing said nucleic acid sequence from the patient with the wild type sequences SEQ ID NO.:1, SEQ ID NO.:2 and SEQ ID NO.:3.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 5463 base pairs
      (B) TYPE: nucleic acid
      (C) STRANDEDNESS: single
      (D) TOPOLOGY: linear (ii) MOLECULE TYPE: DNA (genomic)

(ix) FEATURE:
    (A) NAME/KEY: cIIta gene of type I (xi) SEQUENCE DESCRIPTION: SEQ ID NO: 1:

```
GTAAGTACTG TAACAGAGAC TAAATGCTAA GTAAGGCAGG CGTGGTGGCT CACACTTGTA      60
ATCCCAGTAC TTTGGAGGAC TGAGGCAAGA GGATCACTTG AGCCCAGAAT TCAAGACCAG     120
CCTGGGAAAC AGAGTGAGAC CCTGTCTCTA CTAAAAATAA AAAAATAAAA AATTAGCGGG     180
GCATGATGGT GTGAGTCTGT AGTCCCAGCT ACTGGGAAAC AGAGATGGGA GGTTTGTTTG     240
AGCCTGGGAA GTTGAGGCTG CAGTGAGTTA TGATCACGCC ACTGCACACC AGCCTGGGCA     300
ACAGAGCAAG ACCCTGTCAA AAAAAAAAAA AAGGCTATGT AACACCCCCA AGTCACATAA     360
TTGGCAAGGA GCAGCAGATC TGGGACTTGA ACATAGGCAG ATTAGCTCCA AGCCTATTTG     420
CTTAACCTCT ATACCACAAT GCCTTCTTGC TATGGTAAAA CATCTGAAAA GACCTATTAC     480
CCTATAGGTC CTCTAAGGAG GCATGTCGCC TTCCTCTTAG CAATACTAGA TTGGCTCCAA     540
CAGAAGGCTG TGGGCTTCTC TGGCACATGC ACCTGGGTAG ACCCAGAGA ATATCTGTGG      600
AGTCTGAATC AACCCAAAAG CCAATATCCA TCCGTTCATC AGGAACCCCA GCCTACAACG     660
CAAAAGAGGA AATCTTCCTA AGTAGAAATA AACTGTAATA AATTGCAGAG GTTCCCTCGT     720
CCTGGTTTTC ACTTCATGTT TTGGATGCTG CATGCTGGGT GAGCGGAGAT TCCAGGCACT     780
GGCCAGGGCA GCTGCCCTGA CTCCAAGGGC TGCCATGAAC AACTTCCAGG CCATCCTGAC     840
TCAGGTGAGA ATGCTGCTCT CCAGCCATCA GCCCAGCCTG GTGCAGGCCC TCTTGGACAA     900
CCTGCTGAAG GAGGACCTCC TCTCCAGGGA ATACCACTGC ACTCTGCTCC ATGAGCCTGA     960
TAGTGAGGCT CTGGCCAGGA AGATCTCTTT GACCCTACTA GAGAAAGGAG ACCTGGATTT    1020
GGCCCTCCTG GGGTGGGCCC GGAGTGGGCT GCAGCCCCCA GCAGCCGAGA GGGGCCCCGG    1080
CCACAGTGAC CATGGTGGCA GCTCACAGTG TGCCACCATG GAGTTGGGGC CCCTAGAAGG    1140
TGGCTACCTG GAGCTTCTTA ACAGCGATGC TGACCCCCTG TGCCTCTACC ACTTCTATGA    1200
CCAGATGGAC CTGGCTGGAG AAGAAGAGAT TGAGCTCTAC TCAGAACCCG ACACAGACAC    1260
CATCAACTGC GACCAGTTCA GCAGGCTGTT GTGTGACATG GAAGGTGATG AAGAGACCAG    1320
GGAGGCTTAT GCCAATATCG CGGAACTGGA CCAGTATGTC TTCCAGGACT CCCAGCTGGA    1380
GGGCCTGAGC AAGGACATTT TCAAGCACAT AGGACCAGAT GAAGTGATCG GTGAGAGTAT    1440
GGAGATGCCA GCAGAAGTTG GCAGAAAAG TCAGAAAAGA CCCTTCCCAG AGGAGCTTCC     1500
GGCAGACCTG AAGCACTGGA AGCCAGCTGA GCCCCCCACT GTGGTGACTG GCAGTCTCCT    1560
AGTGGGACCA GTGAGCGACT GCTCCACCCT GCCCTGCCTG CCACTGCCTG CGCTGTTCAA    1620
CCAGGAGCCA GCCTCCGGCC AGATGCGCCT GGAGAAAACC GACCAGATTC CCATGCCTTT    1680
CTCCAGTTCC TCGTTGAGCT GCCTGAATCT CCCTGAGGGA CCCATCCAGT TTGTCCCCAC    1740
CATCTCCACT CTGCCCCATG GCTCTGGCA AATCTCTGAG GCTGGAACAG GGTCTCCAG     1800
TATATTCATC TACCATGGTG AGGTGCCCCA GGCCAGCCAA GTACCCCCTC CCAGTGGATT    1860
CACTGTCCAC GGCCTCCCAA CATCTCCAGA CCGGCCAGGC TCCACCAGCC CCTTCGCTCC    1920
ATCAGCCACT GACCTGCCCA GCATGCCTGA ACCTGCCCTG ACCTCCCGAG CAAACATGAC    1980
AGAGCACAAG ACGTCCCCCA CCCAATGCCC GGCAGCTGGA GAGGTCTCCA ACAAGCTTCC    2040
AAAATGGCCT GAGCCGGTGG AGCAGTTCTA CCGCTCACTG CAGGACACGT ATGGTGCCGA    2100
GCCCGCAGGC CCGGATGGCA TCCTAGTGGA GGTGGATCTG GTGCAGGCCA GGCTGGAGAG    2160
GAGCAGCAGC AAGAGCCTGG AGCGGGAACT GGCCACCCCG GACTGGGCAG AACGGCAGCT    2220
```

-continued

```
GGCCCAAGGA GGCCTGGCTG AGGTGCTGTT GGCTGCCAAG GAGCACCGGC GGCCGCGTGA    2280

GACACGAGTG ATTGCTGTGC TGGGCAAAGC TGGTCAGGGC AAGAGCTATT GGGCTGGGGC    2340

AGTGAGCCGG GCCTGGGCTT GTGGCCGGCT TCCCCAGTAC GACTTTGTCT TCTCTGTCCC    2400

CTGCCATTGC TTGAACCGTC CGGGGGATGC CTATGGCCTG CAGGATCGCA TCTTCTCCCT    2460

GGGCCCACAG CCACTCGTGG CGGCCGATGA GGTTTTCAGC CACATCTTGA AGAGACCTGA    2520

CCGCGTTCTG CTCATCCTAG ACGCCTTCGA GGAGCTGGAA GCGCAAGATG GCTTCCTGCA    2580

CAGCACGTGC GGACCGGCAC CGGCGGAGCC CTGCTCCCTC CGGGGGCTGC TGGCCGGCCT    2640

TTTCCAGAAG AAGCTGCTCC GAGGTTGCAC CCTCCTCCTC ACAGCCCGGC CCGGGGCCG     2700

CCTGGTCCAG AGCCTGAGCA AGGCCGACGC CCTATTTGAG CTGTCCGGCT TCTCCATGGA    2760

GCAGGCCCAG GCATACGTGA TGCGCTACTT TGAGAGCTCA GGGATGACAG AGCACCAAGA    2820

CAGAGCCCTG ACGCTCCTCC GGGACCGGCC ACTTCTTCTC AGTCACAGCC ACAGCCCTAC    2880

TTTGTGCCGG GCAGTGTGCC AGCTCTCAGA GGCCCTGCTG GAGCTTGGGG AGGACGCCAA    2940

GCTGCCCTCC ACGCTCACGG GACTCTATGT CGGCCTGCTG GGCCGTGCAG CCCTCGACAG    3000

CCCCCCCGGG GCCCTGGCAG AGCTGGCCAA GCTGGCCTGG GAGCTGGGCC GCAGACATCA    3060

AAGTACCCTA CAGGAGGACC AGTTCCCATC CGCAGACGTG AGGACCTGGG CGATGGCCAA    3120

AGGCTTAGTC CAACACCCAC CGCGGGCCGC AGAGTCCGAG CTGGCCTTCC CCAGCTTCCT    3180

CCTGCAATGC TTCCTGGGGG CCCTGTGGCT GGCTCTGAGT GGCGAAATCA AGGACAAGGA    3240

GCTCCCGCAG TACCTAGCAT TGACCCCAAG GAAGAAGAGG CCCTATGACA ACTGGCTGGA    3300

GGGCGTGCCA CGCTTTCTGG CTGGGCTGAT CTTCCAGCCT CCCGCCCGCT GCCTGGGAGC    3360

CCTACTCGGG CCATCGGCGG CTGCCTCGGT GGACAGGAAG CAGAAGGTGC TTGCGAGGTA    3420

CCTGAAGCGC CTGCAGCCGG GGACACTGCG GGCGCGGCAG CTGCTTGAGC TGCTGCACTG    3480

CGCCCACGAG GCCGAGGAGG CTGGAATTTG GCAGCACGTG GTACAGGAGC TCCCCGGCCG    3540

CCTCTCTTTT CTGGGCACCC GCCTCACGCC TCCTGATGCA CATGTACTGG GCAAGGCCTT    3600

GGAGGCGGCG GGCCAAGACT TCTCCCTGGA CCTCCGCAGC ACTGGCATTT GCCCCTCTGG    3660

ATTGGGGAGC CTCGTGGGAC TCAGCTGTGT CACCCGTTTC AGGGCTGCCT TGAGCGACAC    3720

GGTGGCGCTG TGGGAGTCCC TGCGGCAGCA TGGGGAGACC AAGCTACTTC AGGCAGCAGA    3780

GGAGAAGTTC ACCATCGAGC CTTTCAAAGC CAAGTCCCTG AAGGATGTGG AAGACCTGGG    3840

AAAGCTTGTG CAGACTCAGA GGACGAGAAG TTCCTCGGAA GACACAGCTG GGGAGCTCCC    3900

TGCTGTTCGG GACCTAAAGA AACTGGAGTT TGCGCTGGGC CCTGTCTCAG GCCCCCAGGC    3960

TTTCCCCAAA CTGGTGCGGA TCCTCACGGC CTTTTCCTCC CTGCAGCATC TGGACCTGGA    4020

TGCGCTGAGT GAGAACAAGA TCGGGGACGA GGGTGTCTCG CAGCTCTCAG CCACCTTCCC    4080

CCAGCTGAAG TCCTTGGAAA CCCTCAATCT GTCCCAGAAC AACATCACTG ACCTGGGTGC    4140

CTACAAACTC GCCGAGGCCC TGCCTTCGCT CGCTGCATCC CTGCTCAGGC TAAGCTTGTA    4200

CAATAACTGC ATCTGCGACG TGGGAGCCGA GAGCTTGGCT CGTGTGCTTC CGGACATGGT    4260

GTCCCTCCGG GTGATGGACG CAAGTTCACG GCTGCCGGGG CCCAGCAGCT CGCTGCCAGC    4320

CTTCGGAGGT GTCCTCATGT GGAGACGCTG GCGATGTGGA CGCCCACCAT CCCATTCAGT    4380

GTCCAGGAAC ACCTGCAACA ACAGGATTCA CGGATCAGCC TGAGATGATC CCAGCTGTGC    4440

TCTGGACAGG CATGTTCTCT GAGGACACTA ACCACGCTGG ACCTTGAACT GGGTACTTGT    4500

GGACACAGCT CTTCTCCAGG CTGTATCCCA TGAGGCCTCA GCATCCTGGC ACCCGGCCCC    4560
```

```
TGCTGGTTCA GGGTTGGCCC CTGCCCGGCT GCGGAATGAA CCACATCTTG CTCTGCTGAC    4620

AGACACAGGC CCGGCTCCAG GCTCCTTTAG CGCCCAGTTG GGTGGATGCC TGGTGGCAGC    4680

TGCGGTCCAC CCAGGAGCCC CGAGGCCTTC TCTGAAGGAC ATTGCGGACA GCCACGGCCA    4740

GGCCAGAGGG AGTGACAGAG GCAGCCCCAT TCTGCCTGCC CAGGCCCCTG CCACCCTGGG    4800

GAGAAAGTAC TTCTTTTTTT TTATTTTTAG ACAGAGTCTC ACTGTTGCCC AGGCTGGCGT    4860

GCAGTGGTGC GATCTGGGTT CACTGCAACC TCCGCCTCTT GGGTTCAAGC GATTCTTCTG    4920

CTTCAGCCTC CCGAGTAGCT GGGACTACAG GCACCCACCA TCATGTCTGG CTAATTTTTC    4980

ATTTTTAGTA GAGACAGGGT TTTGCCATGT TGGCCAGGCT GGTCTCAAAC TCTTGACCTC    5040

AGGTGATCCA CCCACCTCAG CCTCCCAAAG TGCTGGGGAT TACAAGCGTG AGCCACTGCA    5100

CCGGGCCACA GAGAAAGTAC TTCTCCACCC TGCTCTCCGA CCAGACACCT TGACAGGGCA    5160

CACCGGGCAC TCAGAAGACA CTGATGGGCA ACCCCCAGCC TGCTAATTCC CCAGATTGCA    5220

ACAGGCTGGG CTTCAGTGGC AGGCTGCTTT TGTCTATGGG ACTCAATGCA CTGACATTGT    5280

TGGCCAAAGC CAAAGCTAGG CCTGGCCAGA TGCACCAGGC CCTTAGCAGG GAAACAGCTA    5340

ATGGGACACT AATGGGCGG TGAGAGGGGA ACAGACTGGA AGCACAGCTT CATTTCCTGT    5400

GTCTTTTTTC ACTACATTAT AAATGTCTCT TTAATGTCAC AAAAAAAAAA AAAAAAAAA    5460

AAA                                                                  5463

(2) INFORMATION FOR SEQ ID NO: 2:

(i) SEQUENCE CHARACTERISTICS:
        (A) LENGTH: 4564 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: cIIta gene of type II (xi) SEQUENCE DESCRIPTION: SEQ ID NO: 2:

CCCGGGCGCC CCGCCTCAGT TTCCCCATCT ATAAAGTGGA GATGATAATA GCATTCAGAG      60

TCACTGATCT AAGGGCTCAG GGACACCATT CAGTGTAAGC CCCATACACT CCCTGCAAGA     120

GGAAGCTGGT TCTGACTCAG CCTTGAGGCT GGCGTCTGAG GCAACCACAA GCCCAACGTG     180

CATGGTGGAA AGATGACTGC AGCTCACAGT GTGCCACCAT GGAGTTGGGG CCCCTAGAAG     240

GTGGCTACCT GGAGCTTCTT AACAGCGATG CTGACCCCCT GTGCCTCTAC CACTTCTATG     300

ACCAGATGGA CCTGGCTGGA GAAGAAGAGA TTGAGCTCTA CTCAGAACCC GACACAGACA     360

CCATCAACTG CGACCAGTTC AGCAGGCTGT TGTGTGACAT GGAAGGTGAT GAAGAGACCA     420

GGGAGGCTTA TGCCAATATC GCGGAACTGG ACCAGTATGT CTTCCAGGAC TCCCAGCTGG     480

AGGGCCTGAG CAAGGACATT TTCAAGCACA TAGGACCAGA TGAAGTGATC GGTGAGAGTA     540

TGGAGATGCC AGCAGAAGTT GGGCAGAAAA GTCAGAAAAG ACCCTTCCCA GAGGAGCTTC     600

CGGCAGACCT GAAGCACTGG AAGCCAGCTG AGCCCCCCAC TGTGGTGACT GGCAGTCTCC     660

TAGTGGGACC AGTGAGCGAC TGCTCCACCC TGCCCTGCCT GCCACTGCCT GCGCTGTTCA     720

ACCAGGAGCC AGCCTCCGGC CAGATGCGCC TGGAGAAAAC CGACCAGATT CCCATGCCTT     780

TCTCCAGTTC CTCGTTGAGC TGCCTGAATC TCCCTGAGGG ACCCATCCAG TTTGTCCCCA     840

CCATCTCCAC TCTGCCCCAT GGGCTCTGGC AAATCTCTGA GGCTGGAACA GGGGTCTCCA     900

GTATATTCAT CTACCATGGT GAGGTGCCCC AGGCCAGCCA AGTACCCCCT CCCAGTGGAT     960
```

```
TCACTGTCCA CGGCCTCCCA ACATCTCCAG ACCGGCCAGG CTCCACCAGC CCCTTCGCTC    1020

CATCAGCCAC TGACCTGCCC AGCATGCCTG AACCTGCCCT GACCTCCCGA GCAAACATGA    1080

CAGAGCACAA GACGTCCCCC ACCCAATGCC CGGCAGCTGG AGAGGTCTCC AACAAGCTTC    1140

CAAAATGGCC TGAGCCGGTG GAGCAGTTCT ACCGCTCACT GCAGGACACG TATGGTGCCG    1200

AGCCCGCAGG CCCGGATGGC ATCCTAGTGG AGGTGGATCT GGTGCAGGCC AGGCTGGAGA    1260

GGAGCAGCAG CAAGAGCCTG GAGCGGGAAC TGGCCACCCC GGACTGGGCA GAACGGCAGC    1320

TGGCCCAAGG AGGCCTGGCT GAGGTGCTGT TGGCTGCCAA GGAGCACCGG CGGCCGCGTG    1380

AGACACGAGT GATTGCTGTG CTGGGCAAAG CTGGTCAGGG CAAGAGCTAT TGGGCTGGGG    1440

CAGTGAGCCG GGCCTGGGCT TGTGGCCGGC TTCCCCAGTA CGACTTTGTC TTCTCTGTCC    1500

CCTGCCATTG CTTGAACCGT CCGGGGGATG CCTATGGCCT GCAGGATCTG CTCTTCTCCC    1560

TGGGCCCACA GCCACTCGTG GCGGCCGATG AGGTTTTCAG CCACATCTTG AAGAGACCTG    1620

ACCGCGTTCT GCTCATCCTA GACGCCTTCG AGGAGCTGGA AGCGCAAGAT GGCTTCCTGC    1680

ACAGCACGTG CGGACCGGCA CCGGCGGAGC CCTGCTCCCT CCGGGGCTG CTGGCCGGCC    1740

TTTTCCAGAA GAAGCTGCTC CGAGGTTGCA CCCTCCTCCT CACAGCCCGG CCCCGGGGCC    1800

GCCTGGTCCA GAGCCTGAGC AAGGCCGACG CCCTATTTGA GCTGTCCGGC TTCTCCATGG    1860

AGCAGGCCCA GGCATACGTG ATGCGCTACT TTGAGAGCTC AGGGATGACA GAGCACCAAG    1920

ACAGAGCCCT GACGCTCCTC CGGGACCGGC CACTTCTTCT CAGTCACAGC CACAGCCCTA    1980

CTTTGTGCCG GGCAGTGTGC CAGCTCTCAG AGGCCCTGCT GGAGCTTGGG GAGGACGCCA    2040

AGCTGCCCTC CACGCTCACG GGACTCTATG TCGGCCTGCT GGGCCGTGCA GCCCTCGACA    2100

GCCCCCCCGG GGCCCTGGCA GAGCTGGCCA AGCTGGCCTG GGAGCTGGGC CGCAGACATC    2160

AAAGTACCCT ACAGGAGGAC CAGTTCCCAT CCGCAGACGT GAGGACCTGG GCGATGGCCA    2220

AAGGCTTAGT CCAACACCCA CCGCGGGCCG CAGAGTCCGA GCTGGCCTTC CCCAGCTTCC    2280

TCCTGCAATG CTTCCTGGGG GCCCTGTGGC TGGCTCTGAG TGGCGAAATC AAGGACAAGG    2340

AGCTCCCGCA GTACCTAGCA TTGACCCCAA GGAAGAAGAG GCCCTATGAC AACTGGCTGG    2400

AGGGCGTGCC ACGCTTTCTG GCTGGGCTGA TCTTCCAGCC TCCCGCCCGC TGCCTGGGAG    2460

CCCTACTCGG GCCATCGGCG GCTGCCTCGG TGGACAGGAA GCAGAAGGTG CTTGCGAGGT    2520

ACCTGAAGCG GCTGCAGCCG GGGACACTGC GGGCGCGGCA GCTGCTTGAG CTGCTGCACT    2580

GCGCCCACGA GGCCGAGGAG GCTGGAATTT GGCAGCACGT GGTACAGGAG CTCCCCGGCC    2640

GCCTCTCTTT TCTGGGCACC CGCCTCACGC CTCCTGATGC ACATGTACTG GGCAAGGCCT    2700

TGGAGGCGGC GGGCCAAGAC TTCTCCCTGG ACCTCCGCAG CACTGGCATT TGCCCCTCTG    2760

GATTGGGGAG CCTCGTGGGA CTCAGCTGTG TCACCCGTTT CAGGGCTGCC TTGAGCGACA    2820

CGGTGGCGCT GTGGGAGTCC CTGCGGCAGC ATGGGGAGAC AAGCTACTT CAGGCAGCAG    2880

AGGAGAAGTT CACCATCGAG CCTTTCAAAG CCAAGTCCCT GAAGGATGTG AAGACCTGG    2940

GAAAGCTTGT GCAGACTCAG AGGACGAGAA GTTCCTCGGA AGACACAGCT GGGGAGCTCC    3000

CTGCTGTTCG GGACCTAAAG AAACTGGAGT TTGCGCTGGG CCCTGTCTCA GGCCCCCAGG    3060

CTTTCCCCAA ACTGGTGCGG ATCCTCACGG CCTTTTCCTC CCTGCAGCAT CTGGACCTGG    3120

ATGCGCTGAG TGAGAACAAG ATCGGGGACG AGGGTGTCTC GCAGCTCTCA GCCACCTTCC    3180

CCCAGCTGAA GTCCTTGGAA ACCCTCAATC TGTCCCAGAA CAACATCACT GACCTGGGTG    3240

CCTACAAACT CGCCGAGGCC CTGCCTTCGC TCGCTGCATC CCTGCTCAGG CTAAGCTTGT    3300
```

-continued

| | |
|---|---|
| ACAATAACTG CATCTGCGAC GTGGGAGCCG AGAGCTTGGC TCGTGTGCTT CCGGACATGG | 3360 |
| TGTCCCTCCG GGTGATGGAC GCAAGTTCAC GGCTGCCGGG GCCCAGCAGC TCGCTGCCAG | 3420 |
| CCTTCGGAGG TGTCCTCATG TGGAGACGCT GGCGATGTGG ACGCCCACCA TCCCATTCAG | 3480 |
| TGTCCAGGAA CACCTGCAAC AACAGGATTC ACGGATCAGC CTGAGATGAT CCCAGCTGTG | 3540 |
| CTCTGGACAG GCATGTTCTC TGAGGACACT AACCACGCTG GACCTTGAAC TGGGTACTTG | 3600 |
| TGGACACAGC TCTTCTCCAG GCTGTATCCC ATGAGGCCTC AGCATCCTGG CACCCGGCCC | 3660 |
| CTGCTGGTTC AGGGTTGGCC CCTGCCCGGC TGCGGAATGA ACCACATCTT GCTCTGCTGA | 3720 |
| CAGACACAGG CCCGGCTCCA GGCTCCTTTA GCGCCCAGTT GGGTGGATGC CTGGTGGCAG | 3780 |
| CTGCGGTCCA CCCAGGAGCC CCGAGGCCTT CTCTGAAGGA CATTGCGGAC AGCCACGGCC | 3840 |
| AGGCCAGAGG GAGTGACAGA GGCAGCCCCA TTCTGCCTGC CCAGGCCCCT GCCACCCTGG | 3900 |
| GGAGAAAGTA CTTCTTTTTT TTTATTTTTA GACAGAGTCT CACTGTTGCC CAGGCTGGCG | 3960 |
| TGCAGTGGTG CGATCTGGGT TCACTGCAAC CTCCGCCTCT TGGGTTCAAG CGATTCTTCT | 4020 |
| GCTTCAGCCT CCCGAGTAGC TGGGACTACA GGCACCCACC ATCATGTCTG GCTAATTTTT | 4080 |
| CATTTTTAGT AGAGACAGGG TTTTGCCATG TTGGCCAGGC TGGTCTCAAA CTCTTGACCT | 4140 |
| CAGGTGATCC ACCCACCTCA GCCTCCCAAA GTGCTGGGGA TTACAAGCGT GAGCCACTGC | 4200 |
| ACCGGGCCAC AGAGAAAGTA CTTCTCCACC CTGCTCTCCG ACCAGACACC TTGACAGGGC | 4260 |
| ACACCGGGCA CTCAGAAGAC ACTGATGGGC AACCCCCAGC CTGCTAATTC CCAGATTGC | 4320 |
| AACAGGCTGG GCTTCAGTGG CAGGCTGCTT TTGTCTATGG GACTCAATGC ACTGACATTG | 4380 |
| TTGGCCAAAG CCAAAGCTAG GCCTGGCCAG ATGCACCAGG CCCTTAGCAG GGAAACAGCT | 4440 |
| AATGGGACAC TAATGGGGCG GTGAGAGGGG AACAGACTGA AGCACAGCT TCATTTCCTG | 4500 |
| TGTCTTTTTT CACTACATTA TAAATGTCTC TTTAATGTCA CAAAAAAAAA AAAAAAAAA | 4560 |
| AAAA | 4564 |

(2) INFORMATION FOR SEQ ID NO: 3:

(i) SEQUENCE CHARACTERISTICS:
        (A) LENGTH: 5105 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: cIIta gene of type IV (xi) SEQUENCE DESCRIPTION: SEQ ID NO: 3:

| | |
|---|---|
| GGGGAGAAGT CAGAGGTAAC CTTGCCCCCT CCCTCAATTC CAGATGAGGA AATTCAGGCC | 60 |
| TGAAAAGGGA AAGTGACCAC CTCAAAGTCT CATGCCTTGG AGGACCCAGC AGGAATCCAA | 120 |
| GACCTCTGAA AAGGACCGGC AGGGCTCTTG CCACGGCTGG GGGTGTGGTC ATGGTAACAC | 180 |
| AGGTTTTCCA TCCATGGAAG GTACCTGAGG GATTTTCTCT TCCTCCCTAG GCCAGCATC | 240 |
| AGAGGAGTGA ATAGCTCAGT TAGCTCATCT CAGGGGCCAT GTGCCCTCGG AGGTGGTTTG | 300 |
| CCACTTTCAC GGTTGGACTG AGTTGGAGAG AAACAGAGAC CCACCCAGGG GTGGGGACAA | 360 |
| GCTCCCTGCA ACTCAGGACT TGCAGATCAC TTGCCCAAGT GGCTCCCTAG CTCCTGGCTC | 420 |
| CTGGCCCGGG GCCTGGGACT CTCCCCGAAG TGGGGCTGGC CACTGTGAGG AACCGACTGG | 480 |
| AGGCAGGGAC CTCTTGGATG CCCCAGGCAG TTGGGATGCC ACTTCTGATA AAGCACGTGG | 540 |
| TGGCCACAGT AGGTGCTTGG TTGCTCCACA GCCTGGCCCG AGCTCAGCGC TGCAGAAAGA | 600 |

```
AAGTGAAAGG GAAAAAGAAC TGCGGGGAGG CGGGGAGGTA GGATGACCAG CGGACGAGCT    660

GCCACAGACT TGCCGCGGCC CCAGAGCTGG CGGGAGGGAG AGGCCACCAG CAGCGCGCGC    720

GGGAGCCCGG GGAACAGCGG CAGCTCACAG TGTGCCACCA TGGAGTTGGG GCCCCTAGAA    780

GGTGGCTACC TGGAGCTTCT TAACAGCGAT GCTGACCCCC TGTGCCTCTA CCACTTCTAT    840

GACCAGATGG ACCTGGCTGG AGAAGAAGAG ATTGAGCTCT ACTCAGAACC CGACACAGAC    900

ACCATCAACT GCGACCAGTT CAGCAGGCTG TTGTGTGACA TGGAAGGTGA TGAAGAGACC    960

AGGGAGGCTT ATGCCAATAT CGCGGAACTG GACCAGTATG TCTTCCAGGA CTCCCAGCTG   1020

GAGGGCCTGA GCAAGGACAT TTTCAAGCAC ATAGGACCAG ATGAAGTGAT CGGTGAGAGT   1080

ATGGAGATGC CAGCAGAAGT TGGGCAGAAA AGTCAGAAAA GACCCTTCCC AGAGGAGCTT   1140

CCGGCAGACC TGAAGCACTG GAAGCCAGCT GAGCCCCCCA CTGTGGTGAC TGGCAGTCTC   1200

CTAGTGGGAC CAGTGAGCGA CTGCTCCACC CTGCCCTGCC TGCCACTGCC TGCGCTGTTC   1260

AACCAGGAGC CAGCCTCCGG CCAGATGCGC CTGGAGAAAA CCGACCAGAT TCCCATGCCT   1320

TTCTCCAGTT CCTCGTTGAG CTGCCTGAAT CTCCCTGAGG GACCCATCCA GTTTGTCCCC   1380

ACCATCTCCA CTCTGCCCCA TGGGCTCTGG CAAATCTCTG AGGCTGGAAC AGGGGTCTCC   1440

AGTATATTCA TCTACCATGG TGAGGTGCCC CAGGCCAGCC AAGTACCCCC TCCCAGTGGA   1500

TTCACTGTCC ACGGCCTCCC AACATCTCCA GACCGGCCAG GCTCCACCAG CCCCTTCGCT   1560

CCATCAGCCA CTGACCTGCC CAGCATGCCT GAACCTGCCC TGACCTCCCG AGCAAACATG   1620

ACAGAGCACA AGACGTCCCC CACCCAATGC CCGGCAGCTG GAGAGGTCTC CAACAAGCTT   1680

CCAAAATGGC CTGAGCCGGT GGAGCAGTTC TACCGCTCAC TGCAGGACAC GTATGGTGCC   1740

GAGCCCGCAG GCCCGGATGG CATCCTAGTG GAGGTGGATC TGGTGCAGGC CAGGCTGGAG   1800

AGGAGCAGCA GCAAGAGCCT GGAGCGGGAA CTGGCCACCC CGGACTGGGC AGAACGGCAG   1860

CTGGCCCAAG GAGGCCTGGC TGAGGTGCTG TTGGCTGCCA AGGAGCACCG GCGGCCGCGT   1920

GAGACACGAG TGATTGCTGT GCTGGGCAAA GCTGGTCAGG GCAAGAGCTA TTGGGCTGGG   1980

GCAGTGAGCC GGGCCTGGGC TTGTGGCCGG CTTCCCCAGT ACGACTTTGT CTTCTCTGTC   2040

CCCTGCCATT GCTTGAACCG TCCGGGGGAT GCCTATGGCC TGCAGGATCT GCTCTTCTCC   2100

CTGGGCCCAC AGCCACTCGT GGCGGCCGAT GAGGTTTTCA GCCACATCTT GAAGAGACCT   2160

GACCGCGTTC TGCTCATCCT AGACGCCTTC GAGGAGCTGG AAGCGCAAGA TGGCTTCCTG   2220

CACAGCACGT GCGGACCGGC ACCGGCGGAG CCCTGCTCCC TCCGGGGGCT GCTGGCCGGC   2280

CTTTTCCAGA GAAGCTGCT CCGAGGTTGC ACCCTCCTCC TCACAGCCCG GCCCCGGGGC   2340

CGCCTGGTCC AGAGCCTGAG CAAGGCCGAC GCCCTATTTG AGCTGTCCGG CTTCTCCATG   2400

GAGCAGGCCC AGGCATACGT GATGCGCTAC TTTGAGAGCT CAGGGATGAC AGAGCACCAA   2460

GACAGAGCCC TGACGCTCCT CCGGGACCGG CCACTTCTTC TCAGTCACAG CCACAGCCCT   2520

ACTTTGTGCC GGGCAGTGTG CCAGCTCTCA GAGGCCCTGC TGGAGCTTGG GGAGGACGCC   2580

AAGCTGCCCT CCACGCTCAC GGGACTCTAT GTCGGCCTGC TGGGCCGTGC AGCCCTCGAC   2640

AGCCCCCCCG GGGCCCTGGC AGAGCTGGCC AAGCTGGCCT GGGAGCTGGG CCGCAGACAT   2700

CAAAGTACCC TACAGGAGGA CCAGTTCCCA TCCCAGACG TGAGGACCTG GGCGATGGCC   2760

AAAGGCTTAG TCCAACACCC ACCGCGGGCC GCAGAGTCCG AGCTGGCCTT CCCCAGCTTC   2820

CTCCTGCAAT GCTTCCTGGG GGCCCTGTGG CTGGCTCTGA GTGGCGAAAT CAAGGACAAG   2880

GAGCTCCCGC AGTACCTAGC ATTGACCCCA AGGAAGAAGA GGCCCTATGA CAACTGGCTG   2940
```

-continued

```
GAGGGCGTGC CACGCTTTCT GGCTGGGCTG ATCTTCCAGC CTCCCGCCCG CTGCCTGGGA      3000

GCCCTACTCG GGCCATCGGC GGCTGCCTCG GTGGACAGGA AGCAGAAGGT GCTTGCGAGG      3060

TACCTGAAGC GGCTGCAGCC GGGGACACTG CGGGCGCGGC AGCTGCTTGA GCTGCTGCAC      3120

TGCGCCCACG AGGCCGAGGA GGCTGGAATT TGGCAGCACG TGGTACAGGA GCTCCCCGGC      3180

CGCCTCTCTT TTCTGGGCAC CCGCCTCACG CCTCCTGATG CACATGTACT GGGCAAGGCC      3240

TTGGAGGCGG CGGGCCAAGA CTTCTCCCTG GACCTCCGCA GCACTGGCAT TTGCCCCTCT      3300

GGATTGGGGA GCCTCGTGGG ACTCAGCTGT GTCACCCGTT TCAGGGCTGC CTTGAGCGAC      3360

ACGGTGGCGC TGTGGGAGTC CCTGCGGCAG CATGGGGAGA CCAAGCTACT TCAGGCAGCA      3420

GAGGAGAAGT TCACCATCGA GCCTTTCAAA GCCAAGTCCC TGAAGGATGT GGAAGACCTG      3480

GGAAAGCTTG TGCAGACTCA GAGGACGAGA AGTTCCTCGG AAGACACAGC TGGGGAGCTC      3540

CCTGCTGTTC GGGACCTAAA GAAACTGGAG TTTGCGCTGG GCCCTGTCTC AGGCCCCCAG      3600

GCTTTCCCCA AACTGGTGCG GATCCTCACG GCCTTTTCCT CCCTGCAGCA TCTGGACCTG      3660

GATGCGCTGA GTGAGAACAA GATCGGGGAC GAGGGTGTCT CGCAGCTCTC AGCCACCTTC      3720

CCCCAGCTGA AGTCCTTGGA AACCCTCAAT CTGTCCCAGA ACAACATCAC TGACCTGGGT      3780

GCCTACAAAC TCGCCGAGGC CCTGCCTTCG CTCGCTGCAT CCCTGCTCAG GCTAAGCTTG      3840

TACAATAACT GCATCTGCGA CGTGGGAGCC GAGAGCTTGG CTCGTGTGCT TCCGGACATG      3900

GTGTCCCTCC GGGTGATGGA CGCAAGTTCA CGGCTGCCGG GGCCCAGCAG CTCGCTGCCA      3960

GCCTTCGGAG GTGTCCTCAT GTGGAGACGC TGGCGATGTG GACGCCCACC ATCCCATTCA      4020

GTGTCCAGGA ACACCTGCAA CAACAGGATT CACGGATCAG CCTGAGATGA TCCCAGCTGT      4080

GCTCTGGACA GGCATGTTCT CTGAGGACAC TAACCACGCT GGACCTTGAA CTGGGTACTT      4140

GTGGACACAG CTCTTCTCCA GGCTGTATCC CATGAGGCCT CAGCATCCTG GCACCCGGCC      4200

CCTGCTGGTT CAGGGTTGGC CCCTGCCCGG CTGCGGAATG AACCACATCT TGCTCTGCTG      4260

ACAGACACAG GCCCGGCTCC AGGCTCCTTT AGCGCCCAGT TGGGTGGATG CCTGGTGGCA      4320

GCTGCGGTCC ACCCAGGAGC CCCGAGGCCT TCTCTGAAGG ACATTGCGGA CAGCCACGGC      4380

CAGGCCAGAG GGAGTGACAG AGGCAGCCCC ATTCTGCCTG CCCAGGCCCC TGCCACCCTG      4440

GGGAGAAAGT ACTTCTTTTT TTTTATTTTT AGACAGAGTC TCACTGTTGC CCAGGCTGGC      4500

GTGCAGTGGT GCGATCTGGG TTCACTGCAA CCTCCGCCTC TTGGGTTCAA GCGATTCTTC      4560

TGCTTCAGCC TCCCGAGTAG CTGGGACTAC AGGCACCCAC CATCATGTCT GGCTAATTTT      4620

TCATTTTTAG TAGAGACAGG GTTTTGCCAT GTTGGCCAGG CTGGTCTCAA ACTCTTGACC      4680

TCAGGTGATC CACCCACCTC AGCCTCCCAA AGTGCTGGGG ATTACAAGCG TGAGCCACTG      4740

CACCGGGCCA CAGAGAAAGT ACTTCTCCAC CCTGCTCTCC GACCAGACAC CTTGACAGGG      4800

CACACCGGGC ACTCAGAAGA CACTGATGGG CAACCCCCAG CCTGCTAATT CCCCAGATTG      4860

CAACAGGCTG GGCTTCAGTG GCAGGCTGCT TTTGTCTATG GGACTCAATG CACTGACATT      4920

GTTGGCCAAA GCCAAAGCTA GGCCTGGCCA GATGCACCAG GCCCTTAGCA GGGAAACAGC      4980

TAATGGGACA CTAATGGGGC GGTGAGAGGG GAACAGACTG GAAGCACAGC TTCATTTCCT      5040

GTGTCTTTTT TCACTACATT ATAAATGTCT CTTTAATGTC ACAAAAAAAA AAAAAAAAA      5100

AAAAA                                                                  5105
```

(2) INFORMATION FOR SEQ ID NO: 4:

(i) SEQUENCE CHARACTERISTICS:
        (A) LENGTH: 717 base pairs

```
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: cIIta promoter of type I (xi) SEQUENCE DESCRIPTION: SEQ ID NO: 4:

GTAAGTACTG TAACAGAGAC TAAATGCTAA GTAAGGCAGG CGTGGTGGCT CACACTTGTA      60

ATCCCAGTAC TTTGGAGGAC TGAGGCAAGA GGATCACTTG AGCCCAGAAT TCAAGACCAG     120

CCTGGGAAAC AGAGTGAGAC CCTGTCTCTA CTAAAAATAA AAAATAAAA AATTAGCGGG      180

GCATGATGGT GTGAGTCTGT AGTCCCAGCT ACTGGGAAAC AGAGATGGGA GGTTTGTTTG     240

AGCCTGGGAA GTTGAGGCTG CAGTGAGTTA TGATCACGCC ACTGCACACC AGCCTGGGCA     300

ACAGAGCAAG ACCCTGTCAA AAAAAAAAAA AAGGCTATGT AACACCCCA AGTCACATAA      360

TTGGCAAGGA GCAGCAGATC TGGGACTTGA ACATAGGCAG ATTAGCTCCA AGCCTATTTG     420

CTTAACCTCT ATACCACAAT GCCTTCTTGC TATGGTAAAA CATCTGAAAA GACCTATTAC     480

CCTATAGGTC CTCTAAGGAG GCATGTCGCC TTCCTCTTAG CAATACTAGA TTGGCTCCAA     540

CAGAAGGCTG TGGGCTTCTC TGGCACATGC ACCTGGGTAG GACCCAGAGA ATATCTGTGG     600

AGTCTGAATC AACCCAAAAG CCAATATCCA TCCGTTCATC AGGAACCCCA GCCTACAACG     660

CAAAAGAGGA AATCTTCCTA AGTAGAAATA AACTGTAATA AATTGCAGAG GTTCCCT       717

(2) INFORMATION FOR SEQ ID NO: 5:

(i) SEQUENCE CHARACTERISTICS:
            (A) LENGTH: 133 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: cIIta promoter of type II (xi) SEQUENCE DESCRIPTION: SEQ ID NO: 5:

CCCGGGCGCC CCGCCTCAGT TTCCCCATCT ATAAAGTGGA GATGATAATA GCATTCAGAG      60

TCACTGATCT AAGGGCTCAG GGACACCATT CAGTGTAAGC CCCATACACT CCCTGCAAGA    120

GGAAGCTGGT TCT                                                       133

(2) INFORMATION FOR SEQ ID NO: 6:

(i) SEQUENCE CHARACTERISTICS:
            (A) LENGTH: 664 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: cIIta promoter of type I (xi) SEQUENCE DESCRIPTION: SEQ ID NO: 6:

GGGGAGAAGT CAGAGGTAAC CTTGCCCCCT CCCTCAATTC CAGATGAGGA AATTCAGGCC      60

TGAAAAGGGA AAGTGACCAC CTCAAAGTCT CATGCCTTGG AGGACCCAGC AGGAATCCAA    120

GACCTCTGAA AAGGACCGGC AGGGCTCTTG CCACGGCTGG GGGTGTGGTC ATGGTAACAC    180
```

```
AGGTTTTCCA TCCATGGAAG GTACCTGAGG GATTTTCTCT TCCTCCCTAG GGCCAGCATC      240

AGAGGAGTGA ATAGCTCAGT TAGCTCATCT CAGGGGCCAT GTGCCCTCGG AGGTGGTTTG      300

CCACTTTCAC GGTTGGACTG AGTTGGAGAG AAACAGAGAC CCACCCAGGG GTGGGGACAA      360

GCTCCCTGCA ACTCAGGACT TGCAGATCAC TTGCCCAAGT GGCTCCCTAG CTCCTGGCTC      420

CTGGCCCGGG GCCTGGGACT CTCCCCGAAG TGGGGCTGGC CACTGTGAGG AACCGACTGG      480

AGGCAGGGAC CTCTTGGATG CCCCAGGCAG TTGGGATGCC ACTTCTGATA AGCACGTGG       540

TGGCCACAGT AGGTGCTTGG TTGCTCCACA GCCTGGCCCG AGCTCAGCGC TGCAGAAAGA      600

AAGTGAAAGG GAAAAAGAAC TGCGGGGAGG CGGGGAGGTA GGATGACCAG CGGACGAGCT      660

GCCA                                                                    664

(2) INFORMATION FOR SEQ ID NO: 7:

(i) SEQUENCE CHARACTERISTICS:
        (A) LENGTH: 4746 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: cIIta of type I (xi) SEQUENCE DESCRIPTION: SEQ ID NO: 7:

CGTCCTGGTT TTCACTTCAT GTTTTGGATG CTGCATGCTG GGTGAGCGGA GATTCCAGGC       60

ACTGGCCAGG GCAGCTGCCC TGACTCCAAG GGCTGCCATG AACAACTTCC AGGCCATCCT      120

GACTCAGGTG AGAATGCTGC TCTCCAGCCA TCAGCCCAGC CTGGTGCAGG CCCTCTTGGA      180

CAACCTGCTG AAGGAGGACC TCCTCTCCAG GGAATACCAC TGCACTCTGC TCCATGAGCC      240

TGATAGTGAG GCTCTGGCCA GGAAGATCTC TTTGACCCTA CTAGAGAAAG GAGACCTGGA      300

TTTGGCCCTC CTGGGGTGGG CCCGGAGTGG GCTGCAGCCC CCAGCAGCCG AGAGGGGCCC      360

CGGCCACAGT GACCATGGTG GCAGCTCACA GTGTGCCACC ATGGAGTTGG GGCCCCTAGA      420

AGGTGGCTAC CTGGAGCTTC TTAACAGCGA TGCTGACCCC CTGTGCCTCT ACCACTTCTA      480

TGACCAGATG GACCTGGCTG AGAAGAAGA GATTGAGCTC TACTCAGAAC CCGACACAGA      540

CACCATCAAC TGCGACCAGT TCAGCAGGCT GTTGTGTGAC ATGGAAGGTG ATGAAGAGAC      600

CAGGGAGGCT TATGCCAATA TCGCGGAACT GGACCAGTAT GTCTTCCAGG ACTCCCAGCT      660

GGAGGGCCTG AGCAAGGACA TTTTCAAGCA CATAGGACCA GATGAAGTGA TCGGTGAGAG      720

TATGGAGATG CCAGCAGAAG TTGGGCAGAA AAGTCAGAAA AGACCCTTCC AGAGGAGCT      780

TCCGGCAGAC CTGAAGCACT GGAAGCCAGC TGAGCCCCCC ACTGTGGTGA CTGGCAGTCT      840

CCTAGTGGGA CCAGTGAGCG ACTGCTCCAC CCTGCCCTGC CTGCCACTGC CTGCGCTGTT      900

CAACCAGGAG CCAGCCTCCG GCCAGATGCG CCTGGAGAAA ACCGACCAGA TTCCCATGCC      960

TTTCTCCAGT TCCTCGTTGA GCTGCCTGAA TCTCCCTGAG GGACCCATCC AGTTTGTCCC     1020

CACCATCTCC ACTCTGCCCC ATGGGCTCTG GCAAATCTCT GAGGCTGGAA CAGGGGTCTC     1080

CAGTATATTC ATCTACCATG GTGAGGTGCC CCAGGCCAGC CAAGTACCCC CTCCCAGTGG     1140

ATTCACTGTC CACGGCCTCC CAACATCTCC AGACCGGCCA GGCTCCACCA GCCCCTTCGC     1200

TCCATCAGCC ACTGACCTGC CCAGCATGCC TGAACCTGCC CTGACCTCCC GAGCAAACAT     1260

GACAGAGCAC AAGACGTCCC CCACCCAATG CCCGGCAGCT GGAGAGGTCT CCAACAAGCT     1320

TCCAAAATGG CCTGAGCCGG TGGAGCAGTT CTACCGCTCA CTGCAGGACA CGTATGGTGC     1380
```

```
CGAGCCCGCA GGCCCGGATG GCATCCTAGT GGAGGTGGAT CTGGTGCAGG CCAGGCTGGA   1440

GAGGAGCAGC AGCAAGAGCC TGGAGCGGGA ACTGGCCACC CCGGACTGGG CAGAACGGCA   1500

GCTGGCCCAA GGAGGCCTGG CTGAGGTGCT GTTGGCTGCC AAGGAGCACC GGCGGCCGCG   1560

TGAGACACGA GTGATTGCTG TGCTGGGCAA AGCTGGTCAG GGCAAGAGCT ATTGGGCTGG   1620

GGCAGTGAGC CGGGCCTGGG CTTGTGGCCG GCTTCCCCAG TACGACTTTG TCTTCTCTGT   1680

CCCCTGCCAT TGCTTGAACC GTCCGGGGGA TGCCTATGGC CTGCAGGATC TGCTCTTCTC   1740

CCTGGGCCCA CAGCCACTCG TGGCGGCCGA TGAGGTTTTC AGCCACATCT GAAGAGACC    1800

TGACCGCGTT CTGCTCATCC TAGACGCCTT CGAGGAGCTG AAGCGCAAG ATGGCTTCCT    1860

GCACAGCACG TGCGGACCGG CACCGGCGGA GCCCTGCTCC CTCCGGGGGC TGCTGGCCGG   1920

CCTTTTCCAG AAGAAGCTGC TCCGAGGTTG CACCCTCCTC CTCACAGCCC GGCCCCGGGG   1980

CCGCCTGGTC CAGAGCCTGA GCAAGGCCGA CGCCCTATTT GAGCTGTCCG GCTTCTCCAT   2040

GGAGCAGGCC CAGGCATACG TGATGCGCTA CTTTGAGAGC TCAGGGATGA CAGAGCACCA   2100

AGACAGAGCC CTGACGCTCC TCCGGGACCG GCCACTTCTT CTCAGTCACA GCCACAGCCC   2160

TACTTTGTGC CGGGCAGTGT GCCAGCTCTC AGAGGCCCTG CTGGAGCTTG GGAGGACGC    2220

CAAGCTGCCC TCCACGCTCA CGGGACTCTA TGTCGGCCTG CTGGGCCGTG CAGCCCTCGA   2280

CAGCCCCCCC GGGGCCCTGG CAGAGCTGGC CAAGCTGGCC TGGGAGCTGG GCCGCAGACA   2340

TCAAAGTACC CTACAGGAGG ACCAGTTCCC ATCCGCAGAC GTGAGGACCT GGGCGATGGC   2400

CAAAGGCTTA GTCAACACC CACCGCGGGC CGCAGAGTCC GAGCTGGCCT TCCCCAGCTT    2460

CCTCCTGCAA TGCTTCCTGG GGGCCCTGTG GCTGGCTCTG AGTGGCGAAA TCAAGGACAA   2520

GGAGCTCCCG CAGTACCTAG CATTGACCCC AAGGAAGAAG AGGCCCTATG ACAACTGGCT   2580

GGAGGGCGTG CCACGCTTTC TGGCTGGGCT GATCTTCCAG CCTCCCGCCC GCTGCCTGGG   2640

AGCCCTACTC GGGCCATCGG CGGCTGCCTC GGTGGACAGG AAGCAGAAGG TGCTTGCGAG   2700

GTACCTGAAG CGGCTGCAGC CGGGGACACT GCGGGCGCGG CAGCTGCTTG AGCTGCTGCA   2760

CTGCGCCCAC GAGGCCGAGG AGGCTGGAAT TTGGCAGCAC GTGGTACAGG AGCTCCCCGG   2820

CCGCCTCTCT TTTCTGGGCA CCCGCCTCAC GCCTCCTGAT GCACATGTAC TGGGCAAGGC   2880

CTTGGAGGCG GCGGGCCAAG ACTTCTCCCT GGACCTCCGC AGCACTGGCA TTTGCCCCTC   2940

TGGATTGGGG AGCCTCGTGG GACTCAGCTG TGTCACCCGT TTCAGGGCTG CCTTGAGCGA   3000

CACGGTGGCG CTGTGGGAGT CCCTGCGGCA GCATGGGGAG ACCAAGCTAC TTCAGGCAGC   3060

AGAGGAGAAG TTCACCATCG AGCCTTTCAA AGCCAAGTCC CTGAAGGATG TGGAAGACCT   3120

GGGAAAGCTT GTGCAGACTC AGAGGACGAG AAGTTCCTCG GAAGACACAG CTGGGGAGCT   3180

CCCTGCTGTT CGGGACCTAA AGAAACTGGA GTTTGCGCTG GGCCCTGTCT CAGGCCCCCA   3240

GGCTTTCCCC AAACTGGTGC GGATCCTCAC GGCCTTTTCC TCCCTGCAGC ATCTGGACCT   3300

GGATGCGCTG AGTGAGAACA AGATCGGGGA CGAGGGTGTC TCGCAGCTCT CAGCCACCTT   3360

CCCCCAGCTG AAGTCCTTGG AAACCCTCAA TCTGTCCCAG AACAACATCA CTGACCTGGG   3420

TGCCTACAAA CTCGCCGAGG CCCTGCCTTC GCTCGCTGCA TCCCTGCTCA GGCTAAGCTT   3480

GTACAATAAC TGCATCTGCG ACGTGGGAGC CGAGAGCTTG GCTCGTGTGC TTCCGGACAT   3540

GGTGTCCCTC CGGGTGATGG ACGCAAGTTC ACGGCTGCCG GGCCCAGCA GCTCGCTGCC    3600

AGCCTTCGGA GGTGTCCTCA GTGGAGACG CTGGCGATGT GGACGCCCAC CATCCCATTC    3660

AGTGTCCAGG AACACCTGCA ACAACAGGAT TCACGGATCA GCCTGAGATG ATCCCAGCTG   3720
```

-continued

```
TGCTCTGGAC AGGCATGTTC TCTGAGGACA CTAACCACGC TGGACCTTGA ACTGGGTACT    3780

TGTGGACACA GCTCTTCTCC AGGCTGTATC CCATGAGGCC TCAGCATCCT GGCACCCGGC    3840

CCCTGCTGGT TCAGGGTTGG CCCCTGCCCG GCTGCGGAAT GAACCACATC TTGCTCTGCT    3900

GACAGACACA GGCCCGGCTC CAGGCTCCTT TAGCGCCCAG TTGGGTGGAT GCCTGGTGGC    3960

AGCTGCGGTC CACCCAGGAG CCCCGAGGCC TTCTCTGAAG GACATTGCGG ACAGCCACGG    4020

CCAGGCCAGA GGGAGTGACA GAGGCAGCCC CATTCTGCCT GCCCAGGCCC CTGCCACCCT    4080

GGGGAGAAAG TACTTCTTTT TTTTTATTTT TAGACAGAGT CTCACTGTTG CCCAGGCTGG    4140

CGTGCAGTGG TGCGATCTGG GTTCACTGCA ACCTCCGCCT CTTGGGTTCA AGCGATTCTT    4200

CTGCTTCAGC CTCCCGAGTA GCTGGGACTA CAGGCACCCA CCATCATGTC TGGCTAATTT    4260

TTCATTTTTA GTAGAGACAG GGTTTTGCCA TGTTGGCCAG GCTGGTCTCA AACTCTTGAC    4320

CTCAGGTGAT CCACCCACCT CAGCCTCCCA AAGTGCTGGG GATTACAAGC GTGAGCCACT    4380

GCACCGGGCC ACAGAGAAAG TACTTCTCCA CCCTGCTCTC CGACCAGACA CCTTGACAGG    4440

GCACACCGGG CACTCAGAAG ACACTGATGG GCAACCCCA GCCTGCTAAT TCCCCAGATT    4500

GCAACAGGCT GGGCTTCAGT GGCAGGCTGC TTTTGTCTAT GGGACTCAAT GCACTGACAT    4560

TGTTGGCCAA AGCCAAAGCT AGGCCTGGCC AGATGCACCA GGCCCTTAGC AGGGAAACAG    4620

CTAATGGGAC ACTAATGGGG CGGTGAGAGG GGAACAGACT GGAAGCACAG CTTCATTTCC    4680

TGTGTCTTTT TTCACTACAT TATAAATGTC TCTTTAATGT CACAAAAAAA AAAAAAAAA    4740

AAAAAA                                                                4746
```

(2) INFORMATION FOR SEQ ID NO: 8:

(i) SEQUENCE CHARACTERISTICS:
        (A) LENGTH: 4431 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: cIIta de type II (xi) SEQUENCE DESCRIPTION: SEQ ID NO: 8:

```
GACTCAGCCT TGAGGCTGGC GTCTGAGGCA ACCACAAGCC CAACGTGCAT GGTGGAAAGA      60

TGACTGCAGC TCACAGTGTG CCACCATGGA GTTGGGGCCC CTAGAAGGTG GCTACCTGGA     120

GCTTCTTAAC AGCGATGCTG ACCCCCTGTG CCTCTACCAC TTCTATGACC AGATGGACCT     180

GGCTGGAGAA GAAGAGATTG AGCTCTACTC AGAACCCGAC ACAGACACCA TCAACTGCGA     240

CCAGTTCAGC AGGCTGTTGT GTGACATGGA AGGTGATGAA GAGACCAGGG AGGCTTATGC     300

CAATATCGCG GAACTGGACC AGTATGTCTT CCAGGACTCC CAGCTGGAGG CCTGAGCAA     360

GGACATTTTC AAGCACATAG GACCAGATGA AGTGATCGGT GAGAGTATGG AGATGCCAGC     420

AGAAGTTGGG CAGAAAAGTC AGAAAAGACC CTTCCCAGAG GAGCTTCCGG CAGACCTGAA     480

GCACTGGAAG CCAGCTGAGC CCCCCACTGT GGTGACTGGC AGTCTCCTAG TGGGACCAGT     540

GAGCGACTGC TCCACCCTGC CCTGCCTGCC ACTGCCTGCG CTGTTCAACC AGGAGCCAGC     600

CTCCGGCCAG ATGCGCCTGG AGAAAACCGA CCAGATTCCC ATGCCTTTCT CCAGTTCCTC     660

GTTGAGCTGC CTGAATCTCC CTGAGGGACC CATCCAGTTT GTCCCCACCA TCTCCACTCT     720

GCCCCATGGG CTCTGGCAAA TCTCTGAGGC TGGAACAGGG GTCTCCAGTA TATTCATCTA     780

CCATGGTGAG GTGCCCCAGG CCAGCCAAGT ACCCCCTCCC AGTGGATTCA CTGTCCACGG     840
```

-continued

```
CCTCCCAACA TCTCCAGACC GGCCAGGCTC CACCAGCCCC TTCGCTCCAT CAGCCACTGA    900
CCTGCCCAGC ATGCCTGAAC CTGCCCTGAC CTCCCGAGCA AACATGACAG AGCACAAGAC    960
GTCCCCCACC CAATGCCCGG CAGCTGGAGA GGTCTCCAAC AAGCTTCCAA AATGGCCTGA   1020
GCCGGTGGAG CAGTTCTACC GCTCACTGCA GGACACGTAT GGTGCCGAGC CCGCAGGCCC   1080
GGATGGCATC CTAGTGGAGG TGGATCTGGT GCAGGCCAGG CTGGAGAGGA GCAGCAGCAA   1140
GAGCCTGGAG CGGGAACTGG CCACCCCGGA CTGGGCAGAA CGGCAGCTGG CCCAAGGAGG   1200
CCTGGCTGAG GTGCTGTTGG CTGCCAAGGA GCACCGGCGG CCGCGTGAGA CACGAGTGAT   1260
TGCTGTGCTG GGCAAAGCTG GTCAGGGCAA GAGCTATTGG GCTGGGGCAG TGAGCCGGGC   1320
CTGGGCTTGT GGCCGGCTTC CCCAGTACGA CTTTGTCTTC TCTGTCCCCT GCCATTGCTT   1380
GAACCGTCCG GGGGATGCCT ATGGCCTGCA GGATCTGCTC TTCTCCCTGG GCCCACAGCC   1440
ACTCGTGGCC GCCGATGAGG TTTTCAGCCA CATCTTGAAG AGACCTGACC GCGTTCTGCT   1500
CATCCTAGAC GCCTTCGAGG AGCTGGAAGC GCAAGATGGC TTCCTGCACA GCACGTGCGG   1560
ACCGGCACCG GCGGAGCCCT GCTCCCTCCG GGGGCTGCTG GCCGGCCTTT TCCAGAAGAA   1620
GCTGCTCCGA GGTTGCACCC TCCTCCTCAC AGCCCGGCCC CGGGGCCGCC TGGTCCAGAG   1680
CCTGAGCAAG GCCGACGCCC TATTTGAGCT GTCCGGCTTC TCCATGGAGC AGGCCCAGGC   1740
ATACGTGATG CGCTACTTTG AGAGCTCAGG GATGACAGAG CACCAAGACA GAGCCCTGAC   1800
GCTCCTCCGG GACCGGCCAC TTCTTCTCAG TCACAGCCAC AGCCCTACTT TGTGCCGGGC   1860
AGTGTGCCAG CTCTCAGAGG CCCTGCTGGA GCTTGGGGAG GACGCCAAGC TGCCCTCCAC   1920
GCTCACGGGA CTCTATGTCG GCCTGCTGGG CCGTGCAGCC CTCGACAGCC CCCCCGGGGC   1980
CCTGGCAGAG CTGGCCAAGC TGGCCTGGGA GCTGGGCCGC AGACATCAAA GTACCCTACA   2040
GGAGGACCAG TTCCCATCCG CAGACGTGAG GACCTGGGCG ATGGCCAAAG GCTTAGTCCA   2100
ACACCCACCG CGGGCCGCAG AGTCCGAGCT GGCCTTCCCC AGCTTCCTCC TGCAATGCTT   2160
CCTGGGGGCC CTGTGGCTGG CTCTGAGTGG CGAAATCAAG GACAAGGAGC TCCCGCAGTA   2220
CCTAGCATTG ACCCCAAGGA AGAAGAGGCC CTATGACAAC TGGCTGGAGG GCGTGCCACG   2280
CTTTCTGGCT GGGCTGATCT TCCAGCCTCC CGCCCGCTGC CTGGGAGCCC TACTCGGGCC   2340
ATCGGCGGCT GCCTCGGTGG ACAGGAAGCA GAAGGTGCTT GCGAGGTACC TGAAGCGGCT   2400
GCAGCCGGGG ACACTGCGGG CGCGGCAGCT GCTTGAGCTG CTGCACTGCG CCCACGAGGC   2460
CGAGGAGGCT GGAATTTGGC AGCACGTGGT ACAGGAGCTC CCCGGCCGCC TCTCTTTTCT   2520
GGGCACCCGC CTCACGCCTC CTGATGCACA TGTACTGGGC AAGGCCTTGG AGGCGGCGGG   2580
CCAAGACTTC TCCCTGGACC TCCGCAGCAC TGGCATTTGC CCCTCTGGAT TGGGGAGCCT   2640
CGTGGGACTC AGCTGTGTCA CCCGTTTCAG GGCTGCCTTG AGCGACACGG TGGCGCTGTG   2700
GGAGTCCCTG CGGCAGCATG GGGAGACCAA GCTACTTCAG GCAGCAGAGG AGAAGTTCAC   2760
CATCGAGCCT TTCAAAGCCA AGTCCCTGAA GGATGTGGAA GACCTGGGAA AGCTTGTGCA   2820
GACTCAGAGG ACGAGAAGTT CCTCGGAAGA CACAGCTGGG GAGCTCCCTG CTGTTCGGGA   2880
CCTAAAGAAA CTGGAGTTTG CGCTGGGCCC TGTCTCAGGC CCCCAGGCTT TCCCCAAACT   2940
GGTGCGGATC CTCACGGCCT TTTCCTCCCT GCAGCATCTG GACCTGGATG CGCTGAGTGA   3000
GAACAAGATC GGGGACGAGG GTGTCTCGCA GCTCTCAGCC ACCTTCCCCC AGCTGAAGTC   3060
CTTGAAACCC CTCAATCTGT CCCAGAACAA CATCACTGAC CTGGGTGCCT ACAAACTCGC   3120
CGAGGCCCTG CCTTCGCTCG CTGCATCCCT GCTCAGGCTA AGCTTGTACA ATAACTGCAT   3180
```

-continued

```
CTGCGACGTG GGAGCCGAGA GCTTGGCTCG TGTGCTTCCG GACATGGTGT CCCTCCGGGT      3240

GATGGACGCA AGTTCACGGC TGCCGGGGCC CAGCAGCTCG CTGCCAGCCT TCGGAGGTGT      3300

CCTCATGTGG AGACGCTGGC GATGTGGACG CCCACCATCC CATTCAGTGT CCAGGAACAC      3360

CTGCAACAAC AGGATTCACG GATCAGCCTG AGATGATCCC AGCTGTGCTC TGGACAGGCA      3420

TGTTCTCTGA GGACACTAAC CACGCTGGAC CTTGAACTGG GTACTTGTGG ACACAGCTCT      3480

TCTCCAGGCT GTATCCCATG AGGCCTCAGC ATCCTGGCAC CCGGCCCCTG CTGGTTCAGG      3540

GTTGGCCCCT GCCCGGCTGC GGAATGAACC ACATCTTGCT CTGCTGACAG ACACAGGCCC      3600

GGCTCCAGGC TCCTTTAGCG CCCAGTTGGG TGGATGCCTG GTGGCAGCTG CGGTCCACCC      3660

AGGAGCCCCG AGGCCTTCTC TGAAGGACAT TGCGGACAGC CACGGCCAGG CCAGAGGGAG      3720

TGACAGAGGC AGCCCCATTC TGCCTGCCCA GGCCCCTGCC ACCCTGGGGA GAAAGTACTT      3780

CTTTTTTTTT ATTTTTAGAC AGAGTCTCAC TGTTGCCCAG GCTGGCGTGC AGTGGTGCGA      3840

TCTGGGTTCA CTGCAACCTC CGCCTCTTGG GTTCAAGCGA TTCTTCTGCT TCAGCCTCCC      3900

GAGTAGCTGG GACTACAGGC ACCCACCATC ATGTCTGGCT AATTTTTCAT TTTTAGTAGA      3960

GACAGGGTTT TGCCATGTTG GCCAGGCTGG TCTCAAACTC TTGACCTCAG GTGATCCACC      4020

CACCTCAGCC TCCCAAAGTG CTGGGGATTA CAAGCGTGAG CCACTGCACC GGGCCACAGA      4080

GAAAGTACTT CTCCACCCTG CTCTCCGACC AGACACCTTG ACAGGGCACA CCGGGCACTC      4140

AGAAGACACT GATGGGCAAC CCCCAGCCTG CTAATTCCCC AGATTGCAAC AGGCTGGGCT      4200

TCAGTGGCAG GCTGCTTTTG TCTATGGGAC TCAATGCACT GACATTGTTG GCCAAAGCCA      4260

AAGCTAGGCC TGGCCAGATG CACCAGGCCC TTAGCAGGGA AACAGCTAAT GGGACACTAA      4320

TGGGGCGGTG AGAGGGAAC AGACTGGAAG CACAGCTTCA TTTCCTGTGT CTTTTTTCAC      4380

TACATTATAA ATGTCTCTTT AATGTCACAA AAAAAAAAAA AAAAAAAAAA A              4431
```

(2) INFORMATION FOR SEQ ID NO: 9:

(i) SEQUENCE CHARACTERISTICS:
        (A) LENGTH: 4549 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: cIIta of type III (xi) SEQUENCE DESCRIPTION: SEQ ID NO: 9:

```
TTAGTGATGA GGCTAGTGAT GAGGCTGTGT GCTTCTGAGC TGGGCATCCG AAGGCATCCT       60

TGGGGAAGCT GAGGGCACGA GGAGGGGCTG CCAGACTCCG GGAGCTGCTG CCTGGCTGGG      120

ATTCCTACAC AATGCGTTGC CTGGCTCCAC GCCCTGCTGG GTCCTACCTG TCAGAGCCCC      180

AAGGCAGCTC ACAGTGTGCC ACCATGGAGT TGGGGCCCCT AGAAGGTGGC TACCTGGAGC      240

TTCTTAACAG CGATGCTGAC CCCCTGTGCC TCTACCACTT CTATGACCAG ATGGACCTGG      300

CTGGAGAAGA AGAGATTGAG CTCTACTCAG AACCCGACAC AGACACCATC AACTGCGACC      360

AGTTCAGCAG GCTGTTGTGT GACATGGAAG GTGATGAAGA GACCAGGGAG GCTTATGCCA      420

ATATCGCGGA ACTGGACCAG TATGTCTTCC AGGACTCCCA GCTGGAGGGC CTGAGCAAGG      480

ACATTTTCAA GCACATAGGA CCAGATGAAG TGATCGGTGA GAGTATGGAG ATGCCAGCAG      540

AAGTTGGGCA GAAAAGTCAG AAAAGACCCT TCCCAGAGGA GCTTCCGGCA GACCTGAAGC      600

ACTGGAAGCC AGCTGAGCCC CCCACTGTGG TGACTGGCAG TCTCCTAGTG GGACCAGTGA      660
```

```
                                      -continued

GCGACTGCTC CACCCTGCCC TGCCTGCCAC TGCCTGCGCT GTTCAACCAG GAGCCAGCCT      720

CCGGCCAGAT GCGCCTGGAG AAAACCGACC AGATTCCCAT GCCTTTCTCC AGTTCCTCGT      780

TGAGCTGCCT GAATCTCCCT GAGGGACCCA TCCAGTTTGT CCCCACCATC TCCACTCTGC      840

CCCATGGGCT CTGGCAAATC TCTGAGGCTG AACAGGGGT CTCCAGTATA TTCATCTACC       900

ATGGTGAGGT GCCCCAGGCC AGCCAAGTAC CCCCTCCCAG TGGATTCACT GTCCACGGCC      960

TCCCAACATC TCCAGACCGG CCAGGCTCCA CCAGCCCCTT CGCTCCATCA GCCACTGACC     1020

TGCCCAGCAT GCCTGAACCT GCCCTGACCT CCCGAGCAAA CATGACAGAG CACAAGACGT     1080

CCCCCACCCA ATGCCCGGCA GCTGGAGAGG TCTCCAACAA GCTTCCAAAA TGGCCTGA       1140

CGGTGGAGCA GTTCTACCGC TCACTGCAGG ACACGTATGG TGCCGAGCCC GCAGGCCCGG     1200

ATGGCATCCT AGTGGAGGTG GATCTGGTGC AGGCCAGGCT GGAGAGGAGC AGCAGCAAGA     1260

GCCTGGAGCG GGAACTGGCC ACCCCGGACT GGGCAGAACG GCAGCTGGCC CAAGGAGGCC     1320

TGGCTGAGGT GCTGTTGGCT GCCAAGGAGC ACCGGCGGCC GCGTGAGACA CGAGTGATTG     1380

CTGTGCTGGG CAAAGCTGGT CAGGGCAAGA GCTATTGGGC TGGGGCAGTG AGCCGGGCCT     1440

GGGCTTGTGG CCGGCTTCCC CAGTACGACT TTGTCTTCTC TGTCCCCTGC CATTGCTTGA     1500

ACCGTCCGGG GGATGCCTAT GGCCTGCAGG ATCTGCTCTT CTCCCTGGGC CCACAGCCAC     1560

TCGTGGCGGC CGATGAGGTT TTCAGCCACA TCTTGAAGAG ACCTGACCGC GTTCTGCTCA     1620

TCCTAGACGC CTTCGAGGAG CTGGAAGCGC AAGATGGCTT CCTGCACAGC ACGTGCGGAC     1680

CGGCACCGGC GGAGCCCTGC TCCCTCCGGG GGCTGCTGGC CGGCCTTTTC CAGAAGAAGC     1740

TGCTCCGAGG TTGCACCCTC CTCCTCACAG CCCGGCCCCG GGGCCGCCTG GTCCAGAGCC     1800

TGAGCAAGGC CGACGCCCTA TTTGAGCTGT CCGGCTTCTC CATGGAGCAG GCCCAGGCAT     1860

ACGTGATGCG CTACTTTGAG AGCTCAGGGA TGACAGAGCA CCAAGACAGA GCCCTGACGC     1920

TCCTCCGGGA CCGGCCACTT CTTCTCAGTC ACAGCCACAG CCCTACTTTG TGCCGGGCAG     1980

TGTGCCAGCT CTCAGAGGCC CTGCTGGAGC TTGGGGAGGA CGCCAAGCTG CCCTCCACGC     2040

TCACGGGACT CTATGTCGGC CTGCTGGGCC GTGCAGCCCT CGACAGCCCC CCGGGGCCC     2100

TGGCAGAGCT GGCCAAGCTG GCCTGGGAGC TGGGCCGCAG ACATCAAAGT ACCCTACAGG     2160

AGGACCAGTT CCCATCCGCA GACGTGAGGA CCTGGGCGAT GGCCAAAGGC TTAGTCCAAC     2220

ACCCACCGCG GGCCGCAGAG TCCGAGCTGG CCTTCCCCAG CTTCCTCCTG CAATGCTTCC     2280

TGGGGGCCCT GTGGCTGGCT CTGAGTGGCG AAATCAAGGA CAAGGAGCTC CCGCAGTACC     2340

TAGCATTGAC CCCAAGGAAG AAGAGGCCCT ATGACAACTG GCTGGAGGGC GTGCCACGCT     2400

TTCTGGCTGG GCTGATCTTC CAGCCTCCCG CCCGCTGCCT GGGAGCCCTA CTCGGGCCAT     2460

CGGCGGCTGC CTCGGTGGAC AGGAAGCAGA AGGTGCTTGC GAGGTACCTG AAGCGGCTGC     2520

AGCCGGGGAC ACTGCGGGCG CGGCAGCTGC TTGAGCTGCT GCACTGCGCC CACGAGGCCG     2580

AGGAGGCTGG AATTTGGCAG CACGTGGTAC AGGAGCTCCC CGGCCGCCTC TCTTTTCTGG     2640

GCACCCGCCT CACGCCTCCT GATGCACATG TACTGGGCAA GGCCTTGGAG GCGGCGGGCC     2700

AAGACTTCTC CCTGGACCTC CGCAGCACTG GCATTTGCCC CTCTGGATTG GGGAGCCTCG     2760

TGGGACTCAG CTGTGTCACC CGTTTCAGGG CTGCCTTGAG CGACACGGTG GCGCTGTGGG     2820

AGTCCCTGCG GCAGCATGGG GAGACCAAGC TACTTCAGGC AGCAGAGGAG AAGTTCACCA     2880

TCGAGCCTTT CAAAGCCAAG TCCCTGAAGG ATGTGGAAGA CCTGGGAAAG CTTGTGCAGA     2940

CTCAGAGGAC GAGAAGTTCC TCGGAAGACA CAGCTGGGGA GCTCCCTGCT GTTCGGGACC     3000
```

```
TAAAGAAACT GGAGTTTGCG CTGGGCCCTG TCTCAGGCCC CCAGGCTTTC CCCAAACTGG      3060

TGCGGATCCT CACGGCCTTT TCCTCCCTGC AGCATCTGGA CCTGGATGCG CTGAGTGAGA      3120

ACAAGATCGG GGACGAGGGT GTCTCGCAGC TCTCAGCCAC CTTCCCCCAG CTGAAGTCCT      3180

TGGAAACCCT CAATCTGTCC CAGAACAACA TCACTGACCT GGGTGCCTAC AAACTCGCCG      3240

AGGCCCTGCC TTCGCTCGCT GCATCCCTGC TCAGGCTAAG CTTGTACAAT AACTGCATCT      3300

GCGACGTGGG AGCCGAGAGC TTGGCTCGTG TGCTTCCGGA CATGGTGTCC CTCCGGGTGA      3360

TGGACGCAAG TTCACGGCTG CCGGGGCCCA GCAGCTCGCT GCCAGCCTTC GGAGGTGTCC      3420

TCATGTGGAG ACGCTGGCGA TGTGGACGCC CACCATCCCA TTCAGTGTCC AGGAACACCT      3480

GCAACAACGA GATTCACGGA TCAGCCTGAG ATGATCCCAG CTGTGCTCTG GACAGGCATG      3540

TTCTCTGAGG ACACTAACCA CGCTGGACCT TGAACTGGGT ACTTGTGGAC ACAGCTCTTC      3600

TCCAGGCTGT ATCCCATGAG GCCTCAGCAT CCTGGCACCC GGCCCCTGCT GGTTCAGGGT      3660

TGGCCCCTGC CCGGCTGCGG AATGAACCAC ATCTTGCTCT GCTGACAGAC ACAGGCCCGG      3720

CTCCAGGCTC CTTTAGCGCC CAGTTGGGTG GATGCCTGGT GGCAGCTGCG GTCCACCCAG      3780

GAGCCCCGAG GCCTTCTCTG AAGGACATTG CGGACAGCCA CGGCCAGGCC AGAGGGAGTG      3840

ACAGAGGCAG CCCCATTCTG CCTGCCCAGG CCCCTGCCAC CCTGGGGAGA AAGTACTTCT      3900

TTTTTTTTAT TTTTAGACAG AGTCTCACTG TTGCCCAGGC TGGCGTGCAG TGGTGCGATC      3960

TGGGTTCACT GCAACCTCCG CCTCTTGGGT TCAAGCGATT CTTCTGCTTC AGCCTCCCGA      4020

GTAGCTGGGA CTACAGGCAC CCACCATCAT GTCTGGCTAA TTTTTCATTT TTAGTAGAGA      4080

CAGGGTTTTG CCATGTTGGC CAGGCTGGTC TCAAACTCTT GACCTCAGGT GATCCACCCA      4140

CCTCAGCCTC CCAAAGTGCT GGGGATTACA AGCGTGAGCC ACTGCACCGG CCACAGAGA      4200

AAGTACTTCT CCACCCTGCT CTCCGACCAG ACACCTTGAC AGGGCACACC GGGCACTCAG      4260

AAGACACTGA TGGGCAACCC CCAGCCTGCT AATTCCCCAG ATTGCAACAG GCTGGGCTTC      4320

AGTGGCAGGC TGCTTTTGTC TATGGGACTC AATGCACTGA CATTGTTGGC CAAAGCCAAA      4380

GCTAGGCCTG GCCAGATGCA CCAGGCCCTT AGCAGGGAAA CAGCTAATGG GACACTAATG      4440

GGGCGGTGAG AGGGGAACAG ACTGGAAGCA CAGCTTCATT TCCTGTGTCT TTTTTCACTA      4500

CATTATAAAT GTCTCTTTAA TGTCACAAAA AAAAAAAAA AAAAAAAA                   4549

(2) INFORMATION FOR SEQ ID NO: 10:

(i) SEQUENCE CHARACTERISTICS:
        (A) LENGTH: 4441 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: cIIta of type IV (xi) SEQUENCE DESCRIPTION: SEQ ID NO: 10:

CAGACTTGCC GCGGCCCCAG AGCTGGCGGG AGGGAGAGGC CACCAGCAGC GCGCGCGGGA        60

GCCCGGGGAA CAGCGGCAGC TCACAGTGTG CCACCATGGA GTTGGGGCCC CTAGAAGGTG       120

GCTACCTGGA GCTTCTTAAC AGCGATGCTG ACCCCCTGTG CCTCTACCAC TTCTATGACC       180

AGATGGACCT GGCTGGAGAA GAAGAGATTG AGCTCTACTC AGAACCCGAC ACAGACACCA       240

TCAACTGCGA CCAGTTCAGC AGGCTGTTGT GTGACATGGA AGGTGATGAA GAGACCAGGG       300

AGGCTTATGC CAATATCGCG GAACTGGACC AGTATGTCTT CCAGGACTCC CAGCTGGAGG       360
```

-continued

```
GCCTGAGCAA GGACATTTTC AAGCACATAG GACCAGATGA AGTGATCGGT GAGAGTATGG    420

AGATGCCAGC AGAAGTTGGG CAGAAAAGTC AGAAAAGACC CTTCCCAGAG GAGCTTCCGG    480

CAGACCTGAA GCACTGGAAG CCAGCTGAGC CCCCCACTGT GGTGACTGGC AGTCTCCTAG    540

TGGGACCAGT GAGCGACTGC TCCACCCTGC CCTGCCTGCC ACTGCCTGCG CTGTTCAACC    600

AGGAGCCAGC CTCCGGCCAG ATGCGCCTGG AGAAAACCGA CCAGATTCCC ATGCCTTTCT    660

CCAGTTCCTC GTTGAGCTGC CTGAATCTCC CTGAGGGACC CATCCAGTTT GTCCCCACCA    720

TCTCCACTCT GCCCCATGGG CTCTGGCAAA TCTCTGAGGC TGGAACAGGG GTCTCCAGTA    780

TATTCATCTA CCATGGTGAG GTGCCCCAGG CCAGCCAAGT ACCCCCTCCC AGTGGATTCA    840

CTGTCCACGG CCTCCCAACA TCTCCAGACC GGCCAGGCTC CACCAGCCCC TTCGCTCCAT    900

CAGCCACTGA CCTGCCCAGC ATGCCTGAAC CTGCCCTGAC CTCCCGAGCA AACATGACAG    960

AGCACAAGAC GTCCCCCACC CAATGCCCGG CAGCTGGAGA GGTCTCCAAC AAGCTTCCAA   1020

AATGGCCTGA GCCGGTGGAG CAGTTCTACC GCTCACTGCA GGACACGTAT GGTGCCGAGC   1080

CCGCAGGCCC GGATGGCATC CTAGTGGAGG TGGATCTGGT GCAGGCCAGG CTGGAGAGGA   1140

GCAGCAGCAA GAGCCTGGAG CGGGAACTGG CCACCCCGGA CTGGGCAGAA CGGCAGCTGG   1200

CCCAAGGAGG CCTGGCTGAG GTGCTGTTGG CTGCCAAGGA GCACCGGCGG CCGCGTGAGA   1260

CACGAGTGAT TGCTGTGCTG GGCAAAGCTG GTCAGGGCAA GAGCTATTGG CTGGGGCAG    1320

TGAGCCGGGC CTGGGCTTGT GGCCGGCTTC CCCAGTACGA CTTTGTCTTC TCTGTCCCCT   1380

GCCATTGCTT GAACCGTCCG GGGGATGCCT ATGGCCTGCA GGATCTGCTC TTCTCCCTGG   1440

GCCCACAGCC ACTCGTGGCG GCCGATGAGG TTTTCAGCCA CATCTTGAAG AGACCTGACC   1500

GCGTTCTGCT CATCCTAGAC GCCTTCGAGG AGCTGGAAGC GCAAGATGGC TTCCTGCACA   1560

GCACGTGCGG ACCGGCACCG GCGGAGCCCT GCTCCCTCCG GGGCTGCTG GCCGGCCTTT   1620

TCCAGAAGAA GCTGCTCCGA GGTTGCACCC TCCTCCTCAC AGCCCGGCCC CGGGGCCGCC   1680

TGGTCCAGAG CCTGAGCAAG GCCGACGCCC TATTTGAGCT GTCCGGCTTC TCCATGGAGC   1740

AGGCCCAGGC ATACGTGATG CGCTACTTTG AGAGCTCAGG GATGACAGAG CACCAAGACA   1800

GAGCCCTGAC GCTCCTCCGG GACCGGCCAC TTCTTCTCAG TCACAGCCAC AGCCCTACTT   1860

TGTGCCGGGC AGTGTGCCAG CTCTCAGAGG CCCTGCTGGA GCTTGGGGAG GACGCCAAGC   1920

TGCCCTCCAC GCTCACGGGA CTCTATGTCG GCCTGCTGGG CCGTGCAGCC CTCGACAGCC   1980

CCCCCGGGGC CCTGGCAGAG CTGGCCAAGC TGGCCTGGGA GCTGGGCCGC AGACATCAAA   2040

GTACCCTACA GGAGGACCAG TTCCCATCCG CAGACGTGAG GACCTGGGCG ATGGCCAAAG   2100

GCTTAGTCCA ACACCCACCG CGGGCCGCAG AGTCCGAGCT GGCCTTCCCC AGCTTCCTCC   2160

TGCAATGCTT CCTGGGGGCC CTGTGGCTGG CTCTGAGTGG CGAAATCAAG GACAAGGAGC   2220

TCCCGCAGTA CCTAGCATTG ACCCCAAGGA AGAAGAGGCC CTATGACAAC TGGCTGGAGG   2280

GCGTGCCACG CTTTCTGGCT GGGCTGATCT TCCAGCCTCC CGCCCGCTGC CTGGGAGCCC   2340

TACTCGGGCC ATCGGCGGCT GCCTCGGTGG ACAGGAAGCA GAAGGTGCTT GCGAGGTACC   2400

TGAAGCGGCT GCAGCCGGGG ACACTGCGGG CGCGGCAGCT GCTTGAGCTG CTGCACTGCG   2460

CCCACGAGGC CGAGGAGGCT GGAATTTGGC AGCACGTGGT ACAGGAGCTC CCCGGCCGCC   2520

TCTCTTTTCT GGGCACCCGC CTCACGCCTC CTGATGCACA TGTACTGGGC AAGGCCTTGG   2580

AGGCGGCGGG CCAAGACTTC TCCCTGGACC TCCGCAGCAC TGGCATTTGC CCCTCTGGAT   2640

TGGGGAGCCT CGTGGGACTC AGCTGTGTCA CCCGTTTCAG GGCTGCCTTG AGCGACACGG   2700
```

-continued

```
TGGCGCTGTG GGAGTCCCTG CGGCAGCATG GGGAGACCAA GCTACTTCAG GCAGCAGAGG      2760

AGAAGTTCAC CATCGAGCCT TTCAAAGCCA AGTCCCTGAA GGATGTGGAA GACCTGGGAA      2820

AGCTTGTGCA GACTCAGAGG ACGAGAAGTT CCTCGGAAGA CACAGCTGGG GAGCTCCCTG      2880

CTGTTCGGGA CCTAAAGAAA CTGGAGTTTG CGCTGGGCCC TGTCTCAGGC CCCCAGGCTT      2940

TCCCCAAACT GGTGCGGATC CTCACGGCCT TTTCCTCCCT GCAGCATCTG GACCTGGATG      3000

CGCTGAGTGA GAACAAGATC GGGGACGAGG GTGTCTCGCA GCTCTCAGCC ACCTTCCCCC      3060

AGCTGAAGTC CTTGGAAACC CTCAATCTGT CCCAGAACAA CATCACTGAC CTGGGTGCCT      3120

ACAAACTCGC CGAGGCCCTG CCTTCGCTCG CTGCATCCCT GCTCAGGCTA AGCTTGTACA      3180

ATAACTGCAT CTGCGACGTG GGAGCCGAGA GCTTGGCTCG TGTGCTTCCG GACATGGTGT      3240

CCCTCCGGGT GATGGACGCA AGTTCACGGC TGCCGGGGCC CAGCAGCTCG CTGCCAGCCT      3300

TCGGAGGTGT CCTCATGTGG AGACGCTGGC GATGTGGACG CCCACCATCC CATTCAGTGT      3360

CCAGGAACAC CTGCAACAAC AGGATTCACG GATCAGCCTG AGATGATCCC AGCTGTGCTC      3420

TGGACAGGCA TGTTCTCTGA GGACACTAAC CACGCTGGAC CTTGAACTGG GTACTTGTGG      3480

ACACAGCTCT TCTCCAGGCT GTATCCCATG AGGCCTCAGC ATCCTGGCAC CCGGCCCCTG      3540

CTGGTTCAGG GTTGGCCCCT GCCCGGCTGC GGAATGAACC ACATCTTGCT CTGCTGACAG      3600

ACACAGGCCC GGCTCCAGGC TCCTTTAGCG CCCAGTTGGG TGGATGCCTG GTGGCAGCTG      3660

CGGTCCACCC AGGAGCCCCG AGGCCTTCTC TGAAGGACAT TGCGGACAGC CACGGCCAGG      3720

CCAGAGGGAG TGACAGAGGC AGCCCCATTC TGCCTGCCCA GGCCCCTGCC ACCCTGGGGA      3780

GAAAGTACTT CTTTTTTTTT ATTTTTAGAC AGAGTCTCAC TGTTGCCCAG GCTGGCGTGC      3840

AGTGGTGCGA TCTGGGTTCA CTGCAACCTC CGCCTCTTGG GTTCAAGCGA TTCTTCTGCT      3900

TCAGCCTCCC GAGTAGCTGG GACTACAGGC ACCCACCATC ATGTCTGGCT AATTTTTCAT      3960

TTTTAGTAGA GACAGGGTTT TGCCATGTTG GCCAGGCTGG TCTCAAACTC TTGACCTCAG      4020

GTGATCCACC CACCTCAGCC TCCCAAAGTG CTGGGGATTA CAAGCGTGAG CCACTGCACC      4080

GGGCCACAGA GAAAGTACTT CTCCACCCTG CTCTCCGACC AGACACCTTG ACAGGGCACA      4140

CCGGGCACTC AGAAGACACT GATGGGCAAC CCCCAGCCTG CTAATTCCCC AGATTGCAAC      4200

AGGCTGGGCT TCAGTGGCAG GCTGCTTTTG TCTATGGGAC TCAATGCACT GACATTGTTG      4260

GCCAAAGCCA AAGCTAGGCC TGGCCAGATG CACCAGGCCC TTAGCAGGGA AACAGCTAAT      4320

GGGACACTAA TGGGGCGGTG AGAGGGGAAC AGACTGGAAG CACAGCTTCA TTTCCTGTGT      4380

CTTTTTTCAC TACATTATAA ATGTCTCTTT AATGTCACAA AAAAAAAAAA AAAAAAAAA      4440

A                                                                    4441
```

(2) INFORMATION FOR SEQ ID NO: 11:

(i) SEQUENCE CHARACTERISTICS:
        (A) LENGTH: 4649 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: cIIta of type I (xi) SEQUENCE DESCRIPTION: SEQ ID NO: 11:

```
ATGAACAACT TCCAGGCCAT CCTGACTCAG GTGAGAATGC TGCTCTCCAG CCATCAGCCC        60

AGCCTGGTGC AGGCCCTCTT GGACAACCTG CTGAAGGAGG ACCTCCTCTC CAGGGAATAC       120
```

-continued

```
CACTGCACTC TGCTCCATGA GCCTGATAGT GAGGCTCTGG CCAGGAAGAT CTCTTTGACC      180

CTACTAGAGA AAGGAGACCT GGATTTGGCC CTCCTGGGGT GGGCCCGGAG TGGGCTGCAG      240

CCCCCAGCAG CCGAGAGGGG CCCCGGCCAC AGTGACCATG GTGGCAGCTC ACAGTGTGCC      300

ACCATGGAGT TGGGGCCCCT AGAAGGTGGC TACCTGGAGC TTCTTAACAG CGATGCTGAC      360

CCCCTGTGCC TCTACCACTT CTATGACCAG ATGGACCTGG CTGGAGAAGA AGAGATTGAG      420

CTCTACTCAG AACCCGACAC AGACACCATC AACTGCGACC AGTTCAGCAG GCTGTTGTGT      480

GACATGGAAG GTGATGAAGA GACCAGGGAG GCTTATGCCA ATATCGCGGA ACTGGACCAG      540

TATGTCTTCC AGGACTCCCA GCTGGAGGGC CTGAGCAAGG ACATTTTCAA GCACATAGGA      600

CCAGATGAAG TGATCGGTGA GAGTATGGAG ATGCCAGCAG AAGTTGGGCA GAAAAGTCAG      660

AAAAGACCCT TCCCAGAGGA GCTTCCGGCA GACCTGAAGC ACTGGAAGCC AGCTGAGCCC      720

CCCACTGTGG TGACTGGCAG TCTCCTAGTG GGACCAGTGA GCGACTGCTC CACCCTGCCC      780

TGCCTGCCAC TGCCTGCGCT GTTCAACCAG GAGCCAGCCT CCGGCCAGAT GCGCCTGGAG      840

AAAACCGACC AGATTCCCAT GCCTTTCTCC AGTTCCTCGT TGAGCTGCCT GAATCTCCCT      900

GAGGGACCCA TCCAGTTTGT CCCCACCATC TCCACTCTGC CCATGGGCT CTGGCAAATC      960

TCTGAGGCTG GAACAGGGGT CTCCAGTATA TTCATCTACC ATGGTGAGGT GCCCCAGGCC     1020

AGCCAAGTAC CCCCTCCCAG TGGATTCACT GTCCACGGCC TCCCAACATC TCCAGACCGG     1080

CCAGGCTCCA CCAGCCCCTT CGCTCCATCA GCCACTGACC TGCCCAGCAT GCCTGAACCT     1140

GCCCTGACCT CCCGAGCAAA CATGACAGAG CACAAGACGT CCCCCACCCA ATGCCCGGCA     1200

GCTGGAGAGG TCTCCAACAA GCTTCCAAAA TGGCCTGAGC CGGTGGAGCA GTTCTACCGC     1260

TCACTGCAGG ACACGTATGG TGCCGAGCCC GCAGGCCCGG ATGGCATCCT AGTGGAGGTG     1320

GATCGGTGC AGGCCAGGCT GGAGAGGAGC AGCAGCAAGA GCCTGGAGCG GGAACTGGCC      1380

ACCCCGGACT GGGCAGAACG GCAGCTGGCC CAAGGAGGCC TGGCTGAGGT GCTGTTGGCT     1440

GCCAAGGAGC ACCGGCGGCC GCGTGAGACA CGAGTGATTG CTGTGCTGGG CAAAGCTGGT     1500

CAGGGCAAGA GCTATTGGGC TGGGGCAGTG AGCCGGGCCT GGGCTTGTGG CCGGCTTCCC     1560

CAGTACGACT TTGTCTTCTC TGTCCCCTGC CATTGCTTGA ACCGTCCGGG GGATGCCTAT     1620

GGCCTGCAGG ATCTGCTCTT CTCCCTGGGC CCACAGCCAC TCGTGGCGGC CGATGAGGTT     1680

TTCAGCCACA TCTTGAAGAG ACCTGACCGC GTTCTGCTCA TCCTAGACGC CTTCGAGGAG     1740

CTGGAAGCGC AAGATGGCTT CCTGCACAGC ACGTGCGGAC CGGCACCGGC GGAGCCCTGC     1800

TCCCTCCGGG GGCTGCTGGC CGGCCTTTTC CAGAAGAAGC TGCTCCGAGG TTGCACCCTC     1860

CTCCTCACAG CCCGGCCCCG GGGCCGCCTG GTCCAGAGCC TGAGCAAGGC CGACGCCCTA     1920

TTTGAGCTGT CCGGCTTCTC CATGGAGCAG GCCCAGGCAT ACGTGATGCG CTACTTTGAG     1980

AGCTCAGGGA TGACAGAGCA CCAAGACAGA GCCCTGACGC TCCTCCGGGA CCGGCCACTT     2040

CTTCTCAGTC ACAGCCACAG CCCTACTTTG TGCCGGGCAG TGTGCCAGCT CTCAGAGGCC     2100

CTGCTGGAGC TTGGGGAGGA CGCCAAGCTG CCCTCCACGC TCACGGGACT CTATGTCGGC     2160

CTGCTGGGCC GTGCAGCCCT CGACAGCCCC CCGGGGCCC TGGCAGAGCT GGCCAAGCTG      2220

GCCTGGGAGC TGGGCCGCAG ACATCAAAGT ACCCTACAGG AGGACCAGTT CCCATCCGCA     2280

GACGTGAGGA CCTGGGCGAT GGCCAAAGGC TTAGTCCAAC ACCCACCGCG GGCCGCAGAG     2340

TCCGAGCTGG CCTTCCCCAG CTTCCTCCTG CAATGCTTCC TGGGGGCCCT GTGGCTGGCT     2400

CTGAGTGGCG AAATCAAGGA CAAGGAGCTC CCGCAGTACC TAGCATTGAC CCCAAGGAAG     2460
```

-continued

```
AAGAGGCCCT ATGACAACTG GCTGGAGGGC GTGCCACGCT TTCTGGCTGG GCTGATCTTC    2520

CAGCCTCCCG CCCGCTGCCT GGGAGCCCTA CTCGGGCCAT CGGCGGCTGC CTCGGTGGAC    2580

AGGAAGCAGA AGGTGCTTGC GAGGTACCTG AAGCGGCTGC AGCCGGGGAC ACTGCGGGCG    2640

CGGCAGCTGC TTGAGCTGCT GCACTGCGCC CACGAGGCCG AGGAGGCTGG AATTTGGCAG    2700

CACGTGGTAC AGGAGCTCCC CGGCCGCCTC TCTTTTCTGG GCACCCGCCT CACGCCTCCT    2760

GATGCACATG TACTGGGCAA GGCCTTGGAG GCGGCGGGCC AAGACTTCTC CCTGGACCTC    2820

CGCAGCACTG GCATTTGCCC CTCTGGATTG GGGAGCCTCG TGGGACTCAG CTGTGTCACC    2880

CGTTTCAGGG CTGCCTTGAG CGACACGGTG GCGCTGTGGG AGTCCCTGCG GCAGCATGGG    2940

GAGACCAAGC TACTTCAGGC AGCAGAGGAG AAGTTCACCA TCGAGCCTTT CAAAGCCAAG    3000

TCCCTGAAGG ATGTGGAAGA CCTGGGAAAG CTTGTGCAGA CTCAGAGGAC GAGAAGTTCC    3060

TCGGAAGACA CAGCTGGGGA GCTCCCTGCT GTTCGGGACC TAAAGAAACT GGAGTTTGCG    3120

CTGGGCCCTG TCTCAGGCCC CCAGGCTTTC CCCAAACTGG TGCGGATCCT CACGGCCTTT    3180

TCCTCCCTGC AGCATCTGGA CCTGGATGCG CTGAGTGAGA CAAGATCGG GGACGAGGGT    3240

GTCTCGCAGC TCTCAGCCAC CTTCCCCCAG CTGAAGTCCT TGGAAACCCT CAATCTGTCC    3300

CAGAACAACA TCACTGACCT GGGTGCCTAC AAACTCGCCG AGGCCCTGCC TTCGCTCGCT    3360

GCATCCCTGC TCAGGCTAAG CTTGTACAAT AACTGCATCT GCGACGTGGG AGCCGAGAGC    3420

TTGGCTCGTG TGCTTCCGGA CATGGTGTCC CTCCGGGTGA TGGACGCAAG TTCACGGCTG    3480

CCGGGGCCCA GCAGCTCGCT GCCAGCCTTC GGAGGTGTCC TCATGTGGAG ACGCTGGCGA    3540

TGTGGACGCC CACCATCCCA TTCAGTGTCC AGGAACACCT GCAACAACAG GATTCACGGA    3600

TCAGCCTGAG ATGATCCCAG CTGTGCTCTG GACAGGCATG TTCTCTGAGG ACACTAACCA    3660

CGCTGGACCT TGAACTGGGT ACTTGTGGAC ACAGCTCTTC TCCAGGCTGT ATCCCATGAG    3720

GCCTCAGCAT CCTGGCACCC GGCCCCTGCT GGTTCAGGGT TGGCCCCTGC CCGGCTGCGG    3780

AATGAACCAC ATCTTGCTCT GCTGACAGAC ACAGGCCCGG CTCCAGGCTC CTTTAGCGCC    3840

CAGTTGGGTG GATGCCTGGT GGCAGCTGCG GTCCACCCAG GAGCCCCGAG GCCTTCTCTG    3900

AAGGACATTG CGGACAGCCA CGGCCAGGCC AGAGGGAGTG ACAGAGGCAG CCCCATTCTG    3960

CCTGCCCAGG CCCCTGCCAC CCTGGGGAGA AAGTACTTCT TTTTTTTTAT TTTTAGACAG    4020

AGTCTCACTG TTGCCCAGGC TGGCGTGCAG TGGTGCGATC TGGGTTCACT GCAACCTCCG    4080

CCTCTTGGGT TCAAGCGATT CTTCTGCTTC AGCCTCCCGA GTAGCTGGGA CTACAGGCAC    4140

CCACCATCAT GTCTGGCTAA TTTTTCATTT TTAGTAGAGA CAGGGTTTTG CCATGTTGGC    4200

CAGGCTGGTC TCAAACTCTT GACCTCAGGT GATCCACCCA CCTCAGCCTC CCAAAGTGCT    4260

GGGGATTACA AGCGTGAGCC ACTGCACCGG GCCACAGAGA AAGTACTTCT CCACCCTGCT    4320

CTCCGACCAG ACACCTTGAC AGGGCACACC GGGCACTCAG AAGACACTGA TGGGCAACCC    4380

CCAGCCTGCT AATTCCCCAG ATTGCAACAG GCTGGGCTTC AGTGGCAGGC TGCTTTTGTC    4440

TATGGGACTC AATGCACTGA CATTGTTGGC CAAAGCCAAA GCTAGGCCTG GCCAGATGCA    4500

CCAGGCCCTT AGCAGGGAAA CAGCTAATGG GACACTAATG GGGCGGTGAG AGGGGAACAG    4560

ACTGGAAGCA CAGCTTCATT TCCTGTGTCT TTTTTCACTA CATTATAAAT GTCTCTTTAA    4620

TGTCACAAAA AAAAAAAAA AAAAAAAA                                       4649
```

(2) INFORMATION FOR SEQ ID NO: 12:

(i) SEQUENCE CHARACTERISTICS:
        (A) LENGTH: 4346 base pairs (B) TYPE: nucleic acid
(C) STRANDEDNESS: single
(D) TOPOLOGY: linear (ii) MOLECULE TYPE: DNA (genomic)

(ix) FEATURE:
(A) NAME/KEY: cIIta of type II (xi) SEQUENCE DESCRIPTION: SEQ ID NO: 12:

```
ATGGAGTTGG GGCCCCTAGA AGGTGGCTAC CTGGAGCTTC TTAACAGCGA TGCTGACCCC     60
CTGTGCCTCT ACCACTTCTA TGACCAGATG GACCTGGCTG GAGAAGAAGA GATTGAGCTC    120
TACTCAGAAC CCGACACAGA CACCATCAAC TGCGACCAGT TCAGCAGGCT GTTGTGTGAC    180
ATGGAAGGTG ATGAAGAGAC CAGGGAGGCT TATGCCAATA TCGCGGAACT GGACCAGTAT    240
GTCTTCCAGG ACTCCCAGCT GGAGGGCCTG AGCAAGGACA TTTTCAAGCA CATAGGACCA    300
GATGAAGTGA TCGGTGAGAG TATGGAGATG CCAGCAGAAG TTGGGCAGAA AAGTCAGAAA    360
AGACCCTTCC AGAGGAGCT TCCGGCAGAC CTGAAGCACT GGAAGCCAGC TGAGCCCCCC    420
ACTGTGGTGA CTGGCAGTCT CCTAGTGGGA CCAGTGAGCG ACTGCTCCAC CCTGCCCTGC    480
CTGCCACTGC CTGCGCTGTT CAACCAGGAG CCAGCCTCCG GCCAGATGCG CCTGGAGAAA    540
ACCGACCAGA TTCCCATGCC TTTCTCCAGT TCCTCGTTGA GCTGCCTGAA TCTCCCTGAG    600
GGACCCATCC AGTTTGTCCC CACCATCTCC ACTCTGCCCC ATGGGCTCTG GCAAATCTCT    660
GAGGCTGGAA CAGGGGTCTC CAGTATATTC ATCTACCATG GTGAGGTGCC CCAGGCCAGC    720
CAAGTACCCC CTCCCAGTGG ATTCACTGTC CACGGCCTCC AACATCTCC AGACCGGCCA    780
GGCTCCACCA GCCCCTTCGC TCCATCAGCC ACTGACCTGC CAGCATGCC TGAACCTGCC    840
CTGACCTCCC GAGCAAACAT GACAGAGCAC AAGACGTCCC CCACCCAATG CCCGGCAGCT    900
GGAGAGGTCT CCAACAAGCT TCCAAAATGG CCTGAGCCGG TGGAGCAGTT CTACCGCTCA    960
CTGCAGGACA CGTATGGTGC CGAGCCCGCA GGCCCGGATG GCATCCTAGT GGAGGTGGAT   1020
CTGGTGCAGG CCAGGCTGGA GAGGAGCAGC AGCAAGAGCC TGGAGCGGGA ACTGGCCACC   1080
CCGGACTGGG CAGAACGGCA GCTGGCCCAA GGAGGCCTGG CTGAGGTGCT GTTGGCTGCC   1140
AAGGAGCACC GGCGGCCGCG TGAGACACGA GTGATTGCTG TGCTGGGCAA AGCTGGTCAG   1200
GGCAAGAGCT ATTGGGCTGG GGCAGTGAGC CGGGCCTGGG CTTGTGGCCG GCTTCCCCGC   1260
TACGACTTTG TCTTCTCTGT CCCCTGCCAT TGCTTGAACC GTCCGGGGGA TGCCTATGTC   1320
CTGCAGGATC TGCTCTTCTC CCTGGGCCCA CAGCCACTCG TGGCGGCCGA TGAGGTTTTG   1380
AGCCACATCT TGAAGAGACC TGACCGCGTT CTGCTCATCC TAGACGCCTT CGAGGAGCCC   1440
GAAGCGCAAG ATGGCTTCCT GCACAGCACG TGCGGACCGG CACCGGCGGA GCCCTGCTTC   1500
CTCCGGGGGC TGCTGGCCGG CCTTTTCCAG AAGAAGCTGC TCCGAGGTTG CACCCTCCTC   1560
CTCACAGCCC GGCCCCGGGG CCGCCTGGTC CAGAGCCTGA GCAAGGCCGA CGCCCTATTT   1620
GAGCTGTCCG GCTTCTCCAT GGAGCAGGCC CAGGCATACG TGATGCGCTA CTTTGAGAGC   1680
TCAGGGATGA CAGAGCACCA AGACAGAGCC CTGACGCTCC TCCGGGACCG GCCACTTCTT   1740
CTCAGTCACA GCCACAGCCC TACTTTGTGC CGGGCAGTGT GCCAGCTCTC AGAGGCCCTG   1800
CTGGAGCTTG GGGAGGACGC CAAGCTGCCC TCCACGCTCA CGGGACTCTA TGTCGGCCTG   1860
CTGGGCCGTG CAGCCCTCGA CAGCCCCCCC GGGGCCCTGG CAGAGCTGGC CAAGCTGGCC   1920
TGGGAGCTGG GCCGCAGACA TCAAAGTACC CTACAGGAGG ACCAGTTCCC ATCCGCAGAC   1980
GTGAGGACCT GGGCGATGGC CAAAGGCTTA GTCCAACACC CACCGCGGGC CGCAGAGTCC   2040
```

```
GAGCTGGCCT TCCCCAGCTT CCTCCTGCAA TGCTTCCTGG GGGCCCTGTG GCTGGCTCTG      2100

AGTGGCGAAA TCAAGGACAA GGAGCTCCCG CAGTACCTAG CATTGACCCC AAGGAAGAAG      2160

AGGCCCTATG ACAACTGGCT GGAGGGCGTG CCACGCTTTC TGGCTGGGCT GATCTTCCAG      2220

CCTCCCGCCC GCTGCCTGGG AGCCCTACTC GGGCCATCGG CGGCTGCCTC GGTGGACAGG      2280

AAGCAGAAGG TGCTTGCGAG GTACCTGAAG CGGCTGCAGC CGGGGACACT GCGGGCGCGG      2340

CAGCTGCTTG AGCTGCTGCA CTGCGCCCAC GAGGCCGAGG AGGCTGGAAT TTGGCAGCAC      2400

GTGGTACAGG AGCTCCCCGG CCGCCTCTCT TTTCTGGGCA CCCGCCTCAC GCCTCCTGAT      2460

GCACATGTAC TGGGCAAGGC CTTGGAGGCG GCGGGCCAAG ACTTCTCCCT GGACCTCCGC      2520

AGCACTGGCA TTTGCCCCTC TGGATTGGGG AGCCTCGTGG GACTCAGCTG TGTCACCCGT      2580

TTCAGGGCTG CCTTGAGCGA CACGGTGGCG CTGTGGGAGT CCCTGCGGCA GCATGGGGAG      2640

ACCAAGCTAC TTCAGGCAGC AGAGGAGAAG TTCACCATCG AGCCTTTCAA AGCCAAGTCC      2700

CTGAAGGATG TGGAAGACCT GGGAAAGCTT GTGCAGACTC AGAGGACGAG AAGTTCCTCG      2760

GAAGACACAG CTGGGGAGCT CCCTGCTGTT CGGGACCTAA AGAAACTGGA GTTTGCGCTG      2820

GGCCCTGTCT CAGGCCCCCA GGCTTTCCCC AAACTGGTGC GGATCCTCAC GGCCTTTTCC      2880

TCCCTGCAGC ATCTGGACCT GGATGCGCTG AGTGAGAACA AGATCGGGGA CGAGGGTGTC      2940

TCGCAGCTCT CAGCCACCTT CCCCCAGCTG AAGTCCTTGG AAACCCTCAA TCTGTCCCAG      3000

AACAACATCA CTGACCTGGG TGCCTACAAA CTCGCCGAGG CCCTGCCTTC GCTCGCTGCA      3060

TCCCTGCTCA GGCTAAGCTT GTACAATAAC TGCATCTGCG ACGTGGGAGC CGAGAGCTTG      3120

GCTCGTGTGC TTCCGGACAT GGTGTCCCTC CGGGTGATGG ACGCAAGTTC ACGGCTGCCG      3180

GGGCCCAGCA GCTCGCTGCC AGCCTTCGGA GGTGTCCTCA TGTGGAGACG CTGGCGATGT      3240

GGACGCCCAC CATCCCATTC AGTGTCCAGG AACACCTGCA ACAACAGGAT TCACGGATCA      3300

GCCTGAGATG ATCCCAGCTG TGCTCTGGAC AGGCATGTTC TCTGAGGACA CTAACCACGC      3360

TGGACCTTGA ACTGGGTACT TGTGGACACA GCTCTTCTCC AGGCTGTATC CCATGAGGCC      3420

TCAGCATCCT GGCACCCGGC CCCTGCTGGT TCAGGGTTGG CCCCTGCCCG GCTGCGGAAT      3480

GAACCACATC TTGCTCTGCT GACAGACACA GGCCCGGCTC CAGGCTCCTT TAGCGCCCAG      3540

TTGGGTGGAT GCCTGGTGGC AGCTGCGGTC CACCCAGGAG CCCCGAGGCC TTCTCTGAAG      3600

GACATTGCGG ACAGCCACGG CCAGGCCAGA GGGAGTGACA GAGGCAGCCC CATTCTGCCT      3660

GCCCAGGCCC CTGCCACCCT GGGGAGAAAG TACTTCTTTT TTTTTATTTT TAGACAGAGT      3720

CTCACTGTTG CCCAGGCTGG CGTGCAGTGG TGCGATCTGG GTTCACTGCA ACCTCCGCCT      3780

CTTGGGTTCA AGCGATTCTT CTGCTTCAGC CTCCCGAGTA GCTGGGACTA CAGGCACCCA      3840

CCATCATGTC TGGCTAATTT TTCATTTTTA GTAGAGACAG GGTTTTGCCA TGTTGGCCAG      3900

GCTGGTCTCA AACTCTTGAC CTCAGGTGAT CCACCCACCT CAGCCTCCCA AAGTGCTGGG      3960

GATTACAAGC GTGAGCCACT GCACCGGGCC ACAGAGAAAG TACTTCTCCA CCCTGCTCTC      4020

CGACCAGACA CCTTGACAGG GCACACCGGG CACTCGAAGG ACACTGATGG GCAACCCCCA      4080

GCCTGCTAAT TCCCCAGATT GCAACAGGCT GGGCTTCAGT GGCAGGCTGC TTTTGTCTAT      4140

GGGACTCAAT GCACTGACAT TGTTGGCCAA AGCCAAAGCT AGGCCTGGCC AGATGCACCA      4200

GGCCCTTAGC AGGGAAACAG CTAATGGGAC ACTAATGGGG CGGTGAGAGG GGAACAGACT      4260

GGAAGCACAG CTTCATTTCC TGTGTCTTTT TTCACTACAT TATAAATGTC TCTTTAATGT      4320

CACAAAAAAA AAAAAAAAA AAAAA                                            4346
```

(2) INFORMATION FOR SEQ ID NO: 13:

(i) SEQUENCE CHARACTERISTICS:
        (A) LENGTH: 4418 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: cIIta of type III (xi) SEQUENCE DESCRIPTION: SEQ ID NO: 13:

```
ATGCGTTGCC TGGCTCCACG CCCTGCTGGG TCCTACCTGT CAGAGCCCCA AGGCAGCTCA      60

CAGTGTGCCA CCATGGAGTT GGGGCCCCTA GAAGGTGGCT ACCTGGAGCT TCTTAACAGC     120

GATGCTGACC CCCTGTGCCT CTACCACTTC TATGACCAGA TGGACCTGGC TGGAGAAGAA     180

GAGATTGAGC TCTACTCAGA ACCCGACACA GACACCATCA ACTGCGACCA GTTCAGCAGG     240

CTGTTGTGTG ACATGGAAGG TGATGAAGAG ACCAGGGAGG CTTATGCCAA TATCGCGGAA     300

CTGGACCAGT ATGTCTTCCA GGACTCCCAG CTGGAGGGCC TGAGCAAGGA CATTTTCAAG     360

CACATAGGAC CAGATGAAGT GATCGGTGAG AGTATGGAGA TGCCAGCAGA AGTTGGGCAG     420

AAAAGTCAGA AAAGACCCTT CCCAGAGGAG CTTCCGGCAG ACCTGAAGCA CTGGAAGCCA     480

GCTGAGCCCC CCACTGTGGT GACTGGCAGT CTCCTAGTGG ACCAGTGAG CGACTGCTCC      540

ACCCTGCCCT GCCTGCCACT GCCTGCGCTG TTCAACCAGG AGCCAGCCTC CGGCCAGATG     600

CGCCTGGAGA AAACCGACCA GATTCCCATG CCTTTCTCCA GTTCCTCGTT GAGCTGCCTG     660

AATCTCCCTG AGGGACCCAT CCAGTTTGTC CCCACCATCT CCACTCTGCC CATGGGCTC      720

TGGCAAATCT CTGAGGCTGG AACAGGGGTC TCCAGTATAT TCATCTACCA TGGTGAGGTG     780

CCCCAGGCCA GCCAAGTACC CCCTCCCAGT GGATTCACTG TCCACGGCCT CCCAACATCT     840

CCAGACCGGC CAGGCTCCAC CAGCCCCTTC GCTCCATCAG CCACTGACCT GCCCAGCATG     900

CCTGAACCTG CCCTGACCTC CCGAGCAAAC ATGACAGAGC ACAAGACGTC CCCCACCCAA     960

TGCCCGGCAG CTGGAGAGGT CTCCAACAAG CTTCCAAAAT GGCCTGAGCC GGTGGAGCAG    1020

TTCTACCGCT CACTGCAGGA CACGTATGGT GCCGAGCCCG CAGGCCCGGA TGGCATCCTA    1080

GTGGAGGTGG ATCTGGTGCA GGCCAGGCTG GAGAGGAGCA GCAGCAAGAG CCTGGAGCGG    1140

GAACTGGCCA CCCCGGACTG GGCAGAACGG CAGCTGGCCC AAGGAGGCCT GGCTGAGGTG    1200

CTGTTGGCTG CCAAGGAGCA CCGGCGGCCG CGTGAGACAC GAGTGATTGC TGTGCTGGGC    1260

AAAGCTGGTC AGGGCAAGAG CTATTGGGCT GGGGCAGTGA GCCGGGCCTG GCTTGTGGC     1320

CGGCTTCCCC AGTACGACTT TGTCTTCTCT GTCCCCTGCC ATTGCTTGAA CCGTCCGGGG    1380

GATGCCTATG GCCTGCAGGA TCTGCTCTTC TCCCTGGGCC CACAGCCACT CGTGGCGGCC    1440

GATGAGGTTT TCAGCCACAT CTTGAAGAGA CCTGACCGCG TTCTGCTCAT CCTAGACGCC    1500

TTCGAGGAGC TGGAAGCGCA AGATGGCTTC CTGCACAGCA CGTGCGGACC GGCACCGGCG    1560

GAGCCCTGCT CCCTCCGGGG GCTGCTGGCC GGCCTTTTCC AGAAGAAGCT GCTCCGAGGT    1620

TGCACCCTCC TCCTCACAGC CCGGCCCCGG GGCCGCCTGG TCCAGAGCCT GAGCAAGGCC    1680

GACGCCCTAT TTGAGCTGTC CGGCTTCTCC ATGGAGCAGG CCCAGGCATA CGTGATGCGC    1740

TACTTTGAGA GCTCAGGGAT GACAGAGCAC CAAGACAGAG CCCTGACGCT CCTCCGGGAC    1800

CGGCCACTTC TTTCTCAGTCA CAGCCACAGC CCTACTTTGT GCCGGGCAGT GTGCCAGCTC    1860

TCAGAGGCCC TGCTGGAGCT TGGGGAGGAC GCCAAGCTGC CCTCCACGCT CACGGGACTC    1920
```

-continued

| | |
|---|---|
| TATGTCGGCC TGCTGGGCCG TGCAGCCCTC GACAGCCCCC CCGGGGCCCT GGCAGAGCTG | 1980 |
| GCCAAGCTGG CCTGGGAGCT GGGCCGCAGA CATCAAAGTA CCCTACAGGA GGACCAGTTC | 2040 |
| CCATCCGCAG ACGTGAGGAC CTGGGCGATG GCCAAAGGCT TAGTCCAACA CCCACCGCGG | 2100 |
| GCCGCAGAGT CCGAGCTGGC CTTCCCCAGC TTCCTCCTGC AATGCTTCCT GGGGGCCCTG | 2160 |
| TGGCTGGCTC TGAGTGGCGA AATCAAGGAC AAGGAGCTCC CGCAGTACCT AGCATTGACC | 2220 |
| CCAAGGAAGA AGAGGCCCTA TGACAACTGG CTGGAGGGCG TGCCACGCTT TCTGGCTGGG | 2280 |
| CTGATCTTCC AGCCTCCCGC CCGCTGCCTG GGAGCCCTAC TCGGGCCATC GGCGGCTGCC | 2340 |
| TCGGTGGACA GGAAGCAGAA GGTGCTTGCG AGGTACCTGA AGCGGCTGCA GCCGGGGACA | 2400 |
| CTGCGGGCGC GGCAGCTGCT TGAGCTGCTG CACTGCGCCC ACGAGGCCGA GGAGGCTGGA | 2460 |
| ATTTGGCAGC ACGTGGTACA GGAGCTCCCC GGCCGCCTCT CTTTTCTGGG CACCCGCCTC | 2520 |
| ACGCCTCCTG ATGCACATGT ACTGGGCAAG GCCTTGGAGG CGGCGGGCCA AGACTTCTCC | 2580 |
| CTGGACCTCC GCAGCACTGG CATTTGCCCC TCTGGATTGG GGAGCCTCGT GGGACTCAGC | 2640 |
| TGTGTCACCC GTTTCAGGGC TGCCTTGAGC GACACGGTGG CGCTGTGGGA GTCCCTGCGG | 2700 |
| CAGCATGGGG AGACCAAGCT ACTTCAGGCA GCAGAGGAGA AGTTCACCAT CGAGCCTTTC | 2760 |
| AAAGCCAAGT CCCTGAAGGA TGTGGAAGAC CTGGGAAAGC TTGTGCAGAC TCAGAGGACG | 2820 |
| AGAAGTTCCT CGGAAGACAC AGCTGGGGAG CTCCCTGCTG TTCGGGACCT AAAGAAACTG | 2880 |
| GAGTTTGCGC TGGGCCCTGT CTCAGGCCCC CAGGCTTTCC CCAAACTGGT GCGGATCCTC | 2940 |
| ACGGCCTTTT CCTCCCTGCA GCATCTGGAC CTGGATGCGC TGAGTGAGAA CAAGATCGGG | 3000 |
| GACGAGGGTG TCTCGCAGCT CTCAGCCACC TTCCCCCAGC TGAAGTCCTT GGAAACCCTC | 3060 |
| AATCTGTCCC AGAACAACAT CACTGACCTG GGTGCCTACA AACTCGCCGA GGCCCTGCCT | 3120 |
| TCGCTCGCTG CATCCCTGCT CAGGCTAAGC TTGTACAATA ACTGCATCTG CGACGTGGGA | 3180 |
| GCCGAGAGCT TGGCTCGTGT GCTTCCGGAC ATGGTGTCCC TCCGGGTGAT GGACGCAAGT | 3240 |
| TCACGGCTGC CGGGGCCCAG CAGCTCGCTG CCAGCCTTCG GAGGTGTCCT CATGTGGAGA | 3300 |
| CGCTGGCGAT GTGACGCCC ACCATCCCAT TCAGTGTCCA GGAACACCTG CAACAACAGG | 3360 |
| ATTCACGGAT CAGCCTGAGA TGATCCCAGC TGTGCTCTGG ACAGGCATGT TCTCTGAGGA | 3420 |
| CACTAACCAC GCTGGACCTT GAACTGGGTA CTTGTGGACA CAGCTCTTCT CCAGGCTGTA | 3480 |
| TCCCATGAGG CCTCAGCATC CTGGCACCCG GCCCCTGCTG GTTCAGGGTT GGCCCCTGCC | 3540 |
| CGGCTGCGGA ATGAACCACA TCTTGCTCTG CTGACAGACA CAGGCCCGGC TCCAGGCTCC | 3600 |
| TTTAGCGCCC AGTTGGGTGG ATGCCTGGTG GCAGCTGCGG TCCACCCAGG AGCCCCGAGG | 3660 |
| CCTTCTCTGA AGGACATTGC GGACAGCCAC GGCCAGGCCA GAGGGAGTGA CAGAGGCAGC | 3720 |
| CCCATTCTGC CTGCCCAGGC CCCTGCCACC CTGGGGAGAA AGTACTTCTT TTTTTTTATT | 3780 |
| TTTAGACAGA GTCTCACTGT TGCCCAGGCT GGCGTGCAGT GGTGCGATCT GGGTTCACTG | 3840 |
| CAACCTCCGC CTCTTGGGTT CAAGCGATTC TTCTGCTTCA GCCTCCCGAG TAGCTGGGAC | 3900 |
| TACAGGCACC CACCATCATG TCTGGCTAAT TTTTCATTTT TAGTAGAGAC AGGGTTTTGC | 3960 |
| CATGTTGGCC AGGCTGGTCT CAAACTCTTG ACCTCAGGTG ATCCACCCAC CTCAGCCTCC | 4020 |
| CAAAGTGCTG GGATTACAA GCGTGAGCCA CTGCACCGGG CCACAGAGAA AGTACTTCTC | 4080 |
| CACCCTGCTC TCCGACCAGA CACCTTGACA GGGCACACCG GCACTCAGA AGACACTGAT | 4140 |
| GGGCAACCCC CAGCCTGCTA ATTCCCCAGA TTGCAACAGG CTGGGCTTCA GTGGCAGGCT | 4200 |
| GCTTTTGTCT ATGGGACTCA ATGCACTGAC ATTGTTGGCC AAAGCCAAAG CTAGGCCTGG | 4260 |
| CCAGATGCAC CAGGCCCTTA GCAGGGAAAC AGCTAATGGG ACACTAATGG GGCGGTGAGA | 4320 |

```
GGGGAACAGA CTGGAAGCAC AGCTTCATTT CCTGTGTCTT TTTTCACTAC ATTATAAATG      4380

TCTCTTTAAT GTCACAAAAA AAAAAAAAAA AAAAAAAA                              4418

(2) INFORMATION FOR SEQ ID NO: 14:

(i) SEQUENCE CHARACTERISTICS:
        (A) LENGTH: 4366 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: cIIta of type IV (xi) SEQUENCE DESCRIPTION: SEQ ID NO: 14:

GCAGCTCACA GTGTGCCACC ATGGAGTTGG GGCCCCTAGA AGGTGGCTAC CTGGAGCTTC        60

TTAACAGCGA TGCTGACCCC CTGTGCCTCT ACCACTTCTA TGACCAGATG GACCTGGCTG       120

GAGAAGAAGA GATTGAGCTC TACTCAGAAC CCGACACAGA CACCATCAAC TGCGACCAGT       180

TCAGCAGGCT GTTGTGTGAC ATGGAAGGTG ATGAAGAGAC CAGGGAGGCT TATGCCAATA       240

TCGCGGAACT GGACCAGTAT GTCTTCCAGG ACTCCCAGCT GGAGGGCCTG AGCAAGGACA       300

TTTTCAAGCA CATAGGACCA GATGAAGTGA TCGGTGAGAG TATGGAGATG CCAGCAGAAG       360

TTGGGCAGAA AAGTCAGAAA AGACCCTTCC CAGAGGAGCT TCCGGCAGAC CTGAAGCACT       420

GGAAGCCAGC TGAGCCCCCC ACTGTGGTGA CTGGCAGTCT CCTAGTGGGA CCAGTGAGCG       480

ACTGCTCCAC CCTGCCCTGC CTGCCACTGC CTGCGCTGTT CAACCAGGAG CCAGCCTCCG       540

GCCAGATGCG CCTGGAGAAA ACCGACCAGA TTCCCATGCC TTTCTCCAGT TCCTCGTTGA       600

GCTGCCTGAA TCTCCCTGAG GGACCCATCC AGTTTGTCCC CACCATCTCC ACTCTGCCCC       660

ATGGGCTCTG GCAAATCTCT GAGGCTGGAA CAGGGGTCTC CAGTATATTC ATCTACCATG       720

GTGAGGTGCC CCAGGCCAGC CAAGTACCCC CTCCCAGTGG ATTCACTGTC CACGGCCTCC       780

CAACATCTCC AGACCGGCCA GGCTCCACCA GCCCCTTCGC TCCATCAGCC ACTGACCTGC       840

CCAGCATGCC TGAACCTGCC CTGACCTCCC GAGCAAACAT GACAGAGCAC AAGACGTCCC       900

CCACCCAATG CCCGGCAGCT GGAGAGGTCT CCAACAAGCT TCCAAAATGG CCTGAGCCGG       960

TGGAGCAGTT CTACCGCTCA CTGCAGGACA CGTATGGTGC CGAGCCCGCA GGCCCGGATG      1020

GCATCCTAGT GGAGGTGGAT CTGGTGCAGG CCAGGCTGGA GAGGAGCAGC AGCAAGAGCC      1080

TGGAGCGGGA ACTGGCCACC CCGGACTGGG CAGAACGGCA GCTGGCCCAA GGAGGCCTGG      1140

CTGAGGTGCT GTTGGCTGCC AAGGAGCACC GGCGGCCGCG TGAGACACGA GTGATTGCTG      1200

TGCTGGGCAA AGCTGGTCAG GGCAAGAGCT ATTGGGCTGG GGCAGTGAGC CGGGCCTGGG      1260

CTTGTGGCCG GCTTCCCCAG TACGACTTTG TCTTCTCTGT CCCCTGCCAT TGCTTGAACC      1320

GTCCGGGGGA TGCCTATGGC CTGCAGGATC TGCTCTTCTC CCTGGGCCCA CAGCCACTCG      1380

TGGCGGCCGA TGAGGTTTTC AGCCACATCT TGAAGAGACC TGACCGCGTT CTGCTCATCC      1440

TAGACGCCTT CGAGGAGCTG GAAGCGCAAG ATGGCTTCCT GCACAGCACG TGCGGACCGG      1500

CACCGGCGGA GCCCTGCTCC CTCCGGGGGC TGCTGGCCGG CCTTTTCCAG AAGAAGCTGC      1560

TCCGAGGTTG CACCCTCCTC CTCACAGCCC GGCCCCGGGG CCGCCTGGTC CAGAGCCTGA      1620

GCAAGGCCGA CGCCCTATTT GAGCTGTCCG GCTTCTCCAT GGAGCAGGCC CAGGCATACG      1680

TGATGCGCTA CTTTGAGAGC TCAGGGATGA CAGAGCACCA AGACAGAGCC CTGACGCTCC      1740
```

-continued

```
TCCGGGACCG GCCACTTCTT CTCAGTCACA GCCACAGCCC TACTTTGTGC CGGGCAGTGT    1800

GCCAGCTCTC AGAGGCCCTG CTGGAGCTTG GGAGGACGC CAAGCTGCCC TCCACGCTCA     1860

CGGGACTCTA TGTCGGCCTG CTGGGCCGTG CAGCCCTCGA CAGCCCCCCC GGGGCCCTGG    1920

CAGAGCTGGC CAAGCTGGCC TGGGAGCTGG GCCGCAGACA TCAAAGTACC CTACAGGAGG    1980

ACCAGTTCCC ATCCGCAGAC GTGAGGACCT GGGCGATGGC CAAAGGCTTA GTCCAACACC    2040

CACCGCGGGC CGCAGAGTCC GAGCTGGCCT TCCCCAGCTT CCTCCTGCAA TGCTTCCTGG    2100

GGGCCCTGTG GCTGGCTCTG AGTGGCGAAA TCAAGGACAA GGAGCTCCCG CAGTACCTAG    2160

CATTGACCCC AAGGAAGAAG AGGCCCTATG ACAACTGGCT GGAGGGCGTG CCACGCTTTC    2220

TGGCTGGGCT GATCTTCCAG CCTCCCGCCC GCTGCCTGGG AGCCCTACTC GGGCCATCGG    2280

CGGCTGCCTC GGTGGACAGG AAGCAGAAGG TGCTTGCGAG GTACCTGAAG CGGCTGCAGC    2340

CGGGGACACT GCGGGCGCGG CAGCTGCTTG AGCTGCTGCA CTGCGCCCAC GAGGCCGAGG    2400

AGGCTGGAAT TTGGCAGCAC GTGGTACAGG AGCTCCCCGG CCGCCTCTCT TTTCTGGGCA    2460

CCCGCCTCAC GCCTCCTGAT GCACATGTAC TGGGCAAGGC CTTGGAGGCG GCGGGCCAAG    2520

ACTTCTCCCT GGACCTCCGC AGCACTGGCA TTTGCCCCTC TGGATTGGGG AGCCTCGTGG    2580

GACTCAGCTG TGTCACCCGT TTCAGGGCTG CCTTGAGCGA CACGGTGGCG CTGTGGGAGT    2640

CCCTGCGGCA GCATGGGGAG ACCAAGCTAC TTCAGGCAGC AGAGGAGAAG TTCACCATCG    2700

AGCCTTTCAA AGCCAAGTCC CTGAAGGATG TGGAAGACCT GGGAAAGCTT GTGCAGACTC    2760

AGAGGACGAG AAGTTCCTCG GAAGACACAG CTGGGGAGCT CCCTGCTGTT CGGGACCTAA    2820

AGAAACTGGA GTTTGCGCTG GGCCCTGTCT CAGGCCCCCA GGCTTTCCCC AAACTGGTGC    2880

GGATCCTCAC GGCCTTTTCC TCCCTGCAGC ATCTGGACCT GGATGCGCTG AGTGAGAACA    2940

AGATCGGGGA CGAGGGTGTC TCGCAGCTCT CAGCCACCTT CCCCCAGCTG AAGTCCTTGG    3000

AAACCCTCAA TCTGTCCCAG AACAACATCA CTGACCTGGG TGCCTACAAA CTCGCCGAGG    3060

CCCTGCCTTC GCTCGCTGCA TCCCTGCTCA GGCTAAGCTT GTACAATAAC TGCATCTGCG    3120

ACGTGGGAGC CGAGAGCTTG GCTCGTGTGC TTCCGGACAT GGTGTCCCTC CGGGTGATGG    3180

ACGCAAGTTC ACGGCTGCCG GGGCCCAGCA GCTCGCTGCC AGCCTTCGGA GGTGTCCTCA    3240

TGTGGAGACG CTGGCGATGT GGACGCCCAC CATCCCATTC AGTGTCCAGG AACACCTGCA    3300

ACAACAGGAT TCACGGATCA GCCTGAGATG ATCCCAGCTG TGCTCTGGAC AGGCATGTTC    3360

TCTGAGGACA CTAACCACGC TGGACCTTGA ACTGGGTACT TGTGGACACA GCTCTTCTCC    3420

AGGCTGTATC CCATGAGGCC TCAGCATCCT GGCACCCGGC CCCTGCTGGT TCAGGGTTGG    3480

CCCCTGCCCG GCTGCGGAAT GAACCACATC TTGCTCTGCT GACAGACACA GGCCCGGCTC    3540

CAGGCTCCTT TAGCGCCCAG TTGGGTGGAT GCCTGGTGGC AGCTGCGGTC CACCCAGGAG    3600

CCCCGAGGCC TTCTCTGAAG GACATTGCGG ACAGCCACGG CCAGGCCAGA GGGAGTGACA    3660

GAGGCAGCCC CATTCTGCCT GCCCAGGCCC CTGCCACCCT GGGGAGAAAG TACTTCTTTT    3720

TTTTTATTTT TAGACAGAGT CTCACTGTTG CCCAGGCTGG CGTGCAGTGG TGCGATCTGG    3780

GTTCACTGCA ACCTCCGCCT CTTGGGTTCA AGCGATTCTT CTGCTTCAGC CTCCCGAGTA    3840

GCTGGGACTA CAGGCACCCA CCATCATGTC TGGCTAATTT TTCATTTTTA GTAGAGACAG    3900

GGTTTTGCCA TGTTGGCCAG GCTGGTCTCA AACTCTTGAC CTCAGGTGAT CCACCCACCT    3960

CAGCCTCCCA AAGTGCTGGG GATTACAAGC GTGAGCCACT GCACCGGGCC ACAGAGAAAG    4020

TACTTCTCCA CCCTGCTCTC CGACCAGACA CCTTGACAGG GCACACCGGG CACTCAGAAG    4080

ACACTGATGG GCAACCCCCA GCCTGCTAAT TCCCCAGATT GCAACAGGCT GGGCTTCAGT    4140
```

```
GGCAGGCTGC TTTTGTCTAT GGGACTCAAT GCACTGACAT TGTTGGCCAA AGCCAAAGCT      4200

AGGCCTGGCC AGATGCACCA GGCCCTTAGC AGGGAAACAG CTAATGGGAC ACTAATGGGG      4260

CGGTGAGAGG GGAACAGACT GGAAGCACAG CTTCATTTCC TGTGTCTTTT TTCACTACAT      4320

TATAAATGTC TCTTTAATGT CACAAAAAAA AAAAAAAAA AAAAAA                     4366

(2) INFORMATION FOR SEQ ID NO: 15:

(i) SEQUENCE CHARACTERISTICS:
        (A) LENGTH: 2480 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: 901-3390

(xi) SEQUENCE DESCRIPTION: SEQ ID NO: 15:

CCTGAACCTG CCCTGACCTC CCGAGCAAAC ATGACAGAGC ACAAGACGTC CCCCACCCAA        60

TGCCCGGCAG CTGGAGAGGT CTCCAACAAG CTTCCAAAAT GGCCTGAGCC GGTGGAGCAG       120

TTCTACCGCT CACTGCAGGA CACGTATGGT GCCGAGCCCG CAGGCCCGGA TGGCATCCTA       180

GTGGAGGTGG ATCTGGTGCA GGCCAGGCTG GAGAGGAGCA GCAGCAAGAG CCTGGAGCGG       240

GAACTGGCCA CCCCGGACTG GCAGAACGG CAGCTGGCCC AAGGAGGCCT GGCTGAGGTG        300

CTGTTGGCTG CCAAGGAGCA CCGGCGGCCG CGTGAGACAC GAGTGATTGC TGTGCTGGGC       360

AAAGCTGGTC AGGGCAAGAG CTATTGGGCT GGGGCAGTGA GCCGGGCCTG GCTTGTGGC        420

CGGCTTCCCC AGTACGACTT TGTCTTCTCT GTCCCCTGCC ATTGCTTGAA CCGTCCGGGG       480

GATGCCTATG GCCTGCAGGA TCTGCTCTTC TCCCTGGGCC ACAGCCACT CGTGGCGGCC       540

GATGAGGTTT TCAGCCACAT CTTGAAGAGA CCTGACCGCG TTCTGCTCAT CCTAGACGCC       600

TTCGAGGAGC TGGAAGCGCA AGATGGCTTC CTGCACAGCA CGTGCGGACC GGCACCGGCG       660

GAGCCCTGCT CCCTCCGGGG GCTGCTGGCC GGCCTTTTCC AGAAGAAGCT GCTCCGAGGT       720

TGCACCCTCC TCCTCACAGC CCGGCCCCGG GGCCGCCTGG TCCAGAGCCT GAGCAAGGCC       780

GACGCCCTAT TTGAGCTGTC CGGCTTCTCC ATGGAGCAGG CCCAGGCATA CGTGATGCGC       840

TACTTTGAGA GCTCAGGGAT GACAGAGCAC CAAGACAGAG CCCTGACGCT CCTCCGGGAC       900

CGGCCACTTC TTTCTCAGTCA CAGCCACAGC CCTACTTTGT GCCGGGCAGT GTGCCAGCTC       960

TCAGAGGCCC TGCTGGAGCT TGGGGAGGAC GCCAAGCTGC CCTCCACGCT CACGGGACTC      1020

TATGTCGGCC TGCTGGGCCG TGCAGCCCTC GACAGCCCCC CCGGGGCCCT GGCAGAGCTG      1080

GCCAAGCTGG CCTGGGAGCT GGGCCGCAGA CATCAAAGTA CCCTACAGGA GGACCAGTTC      1140

CCATCCGCAG ACGTGAGGAC CTGGGCGATG GCCAAAGGCT TAGTCCAACA CCCACCGCGG      1200

GCCGCAGAGT CCGAGCTGGC CTTCCCCAGC TTCCTCCTGC AATGCTTCCT GGGGGCCCTG      1260

TGGCTGGCTC TGAGTGGCGA AATCAAGGAC AAGGAGCTCC CGCAGTACCT AGCATTGACC      1320

CCAAGGAAGA AGAGGCCCTA TGACAACTGG CTGGAGGGCG TGCCACGCTT TCTGGCTGGG      1380

CTGATCTTCC AGCCTCCCGC CCGCTGCCTG GGAGCCCTAC TCGGGCCATC GGCGGCTGCC      1440

TCGGTGGACA GGAAGCAGAA GGTGCTTGCG AGGTACCTGA AGCGGCTGCA GCCGGGGACA      1500

CTGCGGGCGC GGCAGCTGCT TGAGCTGCTG CACTGCGCCC ACGAGGCCGA GGAGGCTGGA      1560

ATTTGGCAGC ACGTGGTACA GGAGCTCCCC GGCCGCCTCT CTTTTCTGGG CACCCGCCTC      1620
```

```
ACGCCTCCTG ATGCACATGT ACTGGGCAAG GCCTTGGAGG CGGCGGGCCA AGACTTCTCC      1680

CTGGACCTCC GCAGCACTGG CATTTGCCCC TCTGGATTGG GGAGCCTCGT GGGACTCAGC      1740

TGTGTCACCC GTTTCAGGGC TGCCTTGAGC GACACGGTGG CGCTGTGGGA GTCCCTGCGG      1800

CAGCATGGGG AGACCAAGCT ACTTCAGGCA GCAGAGGAGA AGTTCACCAT CGAGCCTTTC      1860

AAAGCCAAGT CCCTGAAGGA TGTGGAAGAC CTGGGAAAGC TTGTGCAGAC TCAGAGGACG      1920

AGAAGTTCCT CGGAAGACAC AGCTGGGGAG CTCCCTGCTG TTCGGGACCT AAAGAAACTG      1980

GAGTTTGCGC TGGGCCCTGT CTCAGGCCCC CAGGCTTTCC CCAAACTGGT GCGGATCCTC      2040

ACGGCCTTTT CCTCCCTGCA GCATCTGGAC CTGGATGCGC TGAGTGAGAA CAAGATCGGG      2100

GACGAGGGTG TCTCGCAGCT CTCAGCCACC TTCCCCCAGC TGAAGTCCTT GGAAACCCTC      2160

AATCTGTCCC AGAACAACAT CACTGACCTG GGTGCCTACA AACTCGCCGA GGCCCTGCCT      2220

TCGCTCGCTG CATCCCTGCT CAGGCTAAGC TTGTACAATA ACTGCATCTG CGACGTGGGA      2280

GCCGAGAGCT TGGCTCGTGT GCTTCCGGAC ATGGTGTCCC TCCGGGTGAT GGACGCAAGT      2340

TCACGGCTGC CGGGGCCCAG CAGCTCGCTG CCAGCCTTCG GAGGTGTCCT CATGTGGAGA      2400

CGCTGGCGAT GTGGACGCCC ACCATCCCAT TCAGTGTCCA GGAACACCTG CAACAACAGG      2460

ATTCACGGAT CAGCCTGAGA                                                  2480

(2) INFORMATION FOR SEQ ID NO: 16:

(i) SEQUENCE CHARACTERISTICS:
        (A) LENGTH: 1207 amino acids
        (B) TYPE: amino acid
        (D) TOPOLOGY: linear (ii) MOLECULE TYPE: peptide (ix) FEATURE:
        (A) NAME/KEY: cIIta of type I (xi) SEQUENCE DESCRIPTION: SEQ ID NO: 16:

Met Asn Asn Phe Gln Ala Ile Leu Thr Gln Val Arg Met Leu Leu Ser
1               5                   10                  15

Ser His Gln Pro Ser Leu Val Gln Ala Leu Leu Asp Asn Leu Leu Lys
            20                  25                  30

Glu Asp Leu Leu Ser Arg Glu Tyr His Cys Thr Leu Leu His Glu Pro
        35                  40                  45

Asp Ser Glu Ala Leu Ala Arg Lys Ile Ser Leu Thr Leu Leu Glu Lys
    50                  55                  60

Gly Asp Leu Asp Leu Ala Leu Leu Gly Trp Ala Arg Ser Gly Leu Gln
65                  70                  75                  80

Pro Pro Ala Ala Glu Arg Gly Pro Gly His Ser Asp His Gly Gly Ser
                85                  90                  95

Ser Gln Cys Ala Thr Met Glu Leu Gly Pro Leu Glu Gly Gly Tyr Leu
            100                 105                 110

Glu Leu Leu Asn Ser Asp Ala Asp Pro Leu Cys Leu Tyr His Phe Tyr
        115                 120                 125

Asp Gln Met Asp Leu Ala Gly Glu Glu Glu Ile Glu Leu Tyr Ser Glu
    130                 135                 140

Pro Asp Thr Asp Thr Ile Asn Cys Asp Gln Phe Ser Arg Leu Leu Cys
145                 150                 155                 160

Asp Met Glu Gly Asp Glu Glu Thr Arg Glu Ala Tyr Ala Asn Ile Ala
                165                 170                 175

Glu Leu Asp Gln Tyr Val Phe Gln Asp Ser Gln Leu Glu Gly Leu Ser
```

```
              180                 185                 190
Lys Asp Ile Phe Lys His Ile Gly Pro Asp Glu Val Ile Gly Glu Ser
              195                 200                 205
Met Glu Met Pro Ala Glu Val Gly Gln Lys Ser Gln Lys Arg Pro Phe
210                 215                 220
Pro Glu Glu Leu Pro Ala Asp Leu Lys His Trp Lys Pro Ala Glu Pro
225                 230                 235                 240
Pro Thr Val Val Thr Gly Ser Leu Leu Val Gly Pro Val Ser Asp Cys
              245                 250                 255
Ser Thr Leu Pro Cys Leu Pro Leu Pro Ala Leu Phe Asn Gln Glu Pro
              260                 265                 270
Ala Ser Gly Gln Met Arg Leu Glu Lys Thr Asp Gln Ile Pro Met Pro
              275                 280                 285
Phe Ser Ser Ser Leu Ser Cys Leu Asn Leu Pro Glu Gly Pro Ile
              290                 295                 300
Gln Phe Val Pro Thr Ile Ser Thr Leu Pro His Gly Leu Trp Gln Ile
305                 310                 315                 320
Ser Glu Ala Gly Thr Gly Val Ser Ser Ile Phe Ile Tyr His Gly Glu
              325                 330                 335
Val Pro Gln Ala Ser Gln Val Pro Pro Ser Gly Phe Thr Val His
              340                 345                 350
Gly Leu Pro Thr Ser Pro Asp Arg Pro Gly Ser Thr Ser Pro Phe Ala
              355                 360                 365
Pro Ser Ala Thr Asp Leu Pro Ser Met Pro Glu Pro Ala Leu Thr Ser
              370                 375                 380
Arg Ala Asn Met Thr Glu His Lys Thr Ser Pro Thr Gln Cys Pro Ala
385                 390                 395                 400
Ala Gly Glu Val Ser Asn Lys Leu Pro Lys Trp Pro Glu Pro Val Glu
              405                 410                 415
Gln Phe Tyr Arg Ser Leu Gln Asp Thr Tyr Gly Ala Glu Pro Ala Gly
              420                 425                 430
Pro Asp Gly Ile Leu Val Glu Val Asp Leu Val Gln Ala Arg Leu Glu
              435                 440                 445
Arg Ser Ser Ser Lys Ser Leu Glu Arg Glu Leu Ala Thr Pro Asp Trp
450                 455                 460
Ala Glu Arg Gln Leu Ala Gln Gly Gly Leu Ala Glu Val Leu Leu Ala
465                 470                 475                 480
Ala Lys Glu His Arg Arg Pro Arg Glu Thr Arg Val Ile Ala Val Leu
              485                 490                 495
Gly Lys Ala Gly Gln Gly Lys Ser Tyr Trp Ala Gly Ala Val Ser Arg
              500                 505                 510
Ala Trp Ala Cys Gly Arg Leu Pro Gln Tyr Asp Phe Val Phe Ser Val
              515                 520                 525
Pro Cys His Cys Leu Asn Arg Pro Gly Asp Ala Tyr Gly Leu Gln Asp
              530                 535                 540
Leu Leu Phe Ser Leu Gly Pro Gln Pro Leu Val Ala Ala Asp Glu Val
545                 550                 555                 560
Phe Ser His Ile Leu Lys Arg Pro Asp Arg Val Leu Leu Ile Leu Asp
              565                 570                 575
Ala Phe Glu Glu Leu Glu Ala Gln Asp Gly Phe Leu His Ser Thr Cys
              580                 585                 590
Gly Pro Ala Pro Ala Glu Pro Cys Ser Leu Arg Gly Leu Leu Ala Gly
              595                 600                 605
```

-continued

```
Leu Phe Gln Lys Lys Leu Leu Arg Gly Cys Thr Leu Leu Leu Thr Ala
    610                 615                 620

Arg Pro Arg Gly Arg Leu Val Gln Ser Leu Ser Lys Ala Asp Ala Leu
625                 630                 635                 640

Phe Glu Leu Ser Gly Phe Ser Met Glu Gln Ala Gln Ala Tyr Val Met
                645                 650                 655

Arg Tyr Phe Glu Ser Ser Gly Met Thr Glu His Gln Asp Arg Ala Leu
                660                 665                 670

Thr Leu Leu Arg Asp Arg Pro Leu Leu Ser His Ser His Ser Pro
            675                 680                 685

Thr Leu Cys Arg Ala Val Cys Gln Leu Ser Glu Ala Leu Leu Glu Leu
    690                 695                 700

Gly Glu Asp Ala Lys Leu Pro Ser Thr Leu Thr Gly Leu Tyr Val Gly
705                 710                 715                 720

Leu Leu Gly Arg Ala Ala Leu Asp Ser Pro Pro Gly Ala Leu Ala Glu
                725                 730                 735

Leu Ala Lys Leu Ala Trp Glu Leu Gly Arg Arg His Gln Ser Thr Leu
                740                 745                 750

Gln Glu Asp Gln Phe Pro Ser Ala Asp Val Arg Thr Trp Ala Met Ala
            755                 760                 765

Lys Gly Leu Val Gln His Pro Pro Arg Ala Ala Glu Ser Glu Leu Ala
    770                 775                 780

Phe Pro Ser Phe Leu Leu Gln Cys Phe Leu Gly Ala Leu Trp Leu Ala
785                 790                 795                 800

Leu Ser Gly Glu Ile Lys Asp Lys Glu Leu Pro Gln Tyr Leu Ala Leu
                805                 810                 815

Thr Pro Arg Lys Lys Arg Pro Tyr Asp Asn Trp Leu Glu Gly Val Pro
            820                 825                 830

Arg Phe Leu Ala Gly Leu Ile Phe Gln Pro Pro Ala Arg Cys Leu Gly
            835                 840                 845

Ala Leu Leu Gly Pro Ser Ala Ala Ser Val Asp Arg Lys Gln Lys
    850                 855                 860

Val Leu Ala Arg Tyr Leu Lys Arg Leu Gln Pro Gly Thr Leu Arg Ala
865                 870                 875                 880

Arg Gln Leu Leu Glu Leu Leu His Cys Ala His Glu Ala Glu Glu Ala
                885                 890                 895

Gly Ile Trp Gln His Val Val Gln Glu Leu Pro Gly Arg Leu Ser Phe
            900                 905                 910

Leu Gly Thr Arg Leu Thr Pro Pro Asp Ala His Val Leu Gly Lys Ala
            915                 920                 925

Leu Glu Ala Ala Gly Gln Asp Phe Ser Leu Asp Leu Arg Ser Thr Gly
    930                 935                 940

Ile Cys Pro Ser Gly Leu Gly Ser Leu Val Gly Leu Ser Cys Val Thr
945                 950                 955                 960

Arg Phe Arg Ala Ala Leu Ser Asp Thr Val Ala Leu Trp Glu Ser Leu
                965                 970                 975

Arg Gln His Gly Glu Thr Lys Leu Leu Gln Ala Ala Glu Glu Lys Phe
            980                 985                 990

Thr Ile Glu Pro Phe Lys Ala Lys Ser Leu Lys Asp Val Glu Asp Leu
    995                 1000                1005

Gly Lys Leu Val Gln Thr Gln Arg Thr Arg Ser Ser Glu Asp Thr
    1010                1015                1020
```

-continued

```
Ala Gly Glu Leu Pro Ala Val Arg Asp Leu Lys Lys Leu Glu Phe Ala
1025                1030                1035                1040

Leu Gly Pro Val Ser Gly Pro Gln Ala Phe Pro Lys Leu Val Arg Ile
                1045                1050                1055

Leu Thr Ala Phe Ser Ser Leu Gln His Leu Asp Leu Asp Ala Leu Ser
                1060                1065                1070

Glu Asn Lys Ile Gly Asp Glu Gly Val Ser Gln Leu Ser Ala Thr Phe
            1075                1080                1085

Pro Gln Leu Lys Ser Leu Glu Thr Leu Asn Leu Ser Gln Asn Asn Ile
        1090                1095                1100

Thr Asp Leu Gly Ala Tyr Lys Leu Ala Glu Ala Leu Pro Ser Leu Ala
1105                1110                1115                1120

Ala Ser Leu Leu Arg Leu Ser Leu Tyr Asn Asn Cys Ile Cys Asp Val
                1125                1130                1135

Gly Ala Glu Ser Leu Ala Arg Val Leu Pro Asp Met Val Ser Leu Arg
                1140                1145                1150

Val Met Asp Val Gln Tyr Asn Lys Phe Thr Ala Ala Gly Ala Gln Gln
            1155                1160                1165

Leu Ala Ala Ser Leu Arg Arg Cys Pro His Val Glu Thr Leu Ala Met
        1170                1175                1180

Trp Thr Pro Thr Ile Pro Phe Ser Val Gln Glu His Leu Gln Gln Gln
1185                1190                1195                1200

Asp Ser Arg Ile Ser Leu Arg
                1205

(2) INFORMATION FOR SEQ ID NO: 17:

(i) SEQUENCE CHARACTERISTICS:
        (A) LENGTH: 1106 amino acids
        (B) TYPE: amino acid
        (D) TOPOLOGY: linear (ii) MOLECULE TYPE: peptide (ix) FEATURE:
        (A) NAME/KEY:cIIta of type I (xi) SEQUENCE DESCRIPTION: SEQ ID NO: 17:

Met Glu Leu Gly Pro Leu Glu Gly Gly Tyr Leu Glu Leu Leu Asn Ser
1               5                   10                  15

Asp Ala Asp Pro Leu Cys Leu Tyr His Phe Tyr Asp Gln Met Asp Leu
            20                  25                  30

Ala Gly Glu Glu Glu Ile Glu Leu Tyr Ser Glu Pro Asp Thr Asp Thr
            35                  40                  45

Ile Asn Cys Asp Gln Phe Ser Arg Leu Leu Cys Asp Met Glu Gly Asp
        50                  55                  60

Glu Glu Thr Arg Glu Ala Tyr Ala Asn Ile Ala Glu Leu Asp Gln Tyr
65                  70                  75                  80

Val Phe Gln Asp Ser Gln Leu Glu Gly Leu Ser Lys Asp Ile Phe Lys
                85                  90                  95

His Ile Gly Pro Asp Glu Val Ile Gly Glu Ser Met Glu Met Pro Ala
                100                 105                 110

Glu Val Gly Gln Lys Ser Gln Lys Arg Pro Phe Pro Glu Glu Leu Pro
            115                 120                 125

Ala Asp Leu Lys His Trp Lys Pro Ala Glu Pro Thr Val Val Thr
        130                 135                 140

Gly Ser Leu Leu Val Gly Pro Val Ser Asp Cys Ser Thr Leu Pro Cys
```

-continued

```
            145                 150                 155                 160
Leu Pro Leu Pro Ala Leu Phe Asn Gln Glu Pro Ala Ser Gly Gln Met
                165                 170                 175
Arg Leu Glu Lys Thr Asp Gln Ile Pro Met Pro Phe Ser Ser Ser Ser
                180                 185                 190
Leu Ser Cys Leu Asn Leu Pro Glu Gly Pro Ile Gln Phe Val Pro Thr
            195                 200                 205
Ile Ser Thr Leu Pro His Gly Leu Trp Gln Ile Ser Glu Ala Gly Thr
        210                 215                 220
Gly Val Ser Ser Ile Phe Ile Tyr His Gly Glu Val Pro Gln Ala Ser
225                 230                 235                 240
Gln Val Pro Pro Pro Ser Gly Phe Thr Val His Gly Leu Pro Thr Ser
                245                 250                 255
Pro Asp Arg Pro Gly Ser Thr Ser Pro Phe Ala Pro Ser Ala Thr Asp
            260                 265                 270
Leu Pro Ser Met Pro Glu Pro Ala Leu Thr Ser Arg Ala Asn Met Thr
        275                 280                 285
Glu His Lys Thr Ser Pro Thr Gln Cys Pro Ala Ala Gly Glu Val Ser
    290                 295                 300
Asn Lys Leu Pro Lys Trp Pro Glu Pro Val Glu Gln Phe Tyr Arg Ser
305                 310                 315                 320
Leu Gln Asp Thr Tyr Gly Ala Glu Pro Ala Gly Pro Asp Gly Ile Leu
                325                 330                 335
Val Glu Val Asp Leu Val Gln Ala Arg Leu Glu Arg Ser Ser Ser Lys
                340                 345                 350
Ser Leu Glu Arg Glu Leu Ala Thr Pro Asp Trp Ala Glu Arg Gln Leu
            355                 360                 365
Ala Gln Gly Gly Leu Ala Glu Val Leu Leu Ala Lys Glu His Arg
        370                 375                 380
Arg Pro Arg Glu Thr Arg Val Ile Ala Val Leu Gly Lys Ala Gly Gln
385                 390                 395                 400
Gly Lys Ser Tyr Trp Ala Gly Ala Val Ser Arg Ala Trp Ala Cys Gly
                405                 410                 415
Arg Leu Pro Gln Tyr Asp Phe Val Phe Ser Val Pro Cys His Cys Leu
                420                 425                 430
Asn Arg Pro Gly Asp Ala Tyr Gly Leu Gln Asp Leu Leu Phe Ser Leu
            435                 440                 445
Gly Pro Gln Pro Leu Val Ala Ala Asp Glu Val Phe Ser His Ile Leu
        450                 455                 460
Lys Arg Pro Asp Arg Val Leu Leu Ile Leu Asp Ala Phe Glu Glu Leu
465                 470                 475                 480
Glu Ala Gln Asp Gly Phe Leu His Ser Thr Cys Gly Pro Ala Pro Ala
                485                 490                 495
Glu Pro Cys Ser Leu Arg Gly Leu Leu Ala Gly Leu Phe Gln Lys Lys
            500                 505                 510
Leu Leu Arg Gly Cys Thr Leu Leu Thr Ala Arg Pro Arg Gly Arg
        515                 520                 525
Leu Val Gln Ser Leu Ser Lys Ala Asp Ala Leu Phe Glu Leu Ser Gly
    530                 535                 540
Phe Ser Met Glu Gln Ala Gln Ala Tyr Val Met Arg Tyr Phe Glu Ser
545                 550                 555                 560
Ser Gly Met Thr Glu His Gln Asp Arg Ala Leu Thr Leu Leu Arg Asp
                565                 570                 575
```

```
Arg Pro Leu Leu Leu Ser His Ser His Ser Pro Thr Leu Cys Arg Ala
            580                 585                 590

Val Cys Gln Leu Ser Glu Ala Leu Leu Glu Leu Gly Glu Asp Ala Lys
        595                 600                 605

Leu Pro Ser Thr Leu Thr Gly Leu Tyr Val Gly Leu Leu Gly Arg Ala
        610                 615                 620

Ala Leu Asp Ser Pro Pro Gly Ala Leu Ala Glu Leu Ala Lys Leu Ala
625                 630                 635                 640

Trp Glu Leu Gly Arg Arg His Gln Ser Thr Leu Gln Glu Asp Gln Phe
                645                 650                 655

Pro Ser Ala Asp Val Arg Thr Trp Ala Met Ala Lys Gly Leu Val Gln
            660                 665                 670

His Pro Pro Arg Ala Ala Glu Ser Glu Leu Ala Phe Pro Ser Phe Leu
        675                 680                 685

Leu Gln Cys Phe Leu Gly Ala Leu Trp Leu Ala Leu Ser Gly Glu Ile
        690                 695                 700

Lys Asp Lys Glu Leu Pro Gln Tyr Leu Ala Leu Thr Pro Arg Lys Lys
705                 710                 715                 720

Arg Pro Tyr Asp Asn Trp Leu Glu Gly Val Pro Arg Phe Leu Ala Gly
                725                 730                 735

Leu Ile Phe Gln Pro Pro Ala Arg Cys Leu Gly Ala Leu Leu Gly Pro
                740                 745                 750

Ser Ala Ala Ser Val Asp Arg Lys Gln Lys Val Leu Ala Arg Tyr
            755                 760                 765

Leu Lys Arg Leu Gln Pro Gly Thr Leu Arg Ala Arg Gln Leu Leu Glu
770                 775                 780

Leu Leu His Cys Ala His Glu Ala Glu Glu Ala Gly Ile Trp Gln His
785                 790                 795                 800

Val Val Gln Glu Leu Pro Gly Arg Leu Ser Phe Leu Gly Thr Arg Leu
                805                 810                 815

Thr Pro Pro Asp Ala His Val Leu Gly Lys Ala Leu Glu Ala Ala Gly
            820                 825                 830

Gln Asp Phe Ser Leu Asp Leu Arg Ser Thr Gly Ile Cys Pro Ser Gly
            835                 840                 845

Leu Gly Ser Leu Val Gly Leu Ser Cys Val Thr Arg Phe Arg Ala Ala
850                 855                 860

Leu Ser Asp Thr Val Ala Leu Trp Glu Ser Leu Arg Gln His Gly Glu
865                 870                 875                 880

Thr Lys Leu Leu Gln Ala Ala Glu Glu Lys Phe Thr Ile Glu Pro Phe
                885                 890                 895

Lys Ala Lys Ser Leu Lys Asp Val Glu Asp Leu Gly Lys Leu Val Gln
            900                 905                 910

Thr Gln Arg Thr Arg Ser Ser Ser Glu Asp Thr Ala Gly Glu Leu Pro
        915                 920                 925

Ala Val Arg Asp Leu Lys Lys Leu Glu Phe Ala Leu Gly Pro Val Ser
        930                 935                 940

Gly Pro Gln Ala Phe Pro Lys Leu Val Arg Ile Leu Thr Ala Phe Ser
945                 950                 955                 960

Ser Leu Gln His Leu Asp Leu Asp Ala Leu Ser Glu Asn Lys Ile Gly
                965                 970                 975

Asp Glu Gly Val Ser Gln Leu Ser Ala Thr Phe Pro Gln Leu Lys Ser
            980                 985                 990
```

-continued

```
Leu Glu Thr Leu Asn Leu Ser Gln Asn Asn Ile Thr Asp Leu Gly Ala
        995                 1000                1005

Tyr Lys Leu Ala Glu Ala Leu Pro Ser Leu Ala Ala Ser Leu Leu Arg
    1010                1015                1020

Leu Ser Leu Tyr Asn Asn Cys Ile Cys Asp Val Gly Ala Glu Ser Leu
1025                1030                1035                1040

Ala Arg Val Leu Pro Asp Met Val Ser Leu Arg Val Met Asp Val Gln
                1045                1050                1055

Tyr Asn Lys Phe Thr Ala Ala Gly Ala Gln Gln Leu Ala Ala Ser Leu
                1060                1065                1070

Arg Arg Cys Pro His Val Glu Thr Leu Ala Met Trp Thr Pro Thr Ile
                1075                1080                1085

Pro Phe Ser Val Gln Glu His Leu Gln Gln Gln Asp Ser Arg Ile Ser
                1090                1095                1100

Leu Arg
1105
```

(2) INFORMATION FOR SEQ ID NO: 18:

(i) SEQUENCE CHARACTERISTICS:
        (A) LENGTH: 1130 amino acids
        (B) TYPE: amino acid
        (D) TOPOLOGY: linear (ii) MOLECULE TYPE: peptide (ix) FEATURE:
        (A) NAME/KEY: cIIta (xi) SEQUENCE DESCRIPTION: SEQ ID NO: 18:

```
Met Arg Cys Leu Ala Pro Arg Pro Ala Gly Ser Tyr Leu Ser Glu Pro
1               5                   10                  15

Gln Gly Ser Ser Gln Cys Ala Thr Met Glu Leu Gly Pro Leu Glu Gly
            20                  25                  30

Gly Tyr Leu Glu Leu Leu Asn Ser Asp Ala Asp Pro Leu Cys Leu Tyr
        35                  40                  45

His Phe Tyr Asp Gln Met Asp Leu Ala Gly Glu Glu Ile Glu Leu
    50                  55                  60

Tyr Ser Glu Pro Asp Thr Asp Thr Ile Asn Cys Asp Gln Phe Ser Arg
65                  70                  75                  80

Leu Leu Cys Asp Met Glu Gly Asp Glu Glu Thr Arg Glu Ala Tyr Ala
                85                  90                  95

Asn Ile Ala Glu Leu Asp Gln Tyr Val Phe Gln Asp Ser Gln Leu Glu
            100                 105                 110

Gly Leu Ser Lys Asp Ile Phe Lys His Ile Gly Pro Asp Glu Val Ile
        115                 120                 125

Gly Glu Ser Met Glu Met Pro Ala Glu Val Gly Gln Lys Ser Gln Lys
    130                 135                 140

Arg Pro Phe Pro Glu Glu Leu Pro Ala Asp Leu Lys His Trp Lys Pro
145                 150                 155                 160

Ala Glu Pro Pro Thr Val Val Thr Gly Ser Leu Leu Val Gly Pro Val
                165                 170                 175

Ser Asp Cys Ser Thr Leu Pro Cys Leu Pro Leu Pro Ala Leu Phe Asn
            180                 185                 190

Gln Glu Pro Ala Ser Gly Gln Met Arg Leu Glu Lys Thr Asp Gln Ile
        195                 200                 205

Pro Met Pro Phe Ser Ser Ser Ser Leu Ser Cys Leu Asn Leu Pro Glu
```

```
              210                 215                 220
Gly Pro Ile Gln Phe Val Pro Thr Ile Ser Thr Leu Pro His Gly Leu
225                 230                 235                 240

Trp Gln Ile Ser Glu Ala Gly Thr Gly Val Ser Ser Ile Phe Ile Tyr
                245                 250                 255

His Gly Glu Val Pro Gln Ala Ser Gln Val Pro Pro Ser Gly Phe
                260                 265                 270

Thr Val His Gly Leu Pro Thr Ser Pro Asp Arg Pro Gly Ser Thr Ser
            275                 280                 285

Pro Phe Ala Pro Ser Ala Thr Asp Leu Pro Ser Met Pro Glu Pro Ala
290                 295                 300

Leu Thr Ser Arg Ala Asn Met Thr Glu His Lys Thr Ser Pro Thr Gln
305                 310                 315                 320

Cys Pro Ala Ala Gly Glu Val Ser Asn Lys Leu Pro Lys Trp Pro Glu
                325                 330                 335

Pro Val Glu Gln Phe Tyr Arg Ser Leu Gln Asp Thr Tyr Gly Ala Glu
                340                 345                 350

Pro Ala Gly Pro Asp Gly Ile Leu Val Glu Val Asp Leu Val Gln Ala
                355                 360                 365

Arg Leu Glu Arg Ser Ser Lys Ser Leu Glu Arg Glu Leu Ala Thr
370                 375                 380

Pro Asp Trp Ala Glu Arg Gln Leu Ala Gln Gly Leu Ala Glu Val
385                 390                 395                 400

Leu Leu Ala Ala Lys Glu His Arg Arg Pro Arg Glu Thr Arg Val Ile
                405                 410                 415

Ala Val Leu Gly Lys Ala Gly Gln Gly Lys Ser Tyr Trp Ala Gly Ala
                420                 425                 430

Val Ser Arg Ala Trp Ala Cys Gly Arg Leu Pro Gln Tyr Asp Phe Val
            435                 440                 445

Phe Ser Val Pro Cys His Cys Leu Asn Arg Pro Gly Asp Ala Tyr Gly
            450                 455                 460

Leu Gln Asp Leu Leu Phe Ser Leu Gly Pro Gln Pro Leu Val Ala Ala
465                 470                 475                 480

Asp Glu Val Phe Ser His Ile Leu Lys Arg Pro Asp Arg Val Leu Leu
                485                 490                 495

Ile Leu Asp Ala Phe Glu Glu Leu Glu Ala Gln Asp Gly Phe Leu His
                500                 505                 510

Ser Thr Cys Gly Pro Ala Pro Ala Glu Pro Cys Ser Leu Arg Gly Leu
            515                 520                 525

Leu Ala Gly Leu Phe Gln Lys Lys Leu Leu Arg Gly Cys Thr Leu Leu
530                 535                 540

Leu Thr Ala Arg Pro Arg Gly Arg Leu Val Gln Ser Leu Ser Lys Ala
545                 550                 555                 560

Asp Ala Leu Phe Glu Leu Ser Gly Phe Ser Met Glu Gln Ala Gln Ala
                565                 570                 575

Tyr Val Met Arg Tyr Phe Glu Ser Ser Gly Met Thr His Gln Asp
            580                 585                 590

Arg Ala Leu Thr Leu Leu Arg Asp Arg Pro Leu Leu Leu Ser His Ser
            595                 600                 605

His Ser Pro Thr Leu Cys Arg Ala Val Cys Gln Leu Ser Glu Ala Leu
        610                 615                 620

Leu Glu Leu Gly Glu Asp Ala Lys Leu Pro Ser Thr Leu Thr Gly Leu
625                 630                 635                 640
```

-continued

```
Tyr Val Gly Leu Leu Gly Arg Ala Ala Leu Asp Ser Pro Pro Gly Ala
            645                 650                 655
Leu Ala Glu Leu Ala Lys Leu Ala Trp Glu Leu Gly Arg Arg His Gln
            660                 665                 670
Ser Thr Leu Gln Glu Asp Gln Phe Pro Ser Ala Asp Val Arg Thr Trp
            675                 680                 685
Ala Met Ala Lys Gly Leu Val Gln His Pro Pro Arg Ala Ala Glu Ser
690                 695                 700
Glu Leu Ala Phe Pro Ser Phe Leu Leu Gln Cys Phe Leu Gly Ala Leu
705                 710                 715                 720
Trp Leu Ala Leu Ser Gly Glu Ile Lys Asp Lys Glu Leu Pro Gln Tyr
            725                 730                 735
Leu Ala Leu Thr Pro Arg Lys Lys Arg Pro Tyr Asp Asn Trp Leu Glu
            740                 745                 750
Gly Val Pro Arg Phe Leu Ala Gly Leu Ile Phe Gln Pro Pro Ala Arg
            755                 760                 765
Cys Leu Gly Ala Leu Leu Gly Pro Ser Ala Ala Ser Val Asp Arg
770                 775                 780
Lys Gln Lys Val Leu Ala Arg Tyr Leu Lys Arg Leu Gln Pro Gly Thr
785                 790                 795                 800
Leu Arg Ala Arg Gln Leu Leu Glu Leu Leu His Cys Ala His Glu Ala
            805                 810                 815
Glu Glu Ala Gly Ile Trp Gln His Val Val Gln Glu Leu Pro Gly Arg
            820                 825                 830
Leu Ser Phe Leu Gly Thr Arg Leu Thr Pro Pro Asp Ala His Val Leu
            835                 840                 845
Gly Lys Ala Leu Glu Ala Ala Gly Gln Asp Phe Ser Leu Asp Leu Arg
850                 855                 860
Ser Thr Gly Ile Cys Pro Ser Gly Leu Gly Ser Leu Val Gly Leu Ser
865                 870                 875                 880
Cys Val Thr Arg Phe Arg Ala Ala Leu Ser Asp Thr Val Ala Leu Trp
            885                 890                 895
Glu Ser Leu Arg Gln His Gly Glu Thr Lys Leu Leu Gln Ala Ala Glu
            900                 905                 910
Glu Lys Phe Thr Ile Glu Pro Phe Lys Ala Lys Ser Leu Lys Asp Val
            915                 920                 925
Glu Asp Leu Gly Lys Leu Val Gln Thr Gln Arg Thr Arg Ser Ser Ser
930                 935                 940
Glu Asp Thr Ala Gly Glu Leu Pro Ala Val Arg Asp Leu Lys Lys Leu
945                 950                 955                 960
Glu Phe Ala Leu Gly Pro Val Ser Gly Pro Gln Ala Phe Pro Lys Leu
            965                 970                 975
Val Arg Ile Leu Thr Ala Phe Ser Ser Leu Gln His Leu Asp Leu Asp
            980                 985                 990
Ala Leu Ser Glu Asn Lys Ile Gly Asp Glu Gly Val Ser Gln Leu Ser
            995                 1000                1005
Ala Thr Phe Pro Gln Leu Lys Ser Leu Glu Thr Leu Asn Leu Ser Gln
            1010                1015                1020
Asn Asn Ile Thr Asp Leu Gly Ala Tyr Lys Leu Ala Glu Ala Leu Pro
1025                1030                1035                1040
Ser Leu Ala Ala Ser Leu Leu Arg Leu Ser Leu Tyr Asn Asn Cys Ile
            1045                1050                1055
```

```
Cys Asp Val Gly Ala Glu Ser Leu Ala Arg Val Leu Pro Asp Met Val
            1060                1065                1070

Ser Leu Arg Val Met Asp Val Gln Tyr Asn Lys Phe Thr Ala Ala Gly
            1075                1080                1085

Ala Gln Gln Leu Ala Ala Ser Leu Arg Arg Cys Pro His Val Glu Thr
            1090                1095                1100

Leu Ala Met Trp Thr Pro Thr Ile Pro Phe Ser Val Gln Glu His Leu
1105                1110                1115                1120

Gln Gln Gln Asp Ser Arg Ile Ser Leu Arg
                1125                1130

(2) INFORMATION FOR SEQ ID NO: 19:

(i) SEQUENCE CHARACTERISTICS:
        (A) LENGTH: 830 amino acids
        (B) TYPE: amino acid
        (D) TOPOLOGY: linear (ii) MOLECULE TYPE: peptide (xi) SEQUENCE DESCRIPTION: SEQ ID NO: 19:

Pro Glu Pro Ala Leu Thr Ser Arg Ala Asn Met Thr Glu His Lys Thr
1               5                   10                  15

Ser Pro Thr Gln Cys Pro Ala Ala Gly Glu Val Ser Asn Lys Leu Pro
            20                  25                  30

Lys Trp Pro Glu Pro Val Glu Gln Phe Tyr Arg Ser Leu Gln Asp Thr
            35                  40                  45

Tyr Gly Ala Glu Pro Ala Gly Pro Asp Gly Ile Leu Val Glu Val Asp
        50                  55                  60

Leu Val Gln Ala Arg Leu Glu Arg Ser Ser Lys Ser Leu Glu Arg
65                  70                  75                  80

Glu Leu Ala Thr Pro Asp Trp Ala Glu Arg Gln Leu Ala Gln Gly Gly
            85                  90                  95

Leu Ala Glu Val Leu Leu Ala Ala Lys Glu His Arg Arg Pro Arg Glu
            100                 105                 110

Thr Arg Val Ile Ala Val Leu Gly Lys Ala Gly Gln Gly Lys Ser Tyr
            115                 120                 125

Trp Ala Gly Ala Val Ser Arg Ala Trp Ala Cys Gly Arg Leu Pro Gln
            130                 135                 140

Tyr Asp Phe Val Phe Ser Val Pro Cys His Cys Leu Asn Arg Pro Gly
145                 150                 155                 160

Asp Ala Tyr Gly Leu Gln Asp Leu Leu Phe Ser Leu Gly Pro Gln Pro
                165                 170                 175

Leu Val Ala Ala Asp Glu Val Phe Ser His Ile Leu Lys Arg Pro Asp
            180                 185                 190

Arg Val Leu Leu Ile Leu Asp Ala Phe Glu Glu Leu Glu Ala Gln Asp
            195                 200                 205

Gly Phe Leu His Ser Thr Cys Gly Pro Ala Pro Ala Glu Pro Cys Ser
            210                 215                 220

Leu Arg Gly Leu Leu Ala Gly Leu Phe Gln Lys Lys Leu Leu Arg Gly
225                 230                 235                 240

Cys Thr Leu Leu Leu Thr Ala Arg Pro Arg Gly Arg Leu Val Gln Ser
                245                 250                 255

Leu Ser Lys Ala Asp Ala Leu Phe Glu Leu Ser Gly Phe Ser Met Glu
            260                 265                 270

Gln Ala Gln Ala Tyr Val Met Arg Tyr Phe Glu Ser Ser Gly Met Thr
```

```
                275                 280                 285
Glu His Gln Asp Arg Ala Leu Thr Leu Leu Arg Asp Arg Pro Leu Leu
    290                 295                 300

Leu Ser His Ser His Ser Pro Thr Leu Cys Arg Ala Val Cys Gln Leu
305                 310                 315                 320

Ser Glu Ala Leu Leu Glu Leu Gly Glu Asp Ala Lys Leu Pro Ser Thr
                325                 330                 335

Leu Thr Gly Leu Tyr Val Gly Leu Leu Gly Arg Ala Ala Leu Asp Ser
                340                 345                 350

Pro Pro Gly Ala Leu Ala Glu Leu Ala Lys Leu Ala Trp Glu Leu Gly
                355                 360                 365

Arg Arg His Gln Ser Thr Leu Gln Glu Asp Gln Phe Pro Ser Ala Asp
370                 375                 380

Val Arg Thr Trp Ala Met Ala Lys Gly Leu Val Gln His Pro Pro Arg
385                 390                 395                 400

Ala Ala Glu Ser Glu Leu Ala Phe Pro Ser Phe Leu Leu Gln Cys Phe
                405                 410                 415

Leu Gly Ala Leu Trp Leu Ala Leu Ser Gly Glu Ile Lys Asp Lys Glu
                420                 425                 430

Leu Pro Gln Tyr Leu Ala Leu Thr Pro Arg Lys Lys Arg Pro Tyr Asp
                435                 440                 445

Asn Trp Leu Glu Gly Val Pro Arg Phe Leu Ala Gly Leu Ile Phe Glu
    450                 455                 460

Pro Pro Ala Arg Cys Leu Gly Ala Leu Leu Gly Pro Ser Ala Ala Ala
465                 470                 475                 480

Ser Val Asp Arg Lys Gln Lys Val Leu Ala Arg Tyr Leu Lys Arg Leu
                485                 490                 495

Gln Pro Gly Thr Leu Arg Ala Arg Gln Leu Leu Glu Leu Leu His Cys
                500                 505                 510

Ala His Glu Ala Glu Glu Ala Gly Ile Trp Gln His Val Val Gln Glu
                515                 520                 525

Leu Pro Gly Arg Leu Ser Phe Leu Gly Thr Arg Leu Thr Pro Pro Asp
    530                 535                 540

Ala His Val Leu Gly Lys Ala Leu Glu Ala Ala Gly Gln Asp Phe Ser
545                 550                 555                 560

Leu Asp Leu Arg Ser Thr Gly Ile Cys Pro Ser Gly Leu Gly Ser Leu
                565                 570                 575

Val Gly Leu Ser Cys Val Thr Arg Phe Arg Ala Ala Leu Ser Asp Thr
                580                 585                 590

Val Ala Leu Trp Glu Ser Leu Arg Gln His Gly Glu Thr Lys Leu Leu
                595                 600                 605

Gln Ala Ala Glu Glu Lys Phe Thr Ile Glu Pro Phe Lys Ala Lys Ser
    610                 615                 620

Leu Lys Asp Val Glu Asp Leu Gly Lys Leu Val Gln Thr Gln Arg Thr
625                 630                 635                 640

Arg Ser Ser Ser Glu Asp Thr Ala Gly Glu Leu Pro Ala Val Arg Asp
                645                 650                 655

Leu Lys Lys Leu Glu Phe Ala Leu Gly Pro Val Ser Gly Pro Gln Ala
                660                 665                 670

Phe Pro Lys Leu Val Arg Ile Leu Thr Ala Phe Ser Ser Leu Gln His
                675                 680                 685

Leu Asp Leu Asp Ala Leu Ser Glu Asn Lys Ile Gly Asp Glu Gly Val
    690                 695                 700
```

```
Ser Gln Leu Ser Ala Thr Phe Pro Gln Leu Lys Ser Leu Glu Thr Leu
705                 710                 715                 720

Asn Leu Ser Gln Asn Asn Ile Thr Asp Leu Gly Ala Tyr Lys Leu Ala
            725                 730                 735

Glu Ala Leu Pro Ser Leu Ala Ala Ser Leu Leu Arg Leu Ser Leu Tyr
            740                 745                 750

Asn Asn Cys Ile Cys Asp Val Gly Ala Glu Ser Leu Ala Arg Val Leu
            755                 760                 765

Pro Asp Met Val Ser Leu Arg Val Met Asp Val Gln Tyr Asn Lys Phe
            770                 775                 780

Thr Ala Ala Gly Ala Gln Gln Leu Ala Ala Ser Leu Arg Arg Cys Pro
785                 790                 795                 800

His Val Glu Thr Leu Ala Met Trp Thr Pro Thr Ile Pro Phe Ser Val
            805                 810                 815

Gln Glu His Leu Gln Gln Gln Asp Ser Arg Ile Ser Leu Arg
            820                 825                 830
```

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: primer P1

(xi) SEQUENCE DESCRIPTION: SEQ ID NO: 20:

GTCCAGTTCC GCGATATTGG      20

(2) INFORMATION FOR SEQ ID NO: 21:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: primer P2

(xi) SEQUENCE DESCRIPTION: SEQ ID NO: 21:

TCCCTGGTCT CTTCATCA      18

(2) INFORMATION FOR SEQ ID NO: 22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: adaptation primer ADXSC (xi) SEQUENCE DESCRIPTION: SEQ ID NO: 22:

GACTCGAGTC GACATCG      17

(2) INFORMATION FOR SEQ ID NO: 23:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: adaptation primer XSCT17

(xi) SEQUENCE DESCRIPTION: SEQ ID NO: 23:

GACTCGAGTC GACATCGAT                                       19

(2) INFORMATION FOR SEQ ID NO: 24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: primer betaGP5'

(xi) SEQUENCE DESCRIPTION: SEQ ID NO: 24:

TCCCCCAAAA CAGACAGAAT GG                                  22

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: primer betaGP3'

(xi) SEQUENCE DESCRIPTION: SEQ ID NO: 25:

GTCACAGTGC AGTTCACTCA G                                   21